United States Patent
Chatenet et al.

(10) Patent No.: US 9,340,575 B2
(45) Date of Patent: May 17, 2016

(54) AGONISTS AND ANTAGONISTS OF THE UROTENSINERGIC SYSTEM

(75) Inventors: David Chatenet, Laval (CA); Alain Fournier, L'lle Bizard (CA); Myriam Letourneau, Les Cedres (CA)

(73) Assignee: INSTITUT NATIONAL DE LA RECHERCHE SCIENTIFIQUE, Laval, QC (CA)

( * ) Notice: Subject to any disclaimer, the term of this patent is extended or adjusted under 35 U.S.C. 154(b) by 0 days.

(21) Appl. No.: 14/114,757

(22) PCT Filed: May 3, 2012

(86) PCT No.: PCT/CA2012/000421
§ 371 (c)(1),
(2), (4) Date: Jan. 9, 2014

(87) PCT Pub. No.: WO2012/149644
PCT Pub. Date: Nov. 8, 2012

(65) Prior Publication Data
US 2014/0113872 A1   Apr. 24, 2014

Related U.S. Application Data

(60) Provisional application No. 61/481,985, filed on May 3, 2011.

(51) Int. Cl.
| | |
|---|---|
| *A61K 51/08* | (2006.01) |
| *A61K 38/12* | (2006.01) |
| *C07K 7/64* | (2006.01) |
| *C07K 5/10* | (2006.01) |
| *C07K 14/575* | (2006.01) |
| *G01N 33/50* | (2006.01) |
| *C07K 7/02* | (2006.01) |
| *C07K 7/08* | (2006.01) |
| *A61K 38/22* | (2006.01) |

(52) U.S. Cl.
CPC . *C07K 5/10* (2013.01); *A61K 51/08* (2013.01); *A61K 51/088* (2013.01); *C07K 7/02* (2013.01); *C07K 7/083* (2013.01); *C07K 14/57509* (2013.01); *G01N 33/5061* (2013.01); *G01N 33/5088* (2013.01); *A61K 38/2228* (2013.01); *G01N 2333/5751* (2013.01)

(58) Field of Classification Search
CPC . A61K 51/088; A61K 51/08; A61K 38/2228; C07K 14/57509; C07K 5/10; C07K 7/02; C07K 7/083; G01N 33/5088; G01N 2333/5751; G01N 33/5061
See application file for complete search history.

(56) References Cited

FOREIGN PATENT DOCUMENTS

| WO | WO01/37780 | 5/2001 |
| WO | WO2009/094137 | 7/2009 |
| WO | WO/2012/149644 | 11/2012 |

OTHER PUBLICATIONS

Chatenet et al., "Influence of conformationally constrained amino acids at position 4 of urotensin II-related peptide (URP) on its pharmacological properties", Journal of Peptide Science, 16, 118, 2010.
Diallo et al., "[Orn<5>]URP acts as a pure antagonist of urotensinergic receptors in rat cortical astrocytes", Peptides, 29, 813-819, 2007.
Grieco et al., "Recent structure-activity studies of the peptide hormone urotensin-II, a potent vasoconstrictor", Current Medicinal Chemistry, 11, 969-979, 2004.
Grieco et al., "Urotensin-II receptor ligands. From agonist to antagonist activity", Journal of Medicinal Chemistry, 48, 7290-7297, 2005.
Partial Supplementary European Search Report issued in European Patent Application No. 12779758.7, dated Jan. 12, 2015.
Chatenet et al., "Discovery of new antagonists aimed at discriminating UII and URP-mediated biological activities: insight into UII and URP receptor activation," British Journal of Pharmacology, 168, 807-821, 2013.
Batuwangala et al., "Structure-activity relationship study on Tyr9 of urotensin-II(4-11): identification of a partial agonist of the UT receptor", Peptides, 30, 1130-6, 2009.
Behm et al., "Pharmacological characterization of SB-710411 (Cpa-c[D-Cys-Pal-D-Trp-Lys-Val-Cys]-Cpa-amide), a novel peptidic urotensin-II receptor antagonist", British Journal of Pharmacology, 137, 449-58, 2002.
Brkovic et al., "Functional and binding characterizations of urotensin II-related peptides in human and rat urotensin II-receptor assay", The Journal of Pharmacology and Experimental Therapeutics, 306, 1200-9, 2003.
Camarda et al., "A new ligand for the urotensin II receptor", British Journal of Pharmacology, 137, 311-4, 2002.
Chatenet et al., "Structure-activity relationships and structural conformation of a novel urotensin II-related peptide", Peptides, 25, 1819-1830, 2004.
Chatenet et al., "Urocontrin, a novel UT receptor ligand with a unique pharmacological profile", Biochemical Pharmacology, 83-5:608-615, 2012.
Dai et al., "The involvement of transforming growth factor-beta1 secretion in urotensin II-induced collagen synthesis in neonatal cardiac fibroblasts", Regulatory Peptides 140(1-2): 88-93, 2007.
Doan et al., "Effectiveness of the Suzuki-Miyaura cross-coupling reaction for solid-phase peptide modification", Journal of Combinatorial Chemistry, 10, 44-51, 2008.

(Continued)

*Primary Examiner* — Julie Ha
*Assistant Examiner* — Li Ni Komatsu
(74) *Attorney, Agent, or Firm* — Parker Highlander PLLC

(57) ABSTRACT

Novel urotensin II receptor (UT) agonists and antagonists are described herein. More specifically, novel derivatives of urotensin II-related peptide (URP) are described herein.

15 Claims, 11 Drawing Sheets

(56) References Cited

OTHER PUBLICATIONS

Doan et al., "Biochemical and Pharmacological Characterization of Nuclear Urotensin II Binding Sites in Rat Heart", British Journal of Pharmacology: 166(1):243, 2011.

Douglas et al., "Human urotensin-II, the most potent mammalian vasoconstrictor identified to date, as a therapeutic target for the management of cardiovascular disease", Trends Cardiovasc Med 10(6): 229-237, 2000.

Dubessy et al., "Characterization of urotensin II, distribution of urotensin II, urotensin II-related peptide and UT receptor mRNAs in mouse: evidence of urotensin II at the neuromuscular junction", Journal of Neurochemistry, 107, 361-74, 2008.

Gendron et al., "Urotensin II-induced hypotensive responses in Wistar-Kyoto (Wky) and spontaneously hypertensive (Shr) rats", Peptides, 26, 1468-74, 2005.

Guidolin et al., "Urotensin-II as an angiogenic factor", Peptides 31(6): 1219-1224, 2010.

Hassan et al., "Effect of human urotensin-II infusion on hemodynamics and cardiac function", Can J Physiol Pharmacol 81(2): 125-128, 2003.

Hirose et al., "Increased expression of urotensin II, urotensin II-related peptide and urotensin II receptor mRNAs in the cardiovascular organs of hypertensive rats: comparison with endothelin-1", Peptides 30(6): 1124-1129, 2009.

Hoffmanns et al., "Use of the Sonogashira coupling reaction for the "two-step" labelling of phenylalanine peptide side chains with organometallic compounds", Bioconjugate Chem., 17, 204-213, 2006.

Jarry et al., "The vasoactive peptides urotensin II and urotensin II-related peptide regulate astrocyte activity through common and distinct mechanisms: involvement in cell proliferation", Biochemical Journal, 428(1): 113-124, 2010.

Kodama et al., "Site-specific functionalization of proteins by organopalladium reactions", ChemBioChem, 8, 232-238, 2007.

Krum et al., "Therapeutic potential of blockade of the urotensin II system in systemic hypertension", Current Hypertension Reports, 9(1): 53-58, 2007.

Labarrere et al., "Structure-activity relationships of human urotensin II and related analogues on rat aortic ring contraction", Journal of Enzyme Inhibition and Medicinal Chemistry, 18, 77-88, 2003.

Leprince et al., "Structure-activity relationships of urotensin II and URP", Peptides 29, 658-673, 2008.

Maryanoff et al., "Urotensin-II receptor modulators as potential drugs", Journal of Medicinal Chemistry, 53(7): 2695-2708, 2010.

Papadopoulos et al., "Urotensin-II and cardiovascular remodeling", Peptides 29(5): 764-769, 2008.

Prosser et al., "Urotensin II and urotensin II-related peptide (URP) in cardiac ischemia-reperfusion injury", Peptides 29(5): 770-777, 2008.

Ross et al., "Role of urotensin II in health and disease", Am J Physiol Regul Integr Comp Physiol 298(5): R1156-1172, 2010.

Silvestre et al., "Urotensin-II is present in pancreatic extracts and inhibits insulin release in the perfused rat pancreas", European Journal of Endocrinology, 151(6): 803-809, 2004.

Song et al., "Urotensin II and renal function in the rat", Kidney International 69(8): 1360-1368, 2006.

Sugo et al., "Identification of urotensin II-related peptide as the urotensin II-immunoreactive molecule in the rat brain", Biochemical and Biophysical Research Communications 310(3): 860-868, 2003.

Sugo et al., "Another ligand fishing for G protein-coupled receptor 14. Discovery of urotensin II-related peptide in the rat brain", Peptides 29(5): 809-812, 2008.

Vaudry et al., "Urotensin II, from fish to human", Annals of the New York Academy of Sciences, 1200, 53-66, 2010.

Watson et al., "Urotensin II acts centrally to increase epinephrine and ACTH release and cause potent inotropic and chronotropic actions", Hypertension Journal of the American Heart Association, 42(3): 373-379, 2003.

Chatenet et al., "Design, synthesis and biological activities of new urotensin II Related Peptides (URP)", Breaking Away: Proceedings of the 21st American Peptide Symposium, American Peptide Society, 133-134, 2009.

Satoh et al., "Synthesis of 4-substituted phenylalanine derivatives by cross-coupling reaction of p-boronophenylalanines", Tetrahedron Letters, 38, 44, 7645-7648,1997.

Boucard et al., "Photolabelling the rat urotensin II/GPR14 receptor identifies a ligand-binding site in the fourth transmembrane domain", Biochemical Journal, 370, 3, 829-838, 2003.

Holleran et al., "Photolabelling the urotensin II receptor reveals distinct agonist- and partial-agonist-binding sites", Biochemical Journal, 402, 1, 51-61, 2007.

Supplementary European Search Report issued in European Patent Application No. 12779758.7 dated May 13, 2015.

AGONISTS AND ANTAGONISTS OF THE UROTENSINERGIC SYSTEM

This application is a national phase application under 35 U.S.C. §371 of International Application No. PCT/CA2012/000421, filed May 3, 2012, which claims priority to U.S. Provisional Patent Application No. 61/481,985, filed May 3, 2011. The entire text of each of the above-referenced disclosures is specifically incorporated herein by reference.

The sequence listing that is contained in the file named "BECOP0002US ST25.txt", which is 17 KB (as measured in Microsoft Windows®) and was created on Oct. 13, 2015, is filed herewith by electronic submission and is incorporated by reference herein.

FIELD

The present specification broadly relates to novel agonists and antagonists of the urotensinergic system. More specifically, but not exclusively, the present specification relates to novel urotensin II receptor (UT) agonists and antagonists. The present disclosure also relates to a process for the preparation of urotensin II receptor (UT) agonists and antagonists.

BACKGROUND

Despite the currently available drug therapies, cardiovascular diseases remain one of the major causes of ill health in the western world. The identification of additional therapeutic targets, such as G-protein-coupled receptors (GPCR), that may modulate the pathological state has been of interest. Following its desorphanisation, the urotensin II receptor, initially termed sensory epithelium neuropeptide-like receptor or GPR14, has been studied for its implication in the cardiovascular homeostasis in either health or disease state.[1]

Initially isolated more than 20 years ago from the caudal neurosecretory system of teleost fish, urotensin II (UII) has been subsequently characterized in several species including human.[2] This highly conserved cyclic peptide exerts a broad spectrum of biological actions in mammals including the modulation of cardiorenal, pulmonary, central nervous systems, and endocrine functions. Urotensin II has been characterized as an important mediator of the cardiovascular function and has been involved in vasculoprotective and vasculopathic effects. As a matter of fact, concentrations of UII and UII mRNA were reported to be elevated in patients suffering from atherosclerosis, heart failure, hypertension, pre-eclampsia, diabetes, renal disease and liver disease.

UII has been described as the most potent endogenous vasoconstrictor to date, being up to 2 orders of magnitude more potent than endothelin-1 (ET-1), another very potent vasoconstrictor.[3] Recent work in mammals revealed the existence of a second gene encoding a precursor of a UII paralog, called UII-related peptide (URP).[4] This octapeptide, identified in humans, mice and rats, also comprises the highly conserved cyclic hexapeptide core sequence (CFWKYC) (SEQ ID NO: 92) found in UII. However, these peptides differ in the length and composition of their N-terminal domain (Table 1). Pharmacologically, they are the endogenous ligands of the G-protein-coupled receptor termed UT. Both peptides and receptor have been identified in several human tissues including brain, lung, heart, pancreas and kidney as well as vasculature, and until recently they were thought to exert redundant biological activity. More recently, evidence suggested that UII and URP might exert common but also divergent physiological actions.

Previous structure-activity relationship (SAR) studies have highlighted the critical role played by the intracyclic residues, identical in UII and URP sequences, as well as the disulfide bridge. More specifically, the critical role of the Trp-Lys-Tyr (WKY) triad both in the recognition and the activation process has been brought to the forefront. Indeed, replacement of Lys in either UII or URP with ornithine generated antagonists of the urotensinergic system[5,6] whereas the substitution of the Tyr residue in UII with a mono- or a di-iodo tyrosine led to a full and partial agonist respectively.[6,30] Inversion of configuration of the Trp residue in UII or URP resulted in a differential participative effect of this residue in these structures.[7-8]

TABLE 1

Comparison of the primary structure of U-II and URP.[2]

| Species | Origin | Sequence |
|---|---|---|
| U-II | | |
| Lamprey | brain | H-Asn-Asn-Phe-Ser-Asp-Cys-Phe-Trp-Lys-Tyr-Cys-Val-OH (SEQ ID NO: 1) |
| Fugu | spinal cord cDNA | H-Thr-Gly-Asn-Asn-Glu-Cys-Phe-Trp-Lys-Tyr-Cys-Val-OH (SEQ ID NO: 2) |
| Skate | brain | H-Asn-Asn-Phe-Ser-Asp-Cys-Phe-Trp-Lys-Tyr-Cys-Val-OH (SEQ ID NO: 3) |
| Dogfish | spinal cord | H-Asn-Asn-Phe-Ser-Asp-Cys-Phe-Trp-Lys-Tyr-Cys-Val-OH (SEQ ID NO: 4) |
| Sturgeon | spinal cord | H-Gly-Ser-Thr-Ser-Glu-Cys-Phe-Trp-Lys-Tyr-Cys-Val-OH (SEQ ID NO: 5) |
| Paddlefish | spinal cord | H-Gly-Ser-Thr-Ser-Glu-Cys-Phe-Trp-Lys-Tyr-Cys-Val-OH (SEQ ID NO: 6) |
| Goby | urophysis | H-Ala-Gly-Thr-Ala-Asp-Cys-Phe-Trp-Lys-Tyr-Cys-Val-OH (SEQ ID NO: 7) |
| Zebrafish α | urophysis cDNA, spinal cord cDNA | H-Gly-Gly-Gly-Ala-Asp-Cys-Phe-Trp-Lys-Tyr-Cys-Val-OH (SEQ ID NO: 8) |

TABLE 1-continued

Comparison of the primary structure of U-II and URP.[2]

| Species | Origin | Sequence |
|---|---|---|
| Zebrafish β | urophysis cDNA, spinal cord cDNA | H-Gly-Ser-Asn-Thr-Glu-Cys-Phe-Trp-Lys-Tyr-Cys-Val-OH (SEQ ID NO: 9) |
| Sucker A | urophysis | H-Gly-Ser-Gly-Ala-Asp-Cys-Phe-Trp-Lys-Tyr-Cys-Val-OH (SEQ ID NO: 10) |
| Sucker B | urophysis | H-Gly-Ser-Asn-Thr-Glu-Cys-Phe-Trp-Lys-Tyr-Cys-Val-OH (SEQ ID NO: 11) |
| Carp α | urophysis, spinal cord cDNA | H-Gly-Gly-Gly-Ala-Asp-Cys-Phe-Trp-Lys-Tyr-Cys-Val-OH (SEQ ID NO: 12) |
| Carp β1 | urophysis | H-Gly-Gly-Asn-Thr-Glu-Cys-Phe-Trp-Lys-Tyr-Cys-Val-OH (SEQ ID NO: 13) |
| Carp β2 | urophysis | H-Gly-Ser-Asn-Thr-Glu-Cys-Phe-Trp-Lys-Tyr-Cys-Val-OH (SEQ ID NO: 14) |
| Carp γ | urophysis, spinal cord cDNA | H-Gly-Gly-Gly-Ala-Asp-Cys-Phe-Trp-Lys-Tyr-Cys-Ile-OH (SEQ ID NO: 15) |
| Flounder | urophysis, urophysis cDNA | H-Ala-Gly-Thr-Thr-Glu-Cys-Phe-Trp-Lys-Tyr-Cys-Val-OH (SEQ ID NO: 16) |
| Trout | brain | H-Gly-Gly-Asn-Ser-Glu-Cys-Phe-Trp-Lys-Tyr-Cys-Val-OH (SEQ ID NO: 17) |
| Grouper | cDNA | H-Ala-Gly-Asn-Ser-Glu-Cys-Phe-Trp-Lys-Tyr-Cys-Val-OH (SEQ ID NO: 18) |
| Frog | brain, spinal cord cDNA | H-Ala-Gly-Asn-Leu-Ser-Glu-Cys-Phe-Trp-Lys-Tyr-Cys-Val-OH (SEQ ID NO: 19) |
| Chicken | cDNA | H-Gly-Asn-Leu-Ser-Glu-Cys-Phe-Trp-Lys-Tyr-Cys-Val-OH (SEQ ID NO: 20) |
| Zebra finch | predicted | H-Gly-Asn-Leu-Ser-Glu-Cys-Phe-Trp-Lys-Tyr-Cys-Val-OH (SEQ ID NO: 21) |
| Mouse | spinal cord cDNA | <Gln-His-Lys-Gln-His-Gly-Ala-Ala-Pro-Glu-Cys-Phe-Trp-Lys-Tyr-Cys-Ile-OH (SEQ ID NO: 22) |
| Rat | spinal cord cDNA | <Gln-His-Gly-Thr-Ala-Pro-Glu-Cys-Phe-Trp-Lys-Tyr-Cys-Ile-OH (SEQ ID NO: 23) |
| Porcine A | spinal cord | H-Gly-Pro-Thr-Ser-Glu-Cys-Phe-Trp-Lys-Tyr-Cys-Val-OH (SEQ ID NO: 24) |
| Porcine B | spinal cord | H-Gly-Pro-Pro-Ser-Glu-Cys-Phe-Trp-Lys-Tyr-Cys-Val-OH (SEQ ID NO: 25) |
| Cattle | predicted | H-Gly-Pro-Ser-Ser-Glu-Cys-Phe-Trp-Lys-Tyr-Cys-Val-OH (SEQ ID NO: 26) |
| Monkey | spinal cord cDNA | H-Glu-Thr-Pro-Asp-Cys-Phe-Trp-Lys-Tyr-Cys-Val-OH (SEQ ID NO: 27) |
| Chimpanzee | cDNA | H-Glu-Thr-Pro-Asp-Cys-Phe-Trp-Lys-Tyr-Cys-Val-OH (SEQ ID NO: 28) |
| Human | spinal cord cDNA | H-Glu-Thr-Pro-Asp-Cys-Phe-Trp-Lys-Tyr-Cys-Val-OH (SEQ ID NO: 29) |
| URP | | |
| Zebrafish | cDNA | H-Val-Cys-Phe-Trp-Lys-Tyr-Cys-Ser-Gln-Asn-OH (SEQ ID NO: 30) |
| Chicken | spinal cord cDNA | H-Ala-Cys-Phe-Trp-Lys-Tyr-Cys-Ile-OH (SEQ ID NO: 31) |
| Mouse | brain cDNA | H-Ala-Cys-Phe-Trp-Lys-Tyr-Cys-Val-OH (SEQ ID NO: 32) |

TABLE 1-continued

Comparison of the primary structure of U-II and URP.[2]

| Species | Origin | Sequence |
|---|---|---|
| Rat | brain cDNA | H-Ala-Cys-Phe-Trp-Lys-Tyr-Cys-Val-OH (SEQ ID NO: 33) |
| Horse | predicted | H-Ala-Cys-Phe-Trp-Lys-Tyr-Cys-Val-OH (SEQ ID NO: 34) |
| Chimpanzee | predicted | H-Ala-Cys-Phe-Trp-Lys-Tyr-Cys-Val-OH (SEQ ID NO: 35) |
| Human | brain cDNA | H-Ala-Cys-Phe-Trp-Lys-Tyr-Cys-Val-OH (SEQ ID NO: 36) |

Although sharing the same intracyclic core sequence, previous SAR studies have highlighted differences in their recognition and activation process. Indeed, inversion of the configuration of the Trp residue in UII, hUII(4-11), the smallest hUII equiactive fragment, or URP demonstrated a differential participative effect of this residue in these structures.[9] Introduced in hUII or hUII(4-11), it produced weak agonists, whereas the same substitution in URP produced a partial agonist that is able to completely abolished the UII-induced aortic ring contraction. Such surprising behaviour was also observed when the phenylalanine moiety is replaced with a cyclohexylalanine residue since this substitution generated an antagonist when inserted in the hUII(4-11) sequence but a full agonist in URP.

UII- and URP-associated actions are mediated by the activation of a specific G protein-coupled receptor, UT, which plays a seminal role in the physiological regulation of major mammalian organ systems, including the cardiovascular system.[2] As a matter of fact, urotensin II exerts potent haemodynamic effects[10], positive inotropic and chronotropic responses[11] and osmoregulatory actions[12], induces collagen and fibronectin accumulation[13,14], modulates the inflammatory response[15], plays a role in the induction of cardiac and vascular hypertrophy[16], causes a strong angiogenic effect[17], and inhibits glucose-induced insulin release[18]. Thus, the urotensinergic system has been linked to numerous pathophysiological states including atherosclerosis, heart failure, hypertension, pre-eclampsia, diabetes, renal and liver disease, variceal bleeding, ulcers, and psychological and neurological disorders.[1]

Recent evidence suggested that UII and its paralog peptide URP might exert common but also divergent physiological actions.[19,20] For instance, studies have reported a differential action for these two peptides on cell proliferation[19], and distinctive myocardial contractile activities[20]. In isolated ischaemic heart experiments, both peptides were able to reduce myocardial injury through creatine kinase (CK) reduction but only UII was able to reduce atrial natriuretic peptide (ANP) production.[20] Moreover, UII, but not URP, exerted a dose-dependent mitogenic activity on astrocytes. More recently, a differential transcriptional modulation upon UII or URP activation was observed in isolated heart nuclei.[21] Moreover, distinct pathophysiological roles for UII and URP in hypertension have been suggested.[22] Indeed, the mRNA expression of both UII and URP were up-regulated in the atrium of SHR rats when compared with age-matched WKY rats. However, the specific up-regulation of URP but not UII mRNA in aorta and kidney of SHR rats supports the idea that these peptides may act individually in this biological system.[22] Key questions remain regarding the specific role associated with each peptide in this system.

Over the past decade, development of non-peptide UT antagonists has allowed investigators to begin to delineate the (patho)physiological roles of the UII/UT system.[23] However, none of the existing antagonists (peptidic and non-peptidic) was designed to discriminate specific UII- or URP-associated actions.

The present specification refers to a number of documents, the content of which is herein incorporated in their entirety.

SUMMARY

The present specification broadly relates to novel urotensin II receptor (UT) agonists and antagonists. In an embodiment, the present disclosure relates to novel derivatives of urotensin II-related peptide (URP). In a further embodiment, the present disclosure relates to a biphenylalanine urotensin II-related peptide ([Bip⁴]URP).

In an embodiment, the present disclosure relates to a urotensinergic agent or a pharmaceutically acceptable salt thereof having the formula:

(SEQ ID NO: 37)

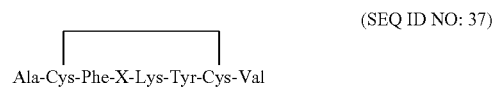

Ala-Cys-Phe-X-Lys-Tyr-Cys-Val wherein X is a L- or D-amino acid selected from the group consisting of glycine, alanine, serine, threonine, cysteine, valine, leucine, isoleucine, methionine, proline, phenylalanine, tyrosine, tryptophan, aspartic acid, glutamic acid, Asparagine, glutamine, histidine, lysine, arginine and side-chain conformationally restricted phenylalanines including β-β-diphenylalanine; 1,2,3,4-terahydroisoquinoline-3-carboxylic acid, tetrahydroisoquinoline-1-carboxylic acid; 1,2,3,4-tetrahydronorharman-3-carboxylic acid and 4-amino-indolo[2,3-c]azepin-3-one, or a phenylalanine analogue having the formula:

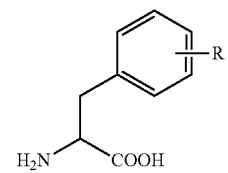

wherein R is a substituent introduced by metal catalysed reaction using a boronic acid, a boronic acid derivative, a substituted vinyl, or a substituted alkynyl.

In an embodiment, the present disclosure relates to a urotensinergic agent or a pharmaceutically acceptable salt thereof having the formula:

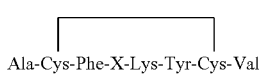

(SEQ ID NO: 37)

Ala-Cys-Phe-X-Lys-Tyr-Cys-Val wherein X is a L- or D-amino acid selected from the group consisting of glycine, alanine, serine, threonine, cysteine, valine, leucine, isoleucine, methionine, proline, phenylalanine, tyrosine, tryptophan, aspartic acid, glutamic acid, asparagine, glutamine, histidine, lysine, arginine and side-chain conformationally restricted phenylalanines including β-β-diphenylalanine; 1,2,3,4-terahydroisoquinoline-3-carboxylic acid, tetrahydroisoquinoline-1-carboxylic acid; 1,2,3,4-tetrahydronorharman-3-carboxylic acid and 4-amino-indolo[2,3-c]azepin-3-one, or a phenylalanine analogue having the formula:

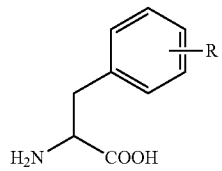

wherein R is a substituent introduced by metal catalysed reaction using a boronic acid or a boronic acid derivative selected from the group consisting of phenylboronic acid, 4-hydroxyphenylboronic acid, 4-methoxycarbonylphenylboronic acid, 4-pyridineboronic acid, 4-cyanophenylboronic acid, 4-(hydroxymethyl)phenylboronic acid, 3-furanboronic acid, 2-furanboronic acid, 3-thiophenboronic acid, 3-nitrophenylboronic acid, trans-2-chloromethylvinylboronic acid, trans-1-propen-1-ylboronic acid, 2-Boc-indoleboronic acid, acetamidophenylboronic acid, 4-(N-Boc-amino)phenylboronic acid, 4-phenoxyphenylboronic acid, 4-acetylphenylboronic acid and 2,4,6-trifluorophenylboronic acid; a substituted vinyl selected from the group consisting of vinylbenzene, 1-methyl-4-vinylbenzene, 1-methyl-3-vinylbenzene, 1-methyl-2-vinylbenzene, 1,3,5-trimethyl-2-vinylbenzene, 1-vinylnaphthalene, 2-vinylnaphthalene, 1-isopropyl-4-vinylbenzene, 1-(chloromethyl)-4-vinylbenzene, 1-chloro-4-vinylbenzene, 3-vinylbenzene, 4-vinylbenzoic acid, 1-(trifluoromethyl)-2-vinylbenzene, 1-(trifluoromethyl)-4-vinylbenzene, 1-(trifluoromethyl)-3-vinylbenzene, isopropenylbenzene, 4-nitrostyrene, 4-vinylalanine, 4-vinylanisole, 1-tert-butoxy-4-vinylbenzene, 4-vinylphenyl acetate and 1-ethoxy-4-vinylbenzene, or a substituted alkynyl selected from the group consisting of ethynylbenzene, 1-ethynyl-4-fluorobenzene, 1-ethynyl-4-tert-butylbenzene, 1-ethynyl-4-methoxy-2-methylbenzene, ethynylcyclohexane, 1-decyne, 9-ethynylphenanthrene, 1-ethynylnaphthalene, 4-ethynylbenzonitrile, 1-ethynyl-4-(trifluoromethyl)benzene, 4-ethynylaniline, 4-ethynyl-1,1'-biphenyl.

In an embodiment, the present disclosure relates to a urotensinergic agent or a pharmaceutically acceptable salt thereof having the formula:

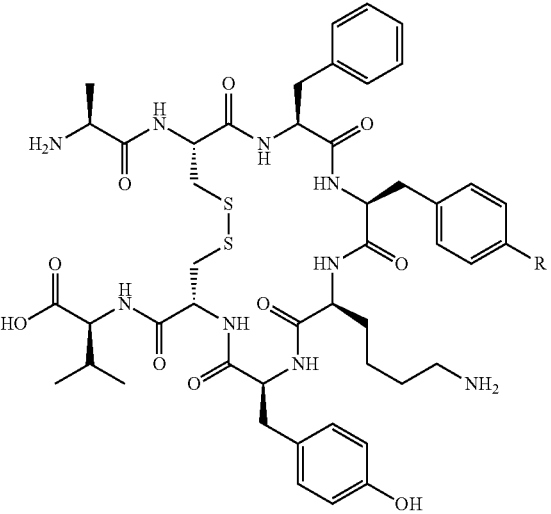

wherein R is a substituent introduced by metal catalysed reaction using a boronic acid or a boronic acid derivative selected from the group consisting of phenylboronic acid, 4-hydroxyphenylboronic acid, 4-methoxycarbonylphenylboronic acid, 4-pyridineboronic acid, 4-cyanophenylboronic acid, 4-(hydroxymethyl)phenylboronic acid, 3-furanboronic acid, 2-furanboronic acid, 3-thiophenboronic acid, 3-nitrophenylboronic acid, trans-2-chloromethylvinylboronic acid, trans-1-propen-1-ylboronic acid, 2-Boc-indoleboronic acid, acetamidophenylboronic acid, 4-(N-Boc-amino)phenylboronic acid, 4-phenoxyphenylboronic acid, 4-acetylphenylboronic acid and 2,4,6-trifluorophenylboronic acid.

In an embodiment, the present disclosure relates to a urotensinergic agent or a pharmaceutically acceptable salt thereof having the formula:

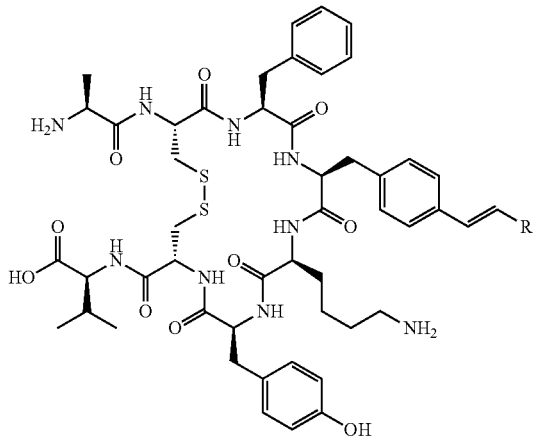

wherein the substituted vinyl (R—C═C—) is introduced by metal catalysed reaction using a substituted vinyl selected from the group consisting of vinylbenzene, 1-methyl-4-vinylbenzene, 1-methyl-3-vinylbenzene, 1-methyl-2-vinylbenzene, 1,3,5-trim ethyl-2-vinylbenzene, 1-vinylnaphthalene, 2-vinylnaphthalene, 1-isopropyl-4-vinylbenzene, 1-(chloromethyl)-4-vinylbenzene, 1-chloro-4-vinylbenzene, 3-vinylbenzene, 4-vinylbenzoic acid, 1-(trifluoromethyl)-2-vinylbenzene, 1-(trifluoromethyl)-4-vinylbenzene, 1-(trifluoromethyl)-3-vinylbenzene, isopropenylbenzene, 4-nitrostyrene, 4-vinylalanine, 4-vinylanisole, 1-tert-butoxy-4-vinylbenzene, 4-vinylphenyl acetate and 1-ethoxy-4-vinylbenzene.

In an embodiment, the present disclosure relates to a urotensinergic agent or a pharmaceutically acceptable salt thereof having the formula:

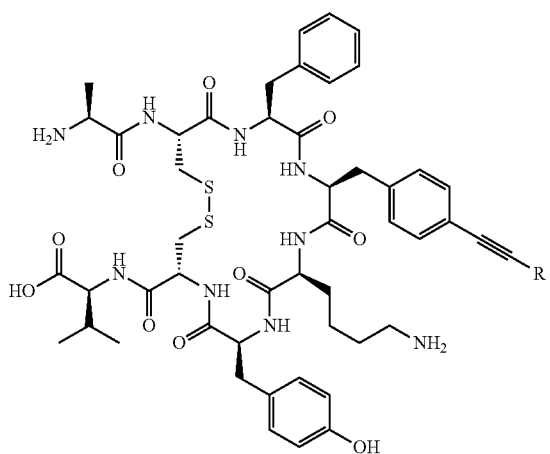

wherein the substituted alkynyl (R—C≡C—) is introduced by metal catalysed reaction using a substituted alkynyl selected from the group consisting of ethynylbenzene, 1-ethynyl-4-fluorobenzene, 1-ethynyl-4-tert-butylbenzene, 1-ethynyl-4-m ethoxy-2-m ethylbenzene, ethynylcyclohexane, 1-decyne, 9-ethynylphenanthrene, 1-ethynylnaphthalene, 4-ethynylbenzonitrile, 1-ethynyl-4-(trifluoromethyl)benzene, 4-ethynylaniline, 4-ethynyl-1,1'-biphenyl.

In an embodiment, the present disclosure relates to a radiolabelled urotensinergic agent having the formula:

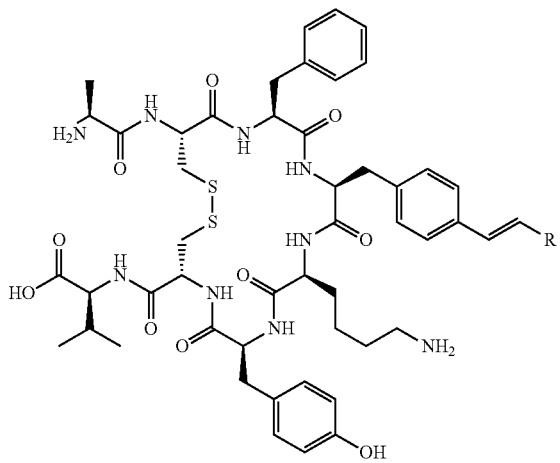

wherein R is a substituent introduced by metal catalysed reaction using a boronic acid or a boronic acid derivative selected from the group consisting of phenylboronic acid, 4-hydroxyphenylboronic acid, 4-methoxycarbonylphenylboronic acid, 4-pyridineboronic acid, 4-cyanophenylboronic acid, 4-(hydroxymethyl)phenylboronic acid, 3-furanboronic acid, 2-furanboronic acid, 3-thiophenboronic acid, 3-nitrophenylboronic acid, trans-2-chloromethylvinylboronic acid, trans-1-propen-1-ylboronic acid, 2-Boc-indoleboronic acid, acetamidophenylboronic acid, 4-(N-Boc-amino)phenylboronic acid, 4-phenoxyphenylboronic acid, 4-acetylphenylboronic acid and 2,4,6-trifluorophenylboronic acid; and wherein Z is a ligand comprising a radioisotope.

In a more specific embodiment the radioisotope is selected from the group consisting of $I^{123}$, $I^{125}$, $I^{131}$, $^{99m}Tc$, $^{161}Tb$, $^{177}Lu$, $^{18}F$, $^{68}Ga$, $^{62}Cu$, $^{111}In$, $^{186}Re$, $^{188}Re$, $^{90}Y$, $^{212}Bi$, $^{211}At$, $^{89}Sr$, $^{166}Ho$, $^{153}Sm$, $^{67}Cu$, $^{64}Cu$ and $Br^{76}$.

In an embodiment, the present disclosure relates to a radiolabelled urotensinergic agent having the formula:

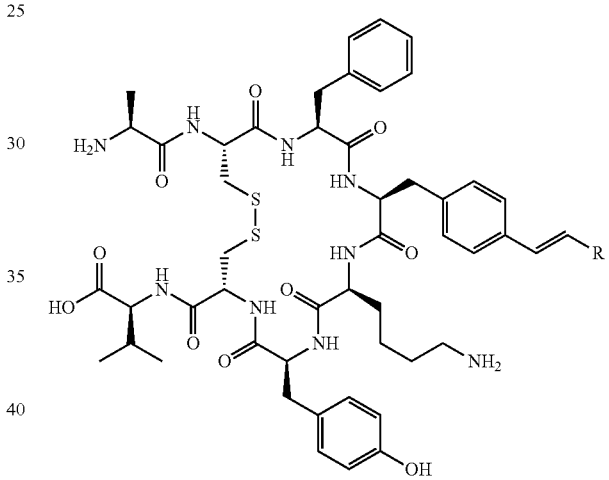

wherein the substituted vinyl (R—C=C—) is introduced by metal catalysed reaction using a substituted vinyl selected from the group consisting of vinylbenzene, 1-methyl-4-vinylbenzene, 1-methyl-3-vinylbenzene, 1-methyl-2-vinylbenzene, 1,3,5-trim ethyl-2-vinylbenzene, 1-vinylnaphthalene, 2-vinylnaphthalene, 1-isopropyl-4-vinylbenzene, 1-(chloromethyl)-4-vinylbenzene, 1-chloro-4-vinylbenzene, 3-vinylbenzene, 4-vinylbenzoic acid, 1-(trifluoromethyl)-2-vinylbenzene, 1-(trifluoromethyl)-4-vinylbenzene, 1-(trifluoromethyl)-3-vinylbenzene, isopropenylbenzene, 4-nitrostyrene, 4-vinylalanine, 4-vinylanisole, 1-tert-butoxy-4-vinylbenzene, 4-vinylphenyl acetate and 1-ethoxy-4-vinylbenzene; and wherein Z is a ligand comprising a radioisotope.

In a more specific embodiment the radioisotope is selected from the group consisting of $I^{123}$, $I^{125}$, $I^{131}$, $^{99m}Tc$, $^{161}Tb$, $^{177}Lu$, $^{18}F$, $^{68}Ga$, $^{62}Cu$, $^{111}In$, $^{186}Re$, $^{188}Re$, $^{90}Y$, $^{212}Bi$, $^{211}At$, $^{89}Sr$, $^{166}Ho$, $^{153}Sm$, $^{67}Cu$, $^{64}Cu$ and $Br^{76}$.

In an embodiment, the present disclosure relates to a radiolabelled urotensinergic agent having the formula:

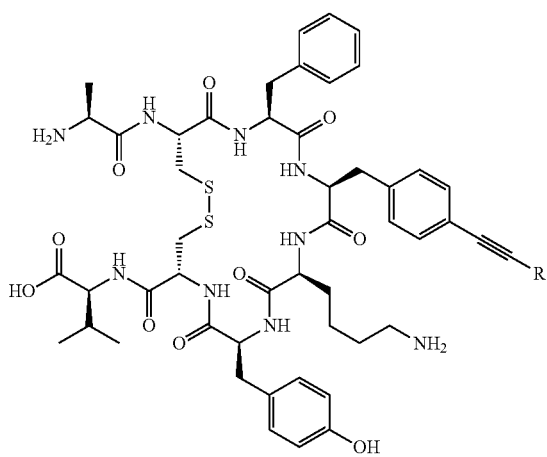

wherein the substituted alkynyl (R—C≡C—) is introduced by metal catalysed reaction using a substituted alkynyl selected from the group consisting of ethynylbenzene, 1-ethynyl-4-fluorobenzene, 1-ethynyl-4-tert-butylbenzene, 1-ethynyl-4-methoxy-2-methylbenzene, ethynylcyclohexane, 1-decyne, 9-ethynylphenanthrene, 1-ethynylnaphthalene, 4-ethynylbenzonitrile, 1-ethynyl-4-(trifluoromethyl) benzene, 4-ethynylaniline, 4-ethynyl-1,1'-biphenyl; and wherein Z is a ligand comprising a radioisotope.

In a more specific embodiment the radioisotope is selected from the group consisting of $I^{123}$, $I^{125}$, $I^{131}$, $^{99m}Tc$, $^{161}Tb$, $^{177}Lu$, $^{18}F$, $^{68}Ga$, $^{62}Cu$, $^{111}In$, $^{186}Re$, $^{188}Re$, $^{90}Y$, $^{212}Bi$, $^{211}At$, $^{89}Sr$, $^{166}Ho$, $^{153}Sm$, $^{67}Cu$, $^{64}Cu$ and $Br^{76}$ In another embodiment, the ligand is located in any suitable position on the peptide core providing for additional radiolabelled derivatives. In yet another embodiment, the radioisotope is located in any suitable position on the peptide core providing for additional radiolabelled derivatives. Further non-limiting examples of suitable positions comprise the Tyr moiety and the Phe moiety. Yet furthermore, the aromatic portion of either the Phe or Tyr moiety provide for suitable locations for the introduction of one or more ligands and/or radioisotopes. In an embodiment, at least one ligand or radioisotope is located on the peptide core. The radiolabelled derivatives are useful for radioimaging and/or radiotherapeutic treatment of various pathologies including cancer and cardiovascular diseases. Indeed, the dramatic overexpression of the UT receptor in a variety of different pathological states (e.g. cancer, atherosclerosis and diabetic nephropathy) suggests that these agents could represent novel radioimaging and/or theragnostic agents.

In an embodiment of the present disclosure, the N-terminus of the alanine moiety may be modified by the addition of complexing or conjugating agents providing for the integration of a radioisotope. For clarity, when the ligand is positioned at the N-terminus of the alanine moiety, it is understood that the ligand comprises a complexing or conjugating agent and a radioisotope. Non-limiting examples of such complexing or conjugating agents include DOTA- and DTPA-based chelators, NOTA-based chelators, carbonyl compounds, 2-hydrazino nicotinamide (HYNIC), $N_4$-chelators, desferrioxamin and $N_xS_y$-chelators. It is understood that such modifications to the N-terminus do not significantly affect the binding affinity of the agent.

In an embodiment, the present disclosure relates to a urotensinergic agent or a pharmaceutically acceptable salt thereof, wherein the agent substantially includes the N-terminal segment of one of the UII isoforms. In an embodiment of the present disclosure, the agent is selected from N-terminal segments selected from the group consisting of lamprey (Asn-Asn-Phe-Ser-Asp) (SEQ ID NO: 38), fugu (Thr-Gly-Asn-Asn-Glu) (SEQ ID NO: 39), skate (Asn-Asn-Phe-Ser-Asp) (SEQ ID NO: 40), dogfish (Asn-Asn-Phe-Ser-Asp) (SEQ ID NO: 41), sturgeon (Gly-Ser-Thr-Ser-Glu) (SEQ ID NO: 42), paddlefish (Gly-Ser-Thr-Ser-Glu) (SEQ ID NO: 43), goby (Ala-Gly-Thr-Ala-Asp) (SEQ ID NO: 44), zebrafish α (Gly-Gly-Gly-Ala-Asp) (SEQ ID NO: 45), zebrafish β (Gly-Ser-Asn-Thr-Glu) (SEQ ID NO: 46), sucker A (Gly-Ser-Gly-Ala-Asp) (SEQ ID NO: 47), sucker B (Gly-Ser-Asn-Thr-Glu) (SEQ ID NO: 48), carp α (Gly-Gly-Gly-Ala-Asp) (SEQ ID NO: 49), carp β1 (Gly-Gly-Asn-Thr-Glu) (SEQ ID NO: 50), carp β2 (Gly-Ser-Asn-Thr-Glu) (SEQ ID NO: 51), carp γ (Gly-Gly-Gly-Ala-Asp) (SEQ ID NO: 52), flounder (Ala-Gly-Thr-Thr-Glu) (SEQ ID NO: 53), trout (Gly-Gly-Asn-Ser-Glu) (SEQ ID NO: 54), grouper (Ala-Gly-Asn-Ser-Glu) (SEQ ID NO: 55), frog (Ala-Gly-Asn-Leu-Ser-Glu) (SEQ ID NO: 56), chicken (Gly-Asn-Leu-Ser-Glu) (SEQ ID NO: 57), zebra finch (Gly-Asn-Leu-Ser-Glu) (SEQ ID NO: 58), mouse (Pyr-His-Lys-Gln-His-Gly-Ala-Ala-Pro-Glu) (SEQ ID NO: 59), rat (Pyr-His-Gly-Thr-Ala-Pro-Glu) (SEQ ID NO: 60), porcine A (Gly-Pro-Thr-Ser-Glu) (SEQ ID NO: 61), porcine B (Gly-Pro-Pro-Ser-Glu) (SEQ ID NO: 62), cattle (Gly-Pro-Ser-Ser-Glu) (SEQ ID NO: 63), monkey (Glu-Thr-Pro-Asp) (SEQ ID NO: 64), chimpanzee (Glu-Thr-Pro-Asp) (SEQ ID NO: 65) and human (Glu-Thr-Pro-Asp) (SEQ ID NO: 66) UII isoforms. In a more specific embodiment of the present disclosure, the agent is based on the rUII isoform and has the formula:

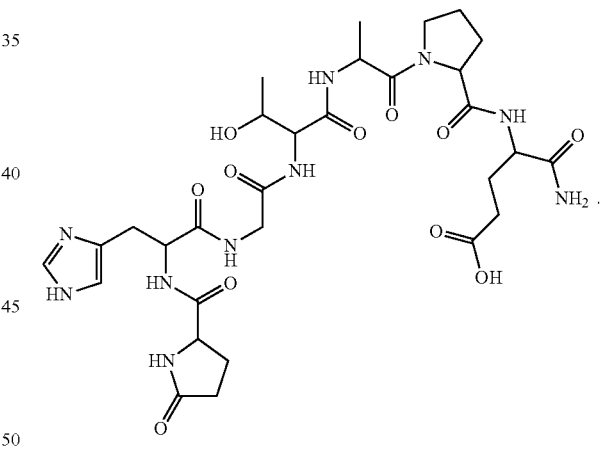

In an embodiment, the present disclosure relates to antagonists for modulating UT activity.

In an embodiment, the present disclosure relates to agonists for modulating UT activity.

In an embodiment, the present disclosure relates to antagonists for discriminating between specific UII- or URP-associated actions.

In an embodiment, the present disclosure relates to agonists of the urotensinergic system.

In an embodiment, the present disclosure relates to constrained agonists of the urotensinergic system.

In an embodiment, the present disclosure relates to antagonists of the urotensinergic system.

In an embodiment, the present disclosure relates to a method for discriminating between specific biological action mediated by UII and/or URP comprising the steps of: i)

exposing aortic rings to a urotensinergic agent as disclosed herein; ii) preparing concentration-response curves to UII or URP; and iii) evaluating the effect of the urotensinergic agent on aortic ring contraction induced by either UII or URP.

The foregoing and other objects, advantages and features of the present specification will become more apparent upon reading of the following non-restrictive description of illustrative embodiments thereof, given by way of example only with reference to the accompanying drawings.

BRIEF DESCRIPTION OF THE DRAWINGS

In the appended drawings:

In FIG. 7A, repeated injections of hUII produced equivalent biphasic responses suggesting a no tolerance effect for hUII. In FIG. 7B, the complete absence of response following a second hUII injection, when rats were pre-treated with [Bip$^4$] URP (1000 nmol/kg), is worth mentioning.

DETAILED DESCRIPTION

Figure 1:
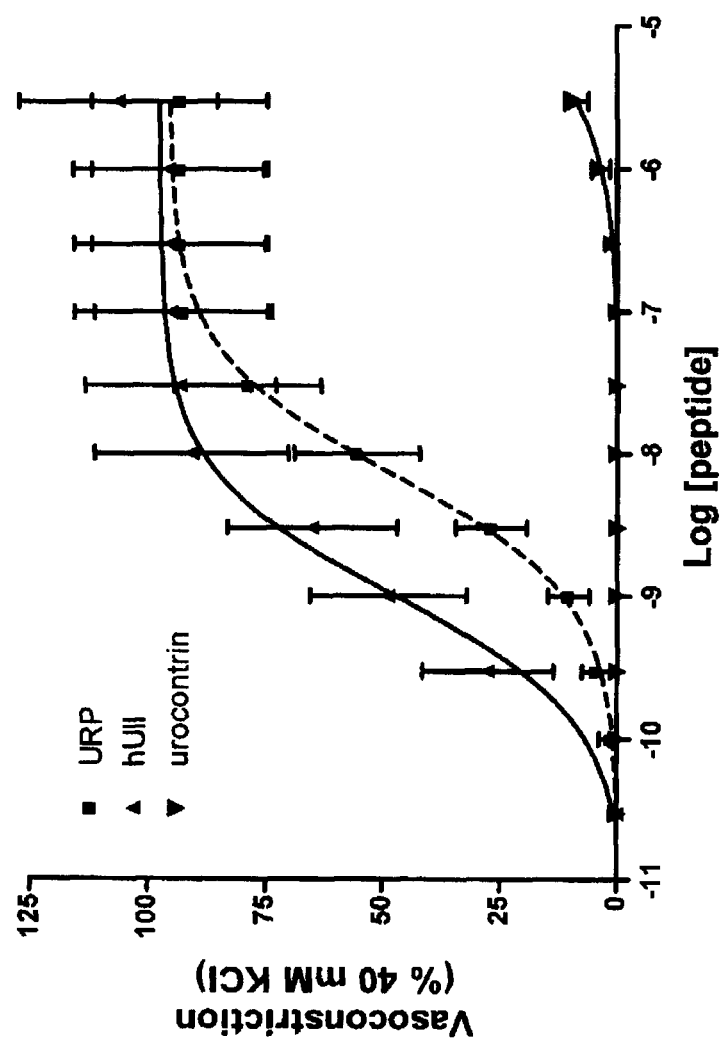
FIG. 1 is an illustration of representative concentration-response curves obtained with rat thoracic aorta rings after adding cumulative concentrations of hUII, URP and [Bip$^4$] URP (i.e. urocontrin). Exposure to increasing concentrations of [Bip$^4$]URP up to 3 μM induced only a weak vasoconstriction ($E_{max}$=8.7% at $10^{-5.5}$ M). Data represent the mean±S.E.M. and n=5 to 10 animals.

In order to provide a clear and consistent understanding of the terms used in the present specification, a number of definitions are provided below. Moreover, unless defined otherwise, all technical and scientific terms as used herein have the same meaning as commonly understood by one of ordinary skill in the art to which this specification pertains.

The use of the word "a" or "an" when used in conjunction with the term "comprising" in the claims and/or the specification may mean "one", but it is also consistent with the meaning of one or more", at least one", and "one or more than one". Similarly, the word "another" may mean at least a second or more.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The present description refers to a number of chemical terms and abbreviations used by those skilled in the art. Nevertheless, definitions of selected terms are provided for clarity and consistency.

ABBREVIATIONS

NMR: Nuclear Magnetic Resonance; MS: Mass Spectrometry; All optically active amino acids are of the L configuration unless stated otherwise; Cha: cyclohexylalanine; Dip: β,β-diphenylalanine; Tic: 1,2,3,4,-tetrahydroisoquinoline-3-carboxylic acid; Tiq: tetrahydroisoquinoline-1-carboxylic acid; Tpi: L-1,2,3,4-tetrahydronorharman-3-carboxylic acid; Aia: 4-amino-indolo[2,3-c]azepin-3-one; Tbg: tert-butyl-glycine; Phg: phenylglycine; Pen: β,β-dimethyl-cysteine; Orn: ornithine.

As used herein, the term "alkyl" can be straight-chain or branched. This also applies if they carry substituents or occur as substituents on other residues, for example in alkoxy residues, alkoxycarbonyl residues or arylalkyl residues. Substituted alkyl residues can be substituted at any suitable position(s). Examples of alkyl residues containing from 1 to 18 carbon atoms are methyl, ethyl, propyl, butyl, pentyl, hexyl, heptyl, octyl, nonyl, decyl, undecyl, dodecyl, tetradecyl, hexadecyl and octadecyl, as well as the branched analogs of all these residues, such as isopropyl, isobutyl, isopentyl, neopentyl, isohexyl, isodecyl, 3-methylpentyl, 2,3,4-trimethylhexyl, sec-butyl, tert-butyl, or tert-pentyl. A specific group of alkyl residues is formed by the residues methyl, ethyl, n-propyl, isopropyl, n-butyl, isobutyl, sec-butyl and tert-butyl.

As used herein, the term "lower alkyl" can be straight-chain or branched. This also applies if they carry substituents or occur as substituents on other residues, for example in alkoxy residues, alkoxycarbonyl residues or arylalkyl residues. Substituted alkyl residues can be substituted in any suitable position. Examples of lower alkyl residues containing from 1 to 6 carbon atoms are methyl, ethyl, propyl, isopropyl, butyl, isobutyl, tert-butyl, pentyl, isopentyl, neopentyl, and hexyl.

As used herein, the term "ligand" refers to a moiety that is capable of generating a detectable image that may be detected by using an appropriate visualization technique, e.g. positron emission tomography (PET), single photon emission tomography (SPECT) or magnetic resonance imaging (MRI). Certain exemplary radioisotopes are radionuclides, or radioactive isotopes of an element. Non-limiting examples of radionuclides include $I^{123}$, $^{99m}Tc$, $^{18}F$, $^{68}Ga$, $^{62}Cu$, $^{111}In$, $^{131}I$, $^{186}Re$, $^{188}Re$, $^{90}Y$, $^{212}Bi$, $^{211}At$, $^{89}Sr$, $^{166}Ho$, $^{153}Sm$, $^{67}Cu$, $^{64}Cu$ and $^{76}Br$. Additional radioisotopes are suitable for obtaining a magnetic resonance image (MRI), including unpaired spin atoms and free radicals (e.g. iron, lanthanides and gadolinium) and contrast agents (e.g. DTPA chelated manganese).

As used herein, the term "conformationally constrained" means that at least one of a rotational or translational degree of freedom is reduced or eliminated from the agonist or antagonist. Consequently, conformationally constrained agonists or antagonists may be locked in a particular conformation or may have one or more substituents confined to a particular conformation and/or position with respect to the remainder of the agonists or antagonists. In an embodiment, conformational constraints are induced by the introduction of cyclic moieties.

The term "pharmaceutically acceptable" means compatible with the treatment of subjects, in particular humans.

The term "pharmaceutically acceptable salt" means an acid addition salt or a base addition salt which is suitable for, or compatible with, the treatment of subjects.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The term "substituted" as used in the term "substituted vinyl" and substituted alkynyl" signifies that at least one substituent may be present on the vinyl or alkynyl and is contemplated to include all permissible substituents of organic compounds. Substituents include alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogen, aralkyl, alkenyl, alkynyl, aryl, carboxyalkoxy, carboxyalkyl, cycloalkyl, cycloalkylalkyl, heterocyclyl, alkylheterocyclyl, heterocyclylalkyl. The aforementioned groups, where possible, may be optionally further substituted. Illustrative substituents include, for example, those described herein below in Tables 3 and 4.

An acid addition salt which is suitable for, or compatible with, the treatment of subjects as used herein means any non-toxic organic or inorganic salt of any basic compound. Basic compounds that form an acid addition salt include, for example, compounds comprising an amine group. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, acid addition salts are more soluble in water and various hydrophilic organic solvents, and generally demonstrate higher melting points in comparison to their free base forms. The selection of the appropriate salt will be known to one skilled in the art.

A base addition salt which is suitable for, or compatible with, the treatment of subjects as used herein means any non-toxic organic or inorganic base addition salt of any acidic compound. Acidic compounds that form a base addition salt include, for example, compounds comprising a carboxylic acid group. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline, alkylammonias or ammonia. The selection of the appropriate salt will be known to a person skilled in the art.

The formation of a desired compound salt is achieved using standard techniques. For example, the neutral compound is treated with an acid or base in a suitable solvent and the formed salt is isolated by filtration, extraction or any other suitable method.

The peptides and polypeptides of the present disclosure may be synthesized using commercially available peptide synthesizers. For example, the chemical methods described in Kaumaya et al. (1994), "DE NOVO" ENGINEERING OF PEPTIDE IMMUNOGENIC AND ANTIGENIC DETERMINANTS AS POTENTIAL, VACCINES, in Peptides, Design, Synthesis and Biological Activity (1994), pp. 133-164, which is specifically incorporated herein by reference, may be used. For example, the first peptide portion may be synthesized in tandem with the one or more second peptide portions to form a polypeptide. Peptoids would be synthesized by modifications of the chemistry on similar equipment.

In yet another embodiment, the peptides or polypeptides of the present application are linked to a solid support. The solid support is one which facilitates isolation of the peptides or polypeptides, and any complexes formed with the peptides or polypeptides, from a mixture. Solid supports may include but are not restricted to microscopic beads (e.g. magnetic or chemically activated) or any materials used for the preparation of microarrays, microfluidic devices or titre plate based high volume analysis. Examples of such supports include, for example, polystyrene resins, polyamide resins, polyethylene glycol (PEG)-hybrid polystyrene resins, PEG resins and Dynal™ magnetic beads. Methods for coupling peptides to solid supports are well known in the art.

During the course of structure-activity relationship studies on URP derivatives, a novel UT receptor ligand was identified. More specifically, [Bip$^4$]URP [i.e. urocontrin] was identified and its in vitro and in vivo pharmacological profile established. One striking result is the ability of this analog to reduce the efficacy of hUII- but not URP-induced vasoconstriction. Based on this atypic behaviour, the presence of specific peptide-receptor interactions responsible for hUII- and URP-mediated action was investigated and it was discovered that the N-terminal region of UII isoforms could serve as a selective competitive URP antagonists.

The urotensinergic agents of the present disclosure were prepared as illustrated hereinbelow in Scheme 1).

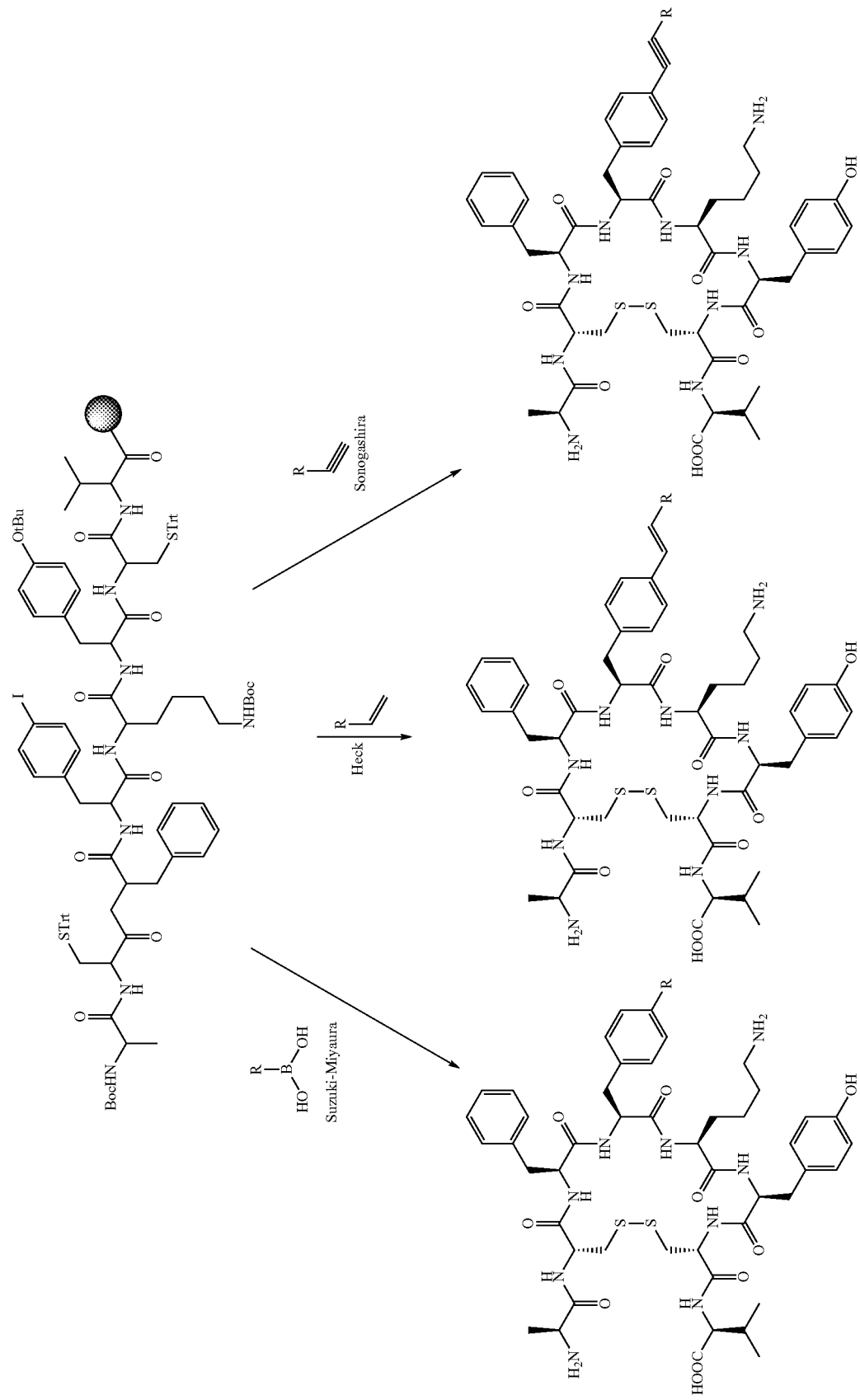
Scheme 1: Synthetic route to urotensinergic agents

In the case of the Suzuki-Miyaura reaction, the boronic acids illustrated hereinbelow in Table 2 were used as substrates for coupling with the peptide. It is understood that these boronic acids are non-limiting examples and that other boronic acids can be used without undue experimentation in light of the present disclosure.

TABLE 2

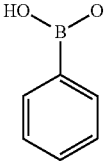

phenylboronic acid

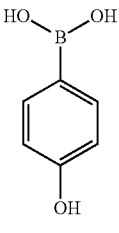

4-Hydroxy-phenylboronic acid

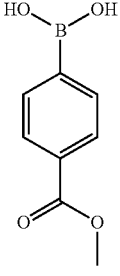

4-methoxycarbonyl-phenylboronic acid

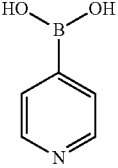

4-Pyridineboronic acid

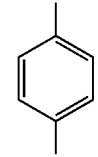

4-Cyanophenylboronic acid

TABLE 2-continued

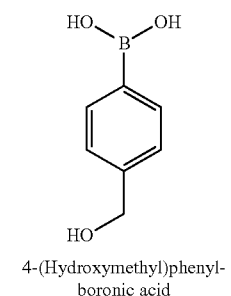 [SMILES: OCc1ccc(B(O)O)cc1]

4-(Hydroxymethyl)phenyl-boronic acid

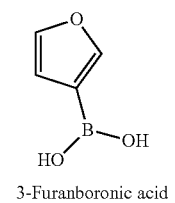

3-Furanboronic acid

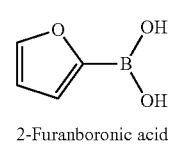

2-Furanboronic acid

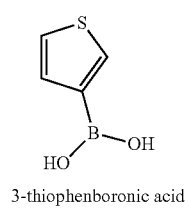

3-thiophenboronic acid

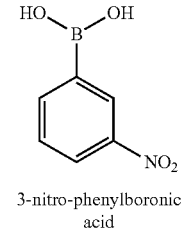

3-nitro-phenylboronic acid

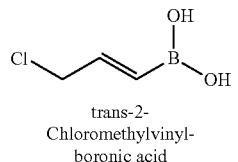

trans-2-Chloromethylvinyl-boronic acid

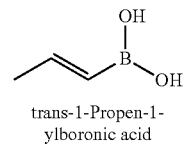

trans-1-Propen-1-ylboronic acid

TABLE 2-continued

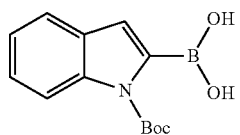

1-Boc-5-bromoindole-2-
boronic acid

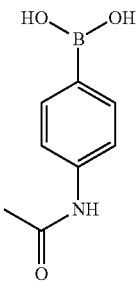

4-Acetamidophenylboronic
acid

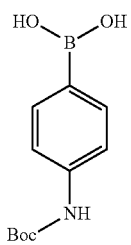

4-(N-Boc-
amino)phenylboronic
acid

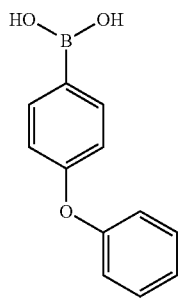

4-Phenoxyphenylboronic
acid

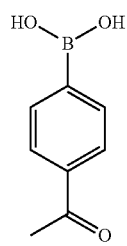

4-Acetylphenylboronic
acid

TABLE 2-continued

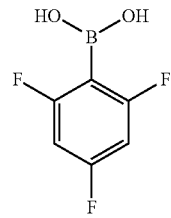

2,4,6-
Trifluorophenylboronic
acid

In the case of the Heck reaction, the substituted vinyl substrates illustrated hereinbelow in Table 3 were used for coupling with the peptide. It is understood that these substituted vinyl substrates are non-limiting examples and that other substituted vinyl substrates can be used without undue experimentation in light of the present disclosure.

TABLE 3

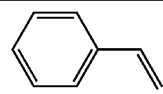

vinylbenzene

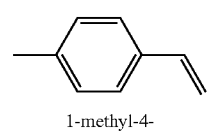

1-methyl-4-
vinylbenzene

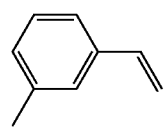

1-methyl-3-
vinylbenzene

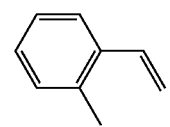

1-methyl-2-vinylbenzene

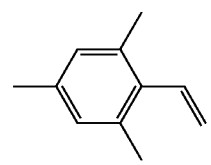

1,3,5-trimethyl-2-
vinylbenzene

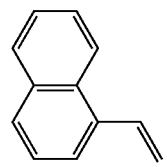

1-vinylnaphthalene

TABLE 3-continued

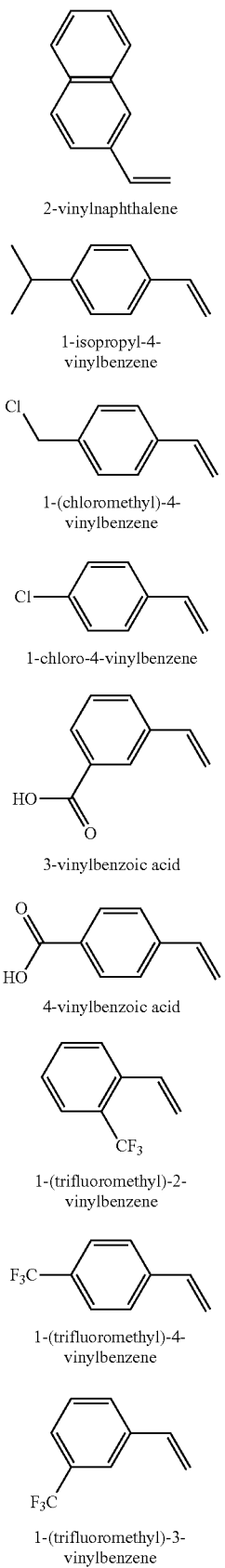

2-vinylnaphthalene 1-isopropyl-4-vinylbenzene 1-(chloromethyl)-4-vinylbenzene 1-chloro-4-vinylbenzene 3-vinylbenzoic acid 4-vinylbenzoic acid 1-(trifluoromethyl)-2-vinylbenzene 1-(trifluoromethyl)-4-vinylbenzene 1-(trifluoromethyl)-3-vinylbenzene

TABLE 3-continued

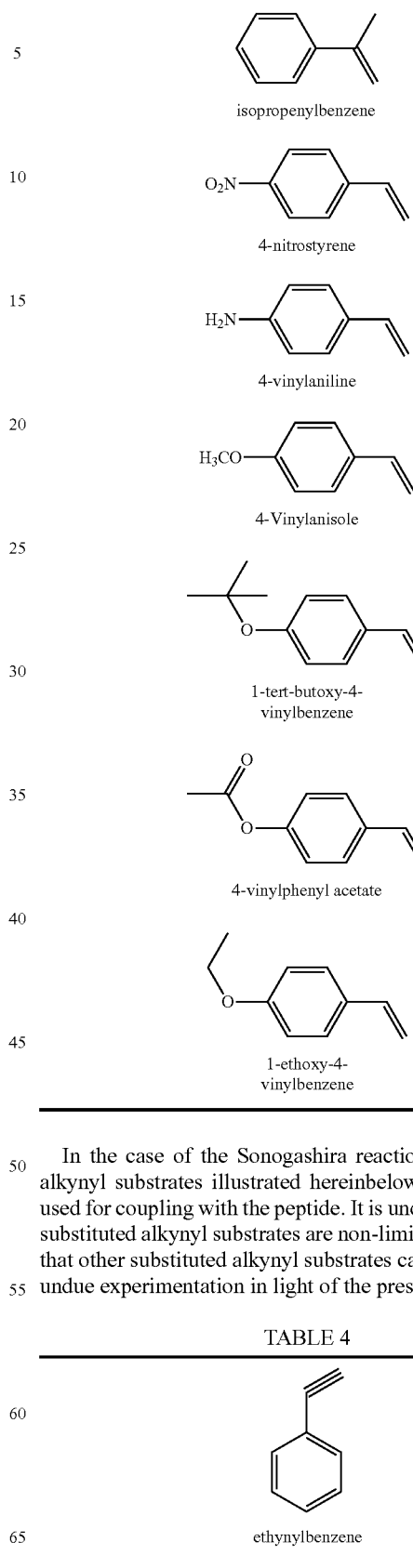

isopropenylbenzene 4-nitrostyrene 4-vinylaniline

4-Vinylanisole 1-tert-butoxy-4-vinylbenzene 4-vinylphenyl acetate 1-ethoxy-4-vinylbenzene In the case of the Sonogashira reaction, the substituted alkynyl substrates illustrated hereinbelow in Table 4 were used for coupling with the peptide. It is understood that these substituted alkynyl substrates are non-limiting examples and that other substituted alkynyl substrates can be used without undue experimentation in light of the present disclosure.

TABLE 4

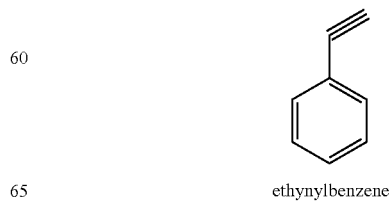

ethynylbenzene

TABLE 4-continued
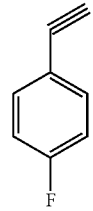
1-ethynyl-4-fluorobenzene
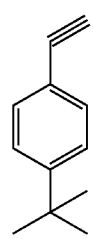
1-ethynyl-4-tert-butylbenzene
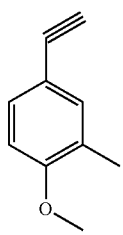
1-ethynyl-4-methoxy-2-methylbenzene
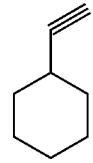
ethynylcyclohexane
1-decyne
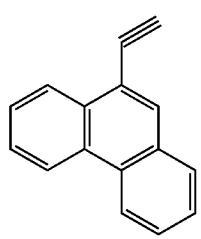
9-ethynylphenanthrene
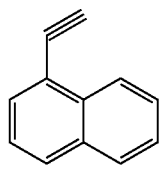
1-ethynylnaphthalene
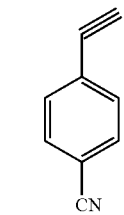
4-ethynylbenzonitrile
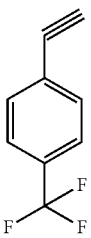
1-ethynyl-4-(trifluoromethyl)benzene
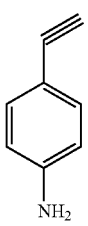
4-ethynylaniline TABLE 4-continued

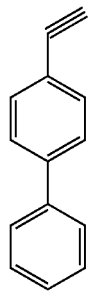

4-ethynyl-1,1'-biphenyl

In an embodiment, the present specification relates to pharmaceutical compositions comprising a pharmaceutically effective amount of one or more of the urotensinergic agents or pharmaceutically acceptable salts thereof, in association with one or more pharmaceutically acceptable carriers, excipients and/or diluents. The term "pharmaceutically effective amount" is understood as being an amount of the urotensinergic agent required upon administration to a mammal in order to induce any measurable antagonistic effect on hUII-associated action. Therapeutic methods comprise the step of treating patients in a pharmaceutically acceptable manner with one or more of the urotensinergic agents or pharmaceutically acceptable salts thereof or compositions comprising same. Such compositions may be in the form of tablets, capsules, caplets, powders, granules, lozenges, suppositories, reconstitutable powders, creams, ointments, lotions, or liquid preparations, such as oral or sterile parenteral solutions or suspensions, transdermal preparations, inhalation powders or solutions, or any other suitable delivery system.

The urotensinergic agents or pharmaceutically acceptable salts thereof may be administered alone or in combination with pharmaceutically acceptable carriers. The proportion of each carrier is determined by the solubility and chemical nature of the agent(s), the route of administration, and standard pharmaceutical practice. In order to ensure consistency of administration, in an embodiment of the present disclosure, the pharmaceutical composition is in the form of a unit dose. The unit dose presentation forms for oral administration may be tablets or capsules and may contain conventional excipients. Non-limiting examples of conventional excipients include binding agents such as acacia, gelatin, sorbitol, or polyvinylpyrrolidone; fillers such as lactose, sugar, maize-starch, calcium phosphate, sorbitol or glycine; tabletting lubricants such as magnesium stearate; disintegrants such as starch, polyvinylpyrrolidone, sodium starch glycolate or microcrystalline cellulose; or pharmaceutically acceptable wetting agents such as sodium lauryl sulphate. Additional excipients include those used in lipid formulations, a non-limiting example of which is olive oil.

The urotensinergic agents or pharmaceutically acceptable salts thereof may be administered alone or in combination with other active compounds, selected in function of the pathological condition(s) to be treated.

The urotensinergic agents or pharmaceutically acceptable salts thereof may be injected parenterally; this being intramuscularly, intravenously, or subcutaneously. For parenteral administration, the urotensinergic agents or pharmaceutically acceptable salts thereof may be used in the form of sterile solutions containing solutes, for example sufficient saline or glucose to make the solution isotonic.

The urotensinergic agents or pharmaceutically acceptable salts thereof may be administered orally in the form of tablets, capsules, or granules, containing suitable excipients such as starch, lactose, sugar and the like. The urotensinergic agents or pharmaceutically acceptable salts thereof may be administered orally in the form of solutions which may contain coloring and/or flavoring agents. The urotensinergic agents or pharmaceutically acceptable salts thereof may also be administered sublingually in the form of comfits or lozenges in which the active ingredient(s) is/are mixed with sugar or corn syrups, flavoring agents and dyes, and then dehydrated sufficiently to make the mixture suitable for pressing into solid form.

The solid oral compositions may be prepared by conventional methods of blending, filling, tabletting, or the like. Repeated blending operations may be used to distribute the active agent(s) (i.e. the urotensinergic agents or pharmaceutically acceptable salts thereof) throughout the compositions, employing large quantities of fillers. Such operations are, of course, conventional in the art. The tablets may be coated according to methods well known in normal pharmaceutical practice, in particular with an enteric coating.

Oral liquid preparations may be in the form of emulsions, syrups, or elixirs, or may be presented as a dry product for reconstitution with water or any other suitable vehicle before use. Such liquid preparations may or may not contain conventional additives. Non limiting examples of conventional additives include suspending agents such as sorbitol, syrup, methyl cellulose, gelatin, hydroxyethylcellulose, carboxymethylcellulose, aluminum stearate gel, or edible fats; emulsifying agents such as sorbitan monooleate or acaci; non-aqueous vehicles (which may include edible oils), such as almond oil, fractionated coconut oil, oily esters selected from the group consisting of glycerine, propylene glycol, ethylene glycol, and ethyl alcohol, as well as preservatives such as methyl para-hydroxybenzoate, ethyl para-hydroxybenzoate, n-propyl para-hydroxybenzoate, n-butyl para-hydroxybenzoate and sorbic acid; and, if desired, conventional flavoring or coloring agents.

For parenteral administration, fluid unit dosage forms may be prepared by utilizing one or more of the urotensinergic agents or pharmaceutically acceptable salts thereof and a sterile vehicle, and, depending on the concentration employed, the urotensinergic agents or pharmaceutically acceptable salts thereof may be either suspended or dissolved in the vehicle. Once in solution, the urotensinergic agent(s) or pharmaceutically acceptable salt(s) thereof may be filter-sterilized before filling a suitable vial or ampoule followed by subsequent sealing of the carrier or storage package or can be directly injected under sterile conditions. Adjuvants, such as a local anesthetic, a preservative or a buffering agent, may be dissolved in the vehicle prior to use. Stability of the pharmaceutical composition may be enhanced by freezing the composition after filling the vial and removing the water under vacuum, (e.g., freeze drying). Parenteral suspensions may be prepared in substantially the same manner, except that the urotensinergic agents or pharmaceutically acceptable salts thereof should be suspended in the vehicle rather than being dissolved. This step must be carried out under sterile conditions. The urotensinergic agents or pharmaceutically acceptable salts thereof may be sterilized by exposing it to ethylene oxide before suspending it in the sterile vehicle. A surfactant or wetting solution may be advantageously included in the composition to facilitate uniform distribution of the urotensinergic agents or pharmaceutically acceptable salts thereof.

Topical administration can be used as the route of administration when local delivery of the urotensinergic agent(s) or pharmaceutically acceptable salt(s) thereof is desired at, or immediately adjacent to the point of application of the composition or formulation comprising the urotensinergic agent(s) or pharmaceutically acceptable salt(s) thereof.

The urotensinergic agents or pharmaceutically acceptable salts thereof may also be dispensed as a dry or liquid inhalation formulation using any suitable devices.

The pharmaceutical compositions of the present disclosure comprise a pharmaceutically effective amount of one or more of the urotensinergic agents or pharmaceutically acceptable salts thereof as described herein and one or more pharmaceutically acceptable carriers, excipients and/or diluents. In an embodiment of the present disclosure, the pharmaceutical compositions contain from about 0.0001% to about 99% by weight of one or more of the urotensinergic agents or pharmaceutically acceptable salts thereof. In a further embodiment of the present disclosure, the pharmaceutical compositions contain from about 0.0001% to about 60% by weight of one or more of the urotensinergic agents or pharmaceutically acceptable salts thereof, depending on which method of administration is employed. Physicians will determine the most-suitable dosage of the present therapeutic agent (i.e. the urotensinergic agents or pharmaceutically acceptable salts thereof). Dosages may vary with the mode of administration of the one or more of the urotensinergic agents or pharmaceutically acceptable salts thereof. In addition, the dosage may vary with the particular patient under treatment. The dosage of the one or more of the urotensinergic agents or pharmaceutically acceptable salts thereof used in the treatment may vary, depending on the condition, the weight of the patient, the relative efficacy and the judgment of the treating physician.

The concept of biased agonist activity suggests that specific ligand-induced conformational changes can lead to precisely directed signalling. Not wishing to be limited by theory, it was surmised that UII, which structurally differs from URP by the presence of an extended N-terminal domain that varies in length and composition, may induce a different conformational change of UT upon binding and therefore trigger the activation of a different set of second messengers leading to divergent physiological actions. The amino acids sequence of URP, which has been strictly conserved throughout species, suggests that specific receptor interactions have also been conserved, despite variations in the receptor primary amino acid sequence. Based on the specific expression of URP mRNA in several cerebral structures (e.g. rostroventrolateral medulla) and tissues (e.g. heart, seminal vesicle), it was suggested that URP rather than UII may be the biologically active peptide in the regulation of autonomic, cardiovascular and reproductive functions.[32] As described hereinabove, most of the structure-activity studies with UII were achieved by either replacing the Asp in position 4, the phenylalanine in position 6, the Lys in position 8 or the Tyr in position 9 by natural or unnatural amino acids.[9] However, except one report, no extensive structure-activity studies have been achieved with URP.[6] In order to elucidate the importance of the Trp residue for receptor interaction and biological activity of URP, a proteinogenic or a non-proteinogenic moiety, including cyclic residues, was introduced in the native sequence of URP (Scheme 2). Each compound (Table 5) was pharmacologically evaluated using radioligand binding experiments as well as an ex vivo rat aortic ring contraction bioassay. Some of these compounds were shown to be constrained agonists of the UT system. The more potent agonists were subsequently used in modeling studies in order to define a precise secondary structure involved in the recognition and activation of the UII receptor.

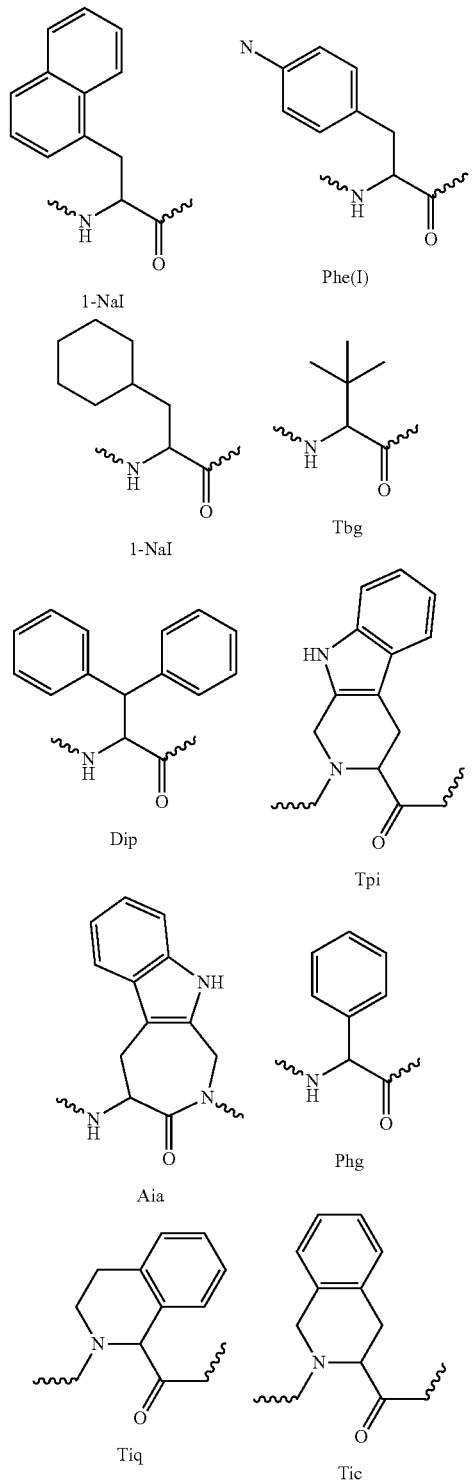

Insight into the Specific Role of Trp in URP-Mediated Biological Activity:

The role of aromaticity and steric hindrance in regards to binding affinity and biological activity was investigated. Replacement of the Trp moiety by 1-Nal, a sterically demanding derivative that may lead to improved interaction of the aromatic system with the hydrophobic areas of the receptor, led to an almost equipotent analog (compound 3, Table 6) compared to the native peptides (compounds 1 and 2, Table 6). These results suggest that it is the aromaticity, more than the strict nature of the aromatic ring, indole versus naphthalene, that is important for proper receptor recognition and activation. As expected, inversion of the configuration produced a slight but significant reduction in the binding affinity (compound 4, Table 6) as well as a dramatic reduction in contractile potency. For instance, exposure to increasing concentrations of [D-Nal⁴]URP up to 3 μM induced only a moderate vasoconstriction ($E_{max}$=34% at $10^{-5.5}$M). As previously mentioned, structure-activity relationships have highlighted the non-susceptibility of UII for Trp replacement by a phenylalanine moiety. In accordance, it was observed that the substitution of Trp by a Phe(I) induced a 4-fold drop in binding affinity, with [Phe(I)⁴]URP acting as a weak agonist of the urotensinergic system (compound 5, Table 6). This ligand could therefore serve as a template for the generation of peptide libraries derived from Pd-catalyzed cross coupling reactions. Interestingly, introduction of a bulky hydrophobic amino acid such as cyclohexylalanine (compound 6, Table 6) provoked only a 3-fold reduction in the binding affinity compared to compound 5 (Table 6). This compound, lacking an aromatic feature at position 4, yet behaved like a full but weak agonist of the urotensinergic system. Altogether, these results suggest that the presence of an aromatic moiety is preferable but not mandatory for complete receptor interaction/activation. Interestingly, and in accordance with these results, replacement of the Trp moiety with a D-tert-butyl-glycine produces a compound with low binding affinity that is however able to fully activate the UT receptor present in rat aortic ring (compound 8, Table 6). These results suggest that structural changes might occur within the peptide between the recognition and activation process of its cognate receptors and that these changes are linked to intra or intermolecular interactions involving the Trp side chain. The replacement of the Trp residue in hUII by a Pro moiety produced a weak agonistic effect. For instance, exposure to increasing concentrations of [Pro⁷]hUII up to 3 μM induced a substantial vasoconstriction ($E_{max}$=69% at $10^{-5.5}$M). It is therefore possible that the indole group in the native peptide is involved in such intramolecular interaction which seems to be required for proper recognition and activation. Moreover, the abovementioned results suggest that it is highly possible that the indole group, at least in URP, by interacting in an intramolecular manner, could stabilize the bioactive conformation leading to the proper orientation of other intracyclic residues for efficient receptor interaction/activation. Supporting this hypothesis, a tight contact among the Trp⁷, Lys⁸, and Tyr⁹ side chains of hUII have been observed for efficient receptor activation.

Introduction of Conformational Probes in Position 4.

The importance of the side-chain orientation on a stable backbone led to the concept of topographical design. The side chain of an amino acid can adopt three low-energy conformations, i.e. gauche(−), gauche(+), and trans. The energy difference and barrier between these conformations is rather small and as such all three conformations are accessible. During the initial peptide-receptor interactions, each of the critical side-chains will adopt one of these low conformations, thereby creating a unique pharmacophore. The χ1 torsion angle can be restricted by van der Waals forces, which can be introduced by substituents at the β-carbon. As such, introduction of a diphenylalanine (Dip), a more hindered aromatic amino acid, produces a weak UT agonist (compound 9, Table 6) suggesting that the cluster forming the Trp receptor-binding pocket is rather small and compact and might not be able to accommodate a bulky aromatic residue. However, another explanation is that the sterically demanding functional group at Cβ induces a conformational constraint around χ1 that impairs receptor interaction. More particularly, it is well established that Dip will simultaneously occupy the gauche(−) and trans orientations, excluding the gauche(+) orientation. It could therefore be hypothesized that such conformational restriction of the side chain, and thus of the χ1 torsion angle, could be responsible for the observed effect. Previous reports have highlighted that P5U, a potent UT agonist, as well as other UT receptor peptide agonists, show a trans orientation at this side chain suggesting that the gauche(−) orientation is detrimental for proper receptor interaction/activation. Due to the flexibility of peptide side chains, the proper topography during receptor interaction can only be studied by appropriate constraining or fixing of the side-chain conformers. As such, the rotation around the Cα-Cβ bond was restricted by the incorporation of the side chain into various ring structures. New compounds in which the Trp residue was replaced by a tetrahydro-β-carboline derivative (compounds 10 and 11) were designed and synthesized in order to limit the side chain conformation to a gauche(−) or gauche(+), excluding the trans orientation. Introduction of L-Tpi at position 4 produced a peptide with a high affinity for UT that is able to induce a vasoconstriction comparable to hUII or URP with however a slightly reduced potency (compound 10; Table 6). The Tpi moiety limits χ1 to the gauche(+) conformers, suggesting that this conformer could be critical for proper receptor interaction/activation. The inversion of configuration of this derivative (compound 11; Table 6) substantially reduced the binding affinity leading to an incomplete activation of the receptor as suggested by the weak agonist activity in the aortic ring contraction assay ($E_{max}$=43% at $10^{-5.5}$M). In accordance with the same reasoning, the gauche(+) or the trans conformer can be fixed by cyclizing the aromatic ring of Trp onto the nitrogen of the succeeding amino acid, thus leading to a 4-amino-1,2,4,5-tetrahydro-indolo[2,3-c]azepin-3-one (Aia). Surprisingly, the L-Aia derivative is characterized by a low binding affinity but conserved an interesting ability to induce aortic ring contraction (compound 12, Table 6). Interestingly, the inversion of configuration drastically improved the binding affinity with no change in the contractile activity (compound 13, Table 6). This result suggest that the change from a gauche(+) in L-Aia to the gauche(−) in D-Aia could be responsible for the increased binding affinity. These results also suggest that this particular position could be involved in the binding affinity and the stabilization of the peptide secondary structure. The almost equal binding potencies shown by [L-Tpi⁴]URP and [D-Aia⁴]URP, despite the differences in their side chain rotameric conformations at position 4, indicates that the binding affinity is rather insensitive to the changes of side chain conformation at position 4.

Overall, it seems that the side chain of the Trp moiety might be involved in intramolecular hydrophobic interaction aimed at stabilizing the bioactive conformation by restricting the conformational flexibility of the adjacent side chain, i.e. Phe³, Lys⁵, and Tyr⁶. It is thus likely that only the aromatic group at position 4 is important for binding activity, not its exact topochemistry. To examine for this possibility, two analogs (compounds 14 and 15, Table 6) incorporating a Phg (phenylglycine) or a D-Phg residue at position 4 were designed and synthesized. These analogs retain an aromatic group at position 4 while the rotation around the $C_\alpha$-$C_\beta$ bond is eliminated. The high binding affinity and reduced biological activity shown by [Phg⁴]URP and [D-Phg⁴]URP thus supports the above-mentioned hypothesis regarding the presence but not the topology of an aromatic group at position 4.

The most stable conformer of phenylglycine is stabilized by intramolecular hydrogen bonds N—H . . . O=C, N—H . . . π (with the closest C—C bond in the aromatic ring), and a cis-COOH interaction. The other conformer exhibits an O—H . . . N hydrogen bond between the hydrogen atom of the hydroxyl group and the lone pair on the nitrogen atom. It was surmised that by establishing similar interactions, the phenylglycine residue in URP might stabilize the conformation that is mandatory for proper interaction with the receptor. A further analogue, L-1,2,3,4-tetrahydroisoquinoline-1-carboxylic acid was synthesized. Pharmacological characterization of [Tiq$^4$]URP revealed that this analog possess a high binding affinity as well as a contractile efficacy and potency comparable to the endogenous peptides (compound 16; Table 6). Interestingly, inversion of configuration has no impact on the pharmacological profile of the analog, i.e. [D-Tiq$^4$]URP (compound 17; Table 6). Interestingly, introduction of a Tic moiety (compound 18; Table 6), which adopts a gauche(+) conformation within a peptide sequence, resulted in a dramatic loss of binding affinity and thus reduced contractile activity ($E_{max}$=43% at $10^{-5.5}$M). Inversion of the configuration of the Tic moiety (compound 19; Table 6) enabled the almost complete restoration of the binding affinity and biological activity. Due its bicyclic structure, formed via cyclization of the phenolic aromatic ring to the amine nitrogen, Tic provides two potential advantages for replacement of phenylalanine in bioactive peptide ligands, i.e. 1) conformational constraints are introduced in the peptide backbone by the pipecolic acid bridge; and 2) the orientation of the aromatic side chain is restricted. As such, the backbone restriction rather than the side chain restriction is involved in the effect observed with [Tic$^4$]URP and [D-Tic$^4$]URP, the D-isomer stabilizing a potentially active conformation.

Derivatization of the [Phe(I)]URP substrate through metal catalyzed reactions, for example palladium catalyzed reactions, i.e. Suzuki-Miyaura, Sonogashira, and Heck, provides access to functional allosteric modulators of the urotensinergic system. By interacting at an allosteric site, these compounds will select a specific receptor conformation that would enable UII receptor activation while preserving URP-mediated triggering. Generation of selective and competitive URP antagonist was readily achieved through the synthesis of the N-terminal domain of the various UII isoforms. These segments have been linked to interspecies differences in biological activities and could therefore represent species determinant to mediate URP biological activities. Stabilization of their secondary structure, probably observed during receptor interactions, could increase their potency and efficacy toward URP-mediated actions. Recent evidence leaned toward a more compact Trp-Lys-Tyr motif for potent activation of the UII receptor (agonist pharmacophore). As depicted earlier, introduction of a Tpi or Tiq moiety at position 4 probably stabilized the peptide backbone but also restricted the conformational freedom of the neighbouring side chains, i.e. Phe$^3$, Lys$^5$, and Tyr$^6$. By bringing these side chains into close proximity, potent and stable UT agonists could be accessible.

TABLE 5

Amino Acid Sequences of hUII, URP and Modified URP (compounds 1-22)

| Cpd Name | Sequence | HPLC$^a$ | MS$^b$ calc | MS$^b$ found |
|---|---|---|---|---|
| 1 hUII | H-Glu-Thr-Pro-Asp-Cys-Phe-Trp-Lys-Tyr-Cys-Val-OH (SEQ ID NO: 67) | 98% | 1387.6 | 1388.1 |
| 2 URP | H-Ala-Cys-Phe-Trp-Lys-Tyr-Cys-Val-OH (SEQ ID NO: 68) | 98% | 1016.4 | 1016.4 |
| 3 [1-Nal$^4$]URP | H-Ala-Cys-Phe-Nal-Lys-Tyr-Cys-Val-OH (SEQ ID NO: 69) | 98% | 1027.4 | 1028.7 |
| 4 [D-1-Nal$^4$]URP | H-Ala-Cys-Phe-*Nal*-Lys-Tyr-Cys-Val-OH (SEQ ID NO: 70) | 97% | 1027.4 | 1027.6 |
| 5 [Phe(I)$^4$]URP | H-Ala-Cys-Phe-Phe(I)-Lys-Tyr-Cys-Val-OH (SEQ ID NO: 71) | 98% | 1103.3 | 1103.6 |
| 6 [Cha$^4$]URP | H-Ala-Cys-Phe-Cha-Lys-Tyr-Cys-Val-OH (SEQ ID NO: 72) | 97% | 983.5 | 984.5 |
| 7 [Tbg$^4$]URP | H-Ala-Cys-Phe-Tbg-Lys-Tyr-Cys-Val-OH (SEQ ID NO: 73) | 97% | 943.4 | 944.3 |
| 8 [D-Tbg$^4$]URP | H-Ala-Cys-Phe-Tbg-Lys-Tyr-Cys-Val-OH (SEQ ID NO: 74) | 97% | 943.4 | 944.1 |
| 9 [Dip$^4$]URP | H-Ala-Cys-Phe-Dip-Lys-Tyr-Cys-Val-OH (SEQ ID NO: 75) | 97% | 1053.4 | 1054.3 |
| 10 [Tpi$^4$]URP | H-Ala-Cys-Phe-Tpi-Lys-Tyr-Cys-Val-OH (SEQ ID NO: 76) | 97% | 1028.4 | 1029.1 |
| 11 [D-Tpi$^4$]URP | H-Ala-Cys-Phe- -Lys-Tyr-Cys-Val-OH (SEQ ID NO: 77) | 98% | 1028.4 | 1029.3 |
| 12 [Aia$^4$]URP | H-Ala-Cys-Phe-Aia-Lys-Tyr-Cys-Val-OH (SEQ ID NO: 78) | 98% | 1028.4 | 1029.2 |

TABLE 5-continued

Amino Acid Sequences of hUII, URP and Modified URP (compounds 1-22)

| Cpd Name | Sequence | HPLC[a] | MS[b] calc | MS[b] found |
|---|---|---|---|---|
| 13 [D-Aia⁴]URP | H-Ala-Cys-Phe-_Aia_-Lys-Tyr-Cys-Val-OH (SEQ ID NO: 79) | 98% | 1028.4 | 1029.1 |
| 14 [Phg⁴]URP | H-Ala-Cys-Phe-Phg-Lys-Tyr-Cys-Val-OH (SEQ ID NO: 80) | 97% | 963.4 | 964.4 |
| 15 [D-Phg⁴]URP | H-Ala-Cys-Phe-_Phg_-Lys-Tyr-Cys-Val-OH (SEQ ID NO: 81) | 98% | 963.4 | 964.2 |
| 16 [Tiq⁴]URP | H-Ala-Cys-Phe-Tiq-Lys-Tyr-Cys-Val-OH (SEQ ID NO: 82) | 98% | 989.4 | 990.3 |
| 17 [D-Tiq⁴]URP | H-Ala-Cys-Phe-_Tiq_-Lys-Tyr-Cys-Val-OH (SEQ ID NO: 83) | 98% | 989.4 | 990.5 |
| 18 [D-Tic⁴]URP | H-Ala-Cys-Phe-Tic-Lys-Tyr-Cys-Val-OH (SEQ ID NO: 84) | 97% | 989.4 | 990.7 |
| 19 [D-Tic⁴]URP | H-Ala-Cys-Phe-_Tic_-Lys-Tyr-Cys-Val-OH (SEQ ID NO: 85) | 97% | 989.4 | 990.8 |
| 20 [Pen², Tiq⁴]URP | H-Ala-Pen-Phe-Tiq-Lys-Tyr-Cys-Val-OH (SEQ ID NO: 86) | 98% | 1017.4 | 1017.8 |
| 21 [Tiq⁴, Orn⁵]URP | H-Ala-Cys-Phe-Tiq-Orn-Tyr-Cys-Val-OH (SEQ ID NO: 87) | 98% | 975.4 | 976.6 |
| 22 [Tpi⁴, Orn⁵]URP | H-Ala-Cys-Phe-Tpi-Orn-Tyr-Cys-Val-OH (SEQ ID NO: 88) | 98% | 1014.4 | 1015.3 |

[a]Percentage purity determined by HPLC using buffer system: A = H$_2$O (0.1% TFA) and B = 60% CH$_3$CN/40% A with a gradient slope of 1% B/min, at flow rate of 1 mL/min on a Vydac C$_{18}$ column. Detection at 229 nm.
[b]MALDI mass spectral analysis (m/z). The observed [M + H]⁺ of the monoisotope compared with the calculated m/z monoisotopic mass. D-Amino acids are indicated in bold italic letters.

TABLE 6

Biological data for the Modified URP Compounds 1-22.

| | Binding | | | Aortic Ring contraction | | | |
|---|---|---|---|---|---|---|---|
| | IC$_{50}$ (nM)[a] | pEC$_{50}$ | n | EC$_{50}$ (nM)[b] | pEC$_{50}$ | E$_{max}$ (%)[c] | n |
| 1 | 13 (9-19) | 7.88 ± 0.07 | 3 | 1 (0.4-3) | 9.08 ± 0.25 | 117 ± 7 | 10 |
| 2 | 12 (7-20) | 7.90 ± 0.11 | 4 | 7 (3-17) | 8.09 ± 0.18 | 100 ± 6 | 10 |
| 3 | 17 (10-29) | 7.77 ± 0.12 | 3 | 54 (17-165) | 7.27 ± 0.24 | 86 ± 8 | 3 |
| 4 | 46 (34-63) | 7.33 ± 0.07 | 3 | 825 (676-1000) | 6.08 ± 0.04 | 34[d] | 3 |
| 5 | 58 (35-94) | 7.24 ± 0.11 | 3 | 506 (124-1150) | 7.05 ± 0.08 | 92[d] | 5 |
| 6 | 181 (121-272) | 6.74 ± 0.09 | 3 | >1000 | <6 | 77[d] | 4 |
| 7 | >10000 | <5 | | — | — | — | 3 |
| 8 | >1000 | <6 | | 262 (25-2800) | 6.58 ± 0.50 | 99 ± 27 | 3 |
| 9 | 277 (162-477) | 6.55 ± 0.12 | 3 | >1000 | <6 | 23[d] | 3 |
| 10 | 9 (5-15) | 8.05 ± 0.11 | 3 | 40 (10-164) | 7.39 ± 0.30 | 139 ± 17 | 3 |
| 11 | 361 (261-499) | 6.44 ± 0.07 | 3 | >1000 | <6 | 42[d] | 3 |
| 12 | 808 (514-1270) | 6.09 ± 0.09 | 3 | 181 (99-332) | 6.42 ± 0.13 | 51 ± 4 | 3 |
| 13 | 60 (44-82) | 7.22 ± 0.07 | 4 | 159 (68-371) | 6.79 ± 0.18 | 148 ± 12 | 5 |
| 14 | 29 (20-41) | 7.53 ± 0.08 | 3 | 251 (126-501) | 6.60 ± 0.15 | 102 ± 9 | 4 |
| 15 | 29 (20-41) | 7.56 ± 0.06 | 3 | 117 (75-184) | 6.93 ± 0.09 | 116 ± 5 | 3 |
| 16 | 10 (5-19) | 8.00 ± 0.15 | 4 | 22 (13-36) | 7.66 ± 0.11 | 126 ± 5 | 4 |
| 17 | 21 (12-34) | 7.68 ± 0.11 | 3 | 21 (9-46) | 7.68 ± 0.17 | 113 ± 7 | 4 |
| 18 | >10000 | <5 | 3 | >1000 | <6 | 43[d] | 4 |
| 19 | 88 (61-125) | 7.05 ± 0.08 | 3 | 259 (121-551) | 6.08 ± 0.04 | 128 ± 12 | 5 |
| 20 | >10000 | <5 | 3 | — | — | — | 2 |
| 21 | — | — | 3 | — | — | — | 2 |
| 22 | >10000 | <5 | 3 | — | — | — | 2 |

[a]IC$_{50}$ represent the concentration giving 50% of binding inhibition.
[b]Concentration producing 50% of the maximum effect. Values in parentheses are 95% confidence limits.
[c]The maximum efficacy is expressed as a percentage of the amplitude of the contraction induced by KCl (40 mM).
[d]Maximum efficacy at $10^{-5.5}$M.

Experimental

Materials and Methods

The in vitro and in vivo pharmaceutical characterization of [Bip$^4$]URP (i.e. urocontrin), a novel urotensin II receptor antagonist in accordance with the present specification, is illustrated hereinbelow.

Materials:

Fmoc-protected L- and D-amino acids, Wang polystyrene resin and the peptide coupling reagent TBTU (2-(1H-benzotriazole-1-yl)-1,1,3,3-tetramethyluronium tetrafluoroborate) were purchased from Chem-Impex (Wood Dale, Ill., USA). Common solvents for solid phase peptide synthesis were obtained from Fisher Scientific (Nepean, ON, CAN). Trifluoroacetic acid (TFA) was obtained from PSIG (Montreal, QC, CAN). Isotopes (i.e. Na$^{125}$I), were purchased from Perkin Elmer (Montreal, QC, CAN). Other chemicals including D-glucose, Trizma® hydrochloride, Trizma® base, bovine serum albumin, manganese(II) chloride, chloramine-T, sodium bisulfite, sodium chloride, sodium bicarbonate, calcium chloride, magnesium sulfate, N,N-diisopropylethylamine (DIPEA; Hünig's base), isoflurane, heparin, xylazine, ketamine, potassium chloride, and potassium phosphate monobasic, were ordered from Sigma Aldrich (Mississauga, ON, CAN).

Animals:

Adult male Sprague-Dawley rats (Charles River, St-Constant, QC, CAN) weighing 250-300 g or 350-400 g were housed in group cages under controlled illumination (12:12 h light-dark cycle), humidity, and temperature (21-23° C.). The rats had free access to tap water and rat chow. All experimental procedures were performed in accordance with the regulations and ethical guidelines from the Canadian Council for the Care of Laboratory Animals and received approval by the institutional animal care and use committee of the Institut National de la Recherche Scientifique-Institut Armand-Frappier and the animal ethics and research committee of the Montreal Heart Institute, respectively.

Peptide Synthesis and Characterization:

URP and all URP derivatives were synthesized manually using standard solid phase peptide synthesis using Fmoc chemistry. Coupling of the protected amino acids was mediated by TBTU (1 eq.) and DIPEA (2 eq.) in DMF over a period of 1 h and monitored by the qualitative ninhydrin test. A 3-equivalent excess of protected amino acid, based on the original substitution of the Fmoc-Val-WANG resin (0.7 mmol/g), was used in most cases. Fmoc removal was achieved using 20% piperidine in DMF over a period of 20 min. To prevent unwanted Fmoc removal during the palladium-catalyzed cross-coupling reaction, the last amino acid was introduced as a Boc-derivative (Boc-Ala-OH). Conditions used to carry out the cross-coupling reaction on the solid support were as follows: [Phe(I)$^4$]URP peptidyl-resin (1 eq), phenylboronic acid (3 eq) and Na$_2$CO$_3$ (3 eq) were dissolved in degassed DMF/DCM (1:1, v/v). The mixture was bubbled with argon over a period of 10-15 min after which Pd(PPh$_3$)$_4$ (0.1 eq) was added. The reaction was subsequently stirred overnight at 80° C. The resin was then filtered and washed successively with DMF, H$_2$O, MeOH, DMF, and DCM. All peptides were cleaved from the resin support, with simultaneous side-chain deprotection, by treatment with TFA containing 1,2-ethanedithiol (2.5%), water (2.5%) and tri-isopropylsilane (1%) over a period of 1.5 h at room temperature. The diethyl ether-precipitated crude peptides were solubilized in 70% acetic acid (1 mg/mL) and then cyclized by the addition of iodine (10% solution in methanol) until the appearance of a stable orange color. Thirty minutes later, ascorbic acid was added to quench the excess iodine. Crude cyclic lyophilized peptides were purified using a preparative reverse-phase HPLC protocol using a linear gradient from eluent A to B with 1% B per 2 min increment (Eluent A=H$_2$O, 0.1% TFA; Eluent B=60% CH$_3$CN/40% A, 0.1% TFA). Homogeneity of purified fractions was assessed by RP-HPLC and mass spectrometry in linear mode using α-cyanohydroxycinnamic acid as the matrix. The pure fractions (>95%) containing the product were pooled and subjected to lyophilization. Overall, RP-HPLC analysis of the URP analogs revealed that the purity of all peptides was higher than 97% (Tables 5, 7 and 11). Moreover, for all peptides, the molecular weight observed by MS analysis agreed with the theoretical values (Table 5, 7 and 11). The synthesis of human urotensin II (hUII) was carried following known procedures.

Cell Culture and Binding Experiments:

Transfected CHO cells expressing the human urotensin receptor (CHO-UT) were maintained in Ham-F12 medium with 10% fetal bovine serum (FBS), 2 mM L-glutamine, 100 UI/mL each of penicillin and streptomycin, and 400 µg/mL G418. Synthetic hUII (10 µg) was radiolabeled with 0.5 mCi Na$^{125}$I (PerkinElmer, Montreal, QC, CAN) using the chloramine-T technique. Iodinated $^{125}$I-hUII was purified on a C$_{18}$ Sep-Pak cartridge, collected and stored at −20° C. until used. Binding assays were following known literature procedures using CHO cells stably transfected with hGPR14. Briefly, cells were exposed to increasing concentrations of peptides in the presence of 0.2 nM $^{125}$I-hUII. After 90 min of incubation at room temperature, cells were washed, lysed, and the cell-bound radioactivity was quantified using a γ-counter. Results were expressed as a percentage of the specific binding of $^{125}$I-hUII obtained in the absence of competitive ligands. Non-specific binding was determined in the presence of 10 µM hUII and ranged between 10 and 15% of total binding. For dissociation studies, CHO-UT cells were equilibrated over a period of 2 h with $^{125}$I-hUII or $^{125}$I-URP (0.2 nM) and dissociation of receptor-bound radioligand, measured at different intervals, was initiated by the addition of a supra-maximal concentration of either hUII (10$^{-6}$M) or URP (10$^{-6}$M), or by the simultaneous addition of hUII (10$^{-6}$M) and URP derivative (10$^{-6}$M) or URP (10$^{-6}$M) and URP derivative (10$^{-6}$M). The cells were then washed, lysed, and the radioactivity counted on a γ-counter (1470 Automatic Gamma Counter, Perkin Elmer).

Organ Bath Experiments:

Male rats (Sprague-Dawley, 250-300 g) were killed by CO$_2$ asphyxiation. The thoracic aorta was then cleared of surrounding tissues and excised from aortic arch to the diaphragm. From each vessel, conjunctive tissues were removed and the clean vessel was cut into 4 mm rings. The endothelium was removed by gently rubbing the vessel's intimal surface. All preparations were placed in 5 ml organ baths filled with oxygenated normal Krebs-Henselheit solution. Contractile responses to 40 mM KCl were used as control at the beginning and at the end of each experiment. Agonistic activity was measured by increasing the concentration of the peptide in the organ chamber ($3\times10^{-11}$-$3\times10^{-6}$ M). For antagonist behaviour, thoracic aortic rings were first exposed to URP derivative over a period of 15 min, and then cumulative concentration-response curves to hUII, URP or ET-1 ($10^{-10}$-$3\times10^{-6}$ M) were constructed. The amplitude of the contraction induced by each concentration of peptide was expressed as a percentage of the KCl-induced contraction. Finally, the ability of the antagonist to reverse the hUII-induced contraction was also evaluated. Vessels were pre-contracted with 4 nM hUII (pre-determined $EC_{80}$) and after the maximum contraction was attained, contractile tone was reversed by adding increasing log unit concentrations of URP derivative. The median effective concentrations ($EC_{50}$) are expressed as the mean±S.E.M., and the n values, representing the total number of animals from which the vessels were isolated, varied from 4 to 8 animals.

Hemodynamic Assessment:

Male Sprague-Dawley rats, weighing 350-400 g, were anaesthetized by isoflurane inhalation delivered in 100% oxygen (1 l/min) from an Ohmeda Tec 4 anaesthetic vaporizer (Somatechnology, Inc., Bloomfield, Conn., USA). Anaesthesia was maintained by mask inhalation of isoflurane vaporized at concentrations of up to 3% in the induction phase, at 1.5% during acute surgical procedures and at 0.8-1.0% during experimental observations. After anaesthesia, a polyethylene catheter (PE 10) was inserted into the right jugular vein to inject saline (0.9% NaCl in water) or drugs. To measure arterial blood pressure, an incision was made at the common right carotid artery where a microtip pressure transducer catheter (model SPR-407, 2F, Millar Instruments, Houston, Tex., USA) was inserted. A period of stabilisation of 30 min was observed and the following experimental protocols were then performed and arterial blood pressure was evaluated. During isoflurane inhalation, no breathing complications or changes in blood pressure were observed. Mean values of MAP were 114±3 mm Hg at basal and were not modified by saline bolus injections.

Human UII Dosage Range Determination:

In a preliminary study, individual rats received a single i.v. injection of hUII ranging from 1 to 30 nmol/kg. A dose-response curve, reflecting the effect of hUII on the change in blood pressure, was then determined. Results showed that the most significant drop in blood pressure was observed at 10 nmol/kg. This dose was further used to characterize the in vivo pharmacological effects of systemic injections of [Bip$^4$] URP.

Effect of [Bip$^4$]URP on a Single Intravenous Injection of hUII or URP in Anaesthetized Rat:

In this set of experiments, five groups of rats were used. Group one was employed to evaluate the intrinsic property of [Bip$^4$]URP at low (100 nmol/kg) and high dosage (1000 nmol/kg). Others groups were used to assess the hemodynamic profile of a single i.v. injection (200 µl over a 10 s period) of either hUII (10 nmol/kg) or URP (10 nmol/kg) in the absence (control) or in the presence (treated) of [Bip$^4$] URP. In treated groups, prior to hUII or URP administration (10 nmol/kg), the rats were exposed to [Bip$^4$]URP (100 nmol/kg or 1000 nmol/kg) over a period of 30 min. Baseline hemodynamic parameters were assessed over a period of 5 min prior to bolus injection of the drugs. Hemodynamic changes were continuously captured by the pressure probe over a period of 1 h. The maximum rise and the maximum drop in blood pressure was determined and analyzed using the PowerLab software (ADInstruments, Colorado Springs, Colo., USA).

Effect of [Bip$^4$]URP on Repeated Intravenous Injections of hUII:

In the control group, the rats received two doses of hUII (10 nmol/kg) with a 30 min interval between the first and second injection. As for the treated group, the same protocol was applied except that an additional dose of [Bip$^4$]URP (1000 nmol/kg) was given 30 min prior to the injection protocol performed in the control group.

Data Analysis:

Binding and functional experiments were performed at least in triplicate and data, expressed as mean±S.E.M, were analyzed using the Prism software (Graph Pad Software, San Diego, Calif.). In all experiments, n represents the total number of animals studied or individual assays performed. The $EC_{50}$, $pEC_{50}$, $pIC_{50}$ values as well as the $E_{max}$ value were determined from the concentration-response curves using a sigmoidal dose-response fit with variable slope. Non-competitive antagonist affinities (pKb) were determined using the method of Gaddum where equiactive concentrations of agonist, in the absence or presence of URP derivative, were compared in a linear regression. The resulting slope was used to calculate the equilibrium constant $K_b$ using the following equation: $K_b=[B]/(slope-1)$; where [B] is the antagonist concentration. The slope is calculated from the double reciprocal plot of equiactive concentrations of agonist in the presence and absence of antagonist. Statistical comparisons of the binding affinities and contractile potencies of URP, hUII and URP analogues were analyzed by ANOVA followed by a Dunnett's multiple comparison test and differences were considered significant where *$P<0.05$, $P<0.01$, and *$P<0.001$.

Results

Radiolabeled hUII or URP Binding to UT Receptors is Inhibited by [Bip$^4$]URP:

The cell system as used herein, CHO cells transfected with the human UII receptor (UT), was previously used to evaluate the capacity of hUII analogs to bind to the human urotensin II receptor[4]. Unlabeled hUII and URP inhibited $^{125}$I-hUII binding to UT receptors in CHO-UT cells with an $IC_{50}$ of 13.2 nM and 12.4 nM respectively (Table 7). Similarly, unlabeled hUII and URP inhibited $^{125}$I-URP binding with an $IC_{50}$ of 32.5 nM and 31.8 nM respectively (Table 7). Radioligand binding ($^{125}$I-hUII, $^{125}$I-URP) to UT receptors was also inhibited by [Bip$^4$]URP with an apparent $IC_{50}$ value of 386 nM and 339 nM respectively (Table 7). Overall, [Bip$^4$]URP is able to consistently and completely displace both radioligands, i.e. $^{125}$I-hUII and $^{125}$I-URP by 100%.

TABLE 7

Physiochemical propterties and binding affinities of
hUII, URP and [Bip⁴] URP to recombinant human UT.

| No | Cpd. Name | Sequence | Purity | MS Calc | MS Found | Binding ($^{125}$I-hUII) | | | Binding ($^{125}$I-URP) | | |
|----|-----------|----------|--------|---------|----------|---------------------|------|---|---------------------|------|---|
| | | | | | | $EC_{50}$ (nM) | $pEC_{50}$ | n | $EC_{50}$ (nM) | $pEC_{50}$ | n |
| 1 | hUII | H-Glu-Thr-Pro-Asp-Cys-Phe-Trp-Lys-Tyr-Cys-Val-OH (SEQ ID NO: 29) | ≥98% | 1387.6 | 1388.1 | 13.2 | 7.88 ± 0.07 | 3 | 32.5 | 7.49 ± 0.11 | 3 |
| 2 | URP | H-Ala-Cys-Phe-Trp-Lys-Tyr-Cys-Val-OH (SEQ ID NO: 36) | ≥98% | 1016.4 | 1016.4 | 12.4 | 7.90 ± 0.11 | 4 | 31.8 | 7.50 ± 0.11 | 4 |
| 3 | [Bip⁴]URP | H-Ala-Cys-Phe-Bip-Lys-Tyr-Cys-Val-OH (SEQ ID NO: 89) | ≥98% | 1053.4 | 1053.4 | 386.0 | 6.41 ± 0.12 | 3 | 338.8 | 6.47 ± 0.12 | 4 |

Figure 2:
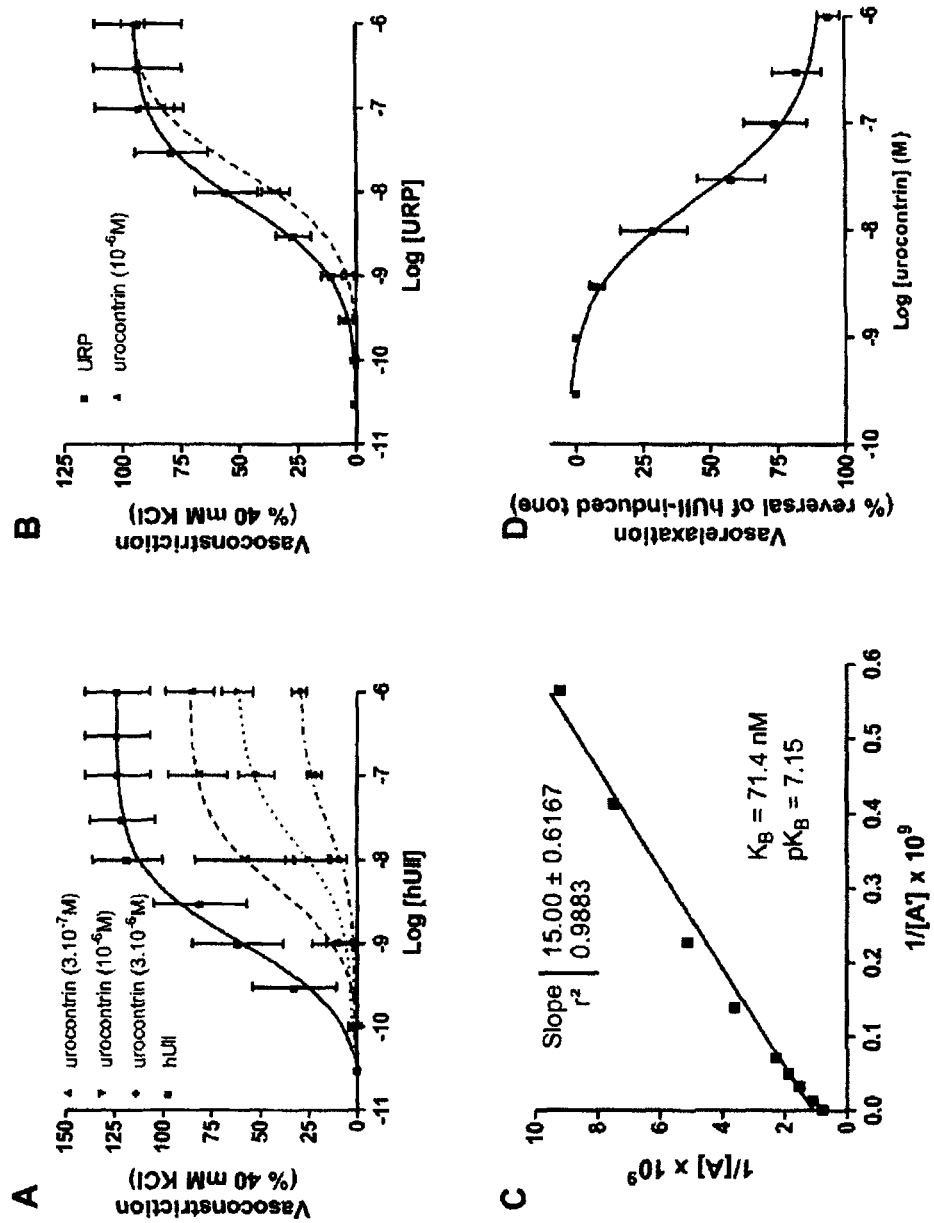
FIGS. 2A-D are illustrations of the effects of [Bip$^4$]URP (i.e. urocontrin) on hUII- and URP-induced contraction of rat aortic ring. [Bip$^4$]URP suppressed the maximum contractile response to hUII in a concentration-dependent manner but not URP. Double reciprocal plot of equiactive concentrations of hUII in the absence (FIG. 2A) and presence (FIG. 2B) of 1 μM [Bip$^4$]URP is linear (consistent with non-competitive antagonism) with a slope of 15.0±0.6 (FIG. 2C), indicating a pKb of 7.15. Concentration-dependent relaxation response to [Bip$^4$]URP is expressed as percent reversal of the original tone established in endothelium denuded aortae with 4 nM hUII (FIG. 2D). Data represent the mean±S.E.M. and n=5 to 10 animals.

Effects of [Bip⁴]URP on hUII- and URP-Induced Contraction of Rat Aortic Ring:

In the rat isolated aorta bioassay, hUII and URP evoked dose-dependent contractions (FIG. 1) with a $pEC_{50}$ of 8.98±0.21 ($E_{max}$ of 124±8% response to 40 mM KCl; n=10) and 8.09±0.18 ($E_{max}$=100±6; n=10), respectively. Exposure to increasing concentrations of [Bip⁴]URP up to 3 μM induced only a weak vasoconstriction ($E_{max}$=8.7% at $10^{-5.5}$ M). [Bip⁴]URP was subsequently tested for its ability to antagonize hUII or URP-mediated contraction of isolated rat aortic rings. As shown in FIG. 2 and Table 8, various concentrations of [Bip⁴]URP did not produce any significant rightward shift of the hUII concentration-response curve, however the maximal response to hUII was not attainable. For instance, pre-treatment with [Bip⁴]URP at $10^{-6}$M, produced a significant suppression ($E_{max}$=61±6%) of the maximum contractile response to hUII with a slight shift in the concentration-response curve ($pEC_{50}$=7.60±0.29). Interestingly, a slight but non-significant rightward shift ($pEC_{50}$=7.74±0.12) with a non-significant reduction of efficacy ($E_{max}$=102±5) was observed with URP. Consistent with non-competitive antagonism, the slope of the double reciprocal plot of equiactive concentrations of agonist in the presence and absence of 1 μM [Bip⁴]URP was linear with a slope of 15.00±0.62, equating to a $pK_b$ of 7.15 (FIG. 2). Finally, [Bip⁴]URP potently ($pIC_{50}$=7.72±0.15; n=6) and efficaciously (92% suppression) reversed contractile tone established in rat isolated aorta with an $EC_{80}$ dose of hUII (4 nM hUII) (FIG. 2).

TABLE 8

Concentration-dependent inhibition of hUII-induced
contraction of rat isolated aorta by [Bip⁴]URP.

| [Bip⁴]URP (μM) | hUII $E_{max}$ (% KCl) | hUII $pEC_{50}$ | n |
|---|---|---|---|
| Vehicle | 124 ± 8 | 8.98 ± 0.21 | 10 |
| 0.3 | 86 ± 11 | 8.31 ± 0.37 | 3 |
| 1 | 61 ± 7* | 7.60 ± 0.29* | 5 |
| 3 | 30 ± 3** | 7.55 ± 0.26** | 6 |

All values are expressed as the mean ± SEM. Statistical comparisons for both $pEC_{50}$ and $E_{max}$ values were performed using paired, two-tailed Student's t-test where *$P < 0.05$ and **$P < 0.01$ versus vehicle control values. Linear regression analysis of 1 μM [Bip⁴]URP using the method of Gaddum resulted in a linear plot (consistent with non-competitive antagonist) with a slope of 15.00 ± 0.61, equating to a $pK_b$ of 7.15.

Figure 3:
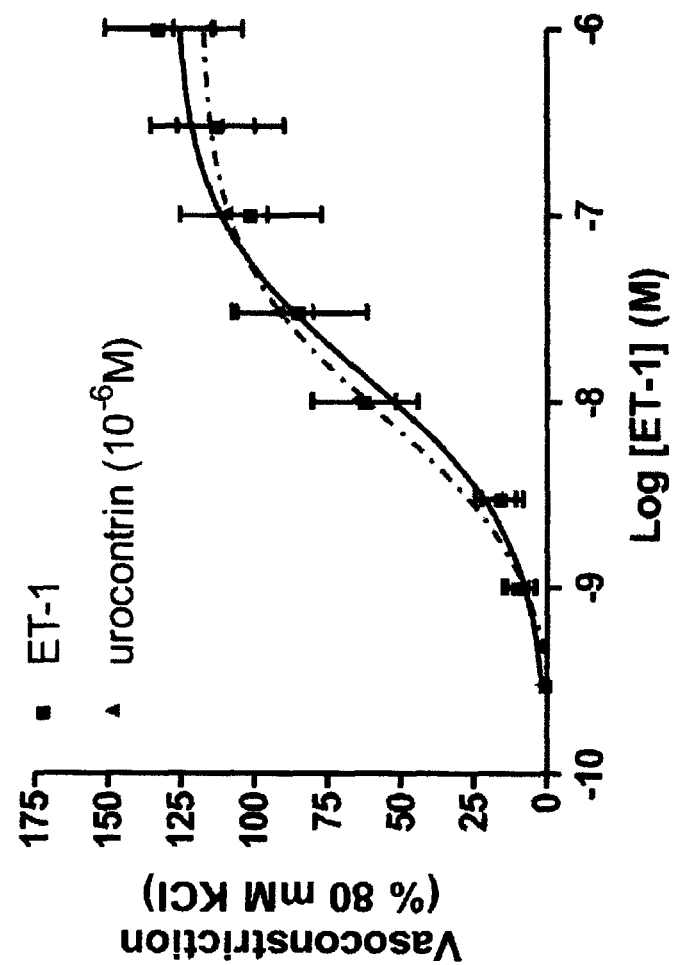
FIG. 3 is an illustration of the effects of [Bip$^4$]URP (i.e. urocontrin) on ET-1-induced contraction of rat aortic ring. [Bip$^4$]URP did not inhibit or potentiate endothelin-1-induced vasoconstriction. Data represent the mean±S.E.M. and n=5 to 10 animals.

Effects of [Bip⁴]URP on ET-1-Induced Contraction of Rat Aortic Ring:

To further characterize the properties of [Bip⁴]URP, its specificity as a hUII antagonist was assessed by examining the effect of [Bip⁴]URP on the contractile response to ET-1. Indeed, it was demonstrated that somatostatin ligands (agonist and antagonist) are able to potentiate the ET-1-induced effect in rat aorta.[2,4] Mean $EC_{50}$ values with and without [Bip⁴]URP ($10^{-6}$M), respectively, were as follows: ET-1 $pEC_{50}$=7.85±0.25 ($E_{max}$=127±10; n=8) and 8.06±0.15 ($E_{max}$=119±6; n=6) (FIG. 3). Thus, this antagonist is not able to alter the concentration-response curves of ET-1-mediated contraction. Consequently, it is unlikely that [Bip⁴]URP exerts its action through the activation of somatostatin receptors.

Figure 4:
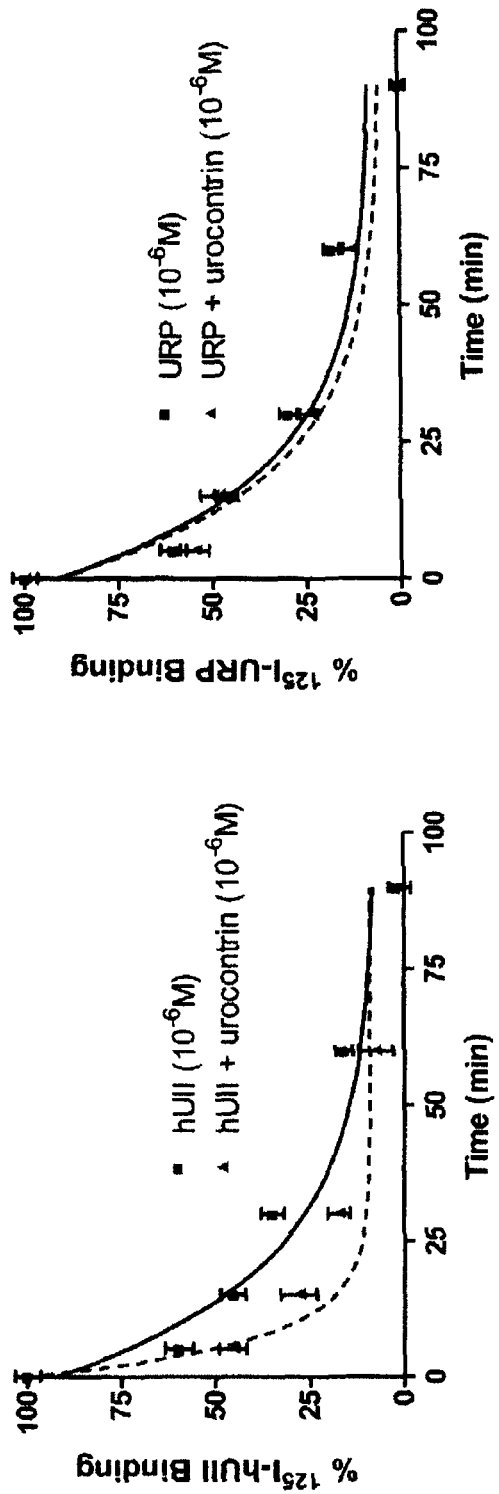
FIG. 4 is an illustration of the influence of [Bip$^4$]URP (i.e. urocontrin) on the dissociation rate of hUII or URP. Dissociation time-courses of bound $^{125}$I-hUII or $^{125}$I-URP were assessed on living CHO cells overexpressing the human urotensin II receptor. Once binding reached equilibrium, dissociation was initiated by the addition of a supra-maximal concentration of hUII ($10^{-6}$M) or URP ($10^{-6}$M) alone, or by the simultaneous addition of hUII ($10^{-6}$M) and [Bip$^4$]URP ($10^{-6}$M) or URP ($10^{-6}$M) and [Bip$^4$]URP ($10^{-6}$M). The dissociation constant of $^{125}$I-hUII (0.050±0.006 min$^{-1}$) was significantly different (**P<0.01) in the presence of the antagonist (0.153±0.019 min$^{-1}$), indicating that [Bip$^4$]URP probably binds to an allosteric site. Surprisingly, no significant change in the dissociation rate of $^{125}$I-URP (0.052±0.006 min$^{-1}$ versus 0.054±0.006 min$^{-1}$) was observed.

Influence of [Bip⁴]URP on the Dissociation Rate of hUII or URP:

To determine whether the insurmountable antagonism of hUII by [Bip⁴]URP observed in the functional assay could be due to the compound binding at an allosteric site different from the agonist binding domain, CHO-UT cells were incubated with either $^{125}$I-hUII or $^{125}$I-URP until binding equilibrium was reached. Dissociation of the bound radioligand was then initiated by high concentration of the corresponding unlabeled peptide in the absence or presence of an excess of [Bip⁴]URP. The supramaximal concentration of unlabeled hUII or URP causes the dissociation of bound radioligand from its receptor site. If the addition of the ligand alters the dissociation rate of the radioligand, it must do so by interacting at a different <<allosteric>> site.[28] The half-life of $^{125}$I-hUII (13.84 min) and its dissociation constant ($k_{off}$=0.05 min$^{-1}$) was significantly different (P<0.01) in the presence of the antagonist ($t_{1/2}$=4.52 min and $k_{off}$=0.15 min$^{-1}$), indicating that [Bip⁴]URP probably binds to an allosteric site (FIG. 4 and Table 9). Surprisingly, no change in the dissociation rate of $^{125}$I-URP was observed.

TABLE 9

Dissociation constant of $^{125}$I-hUII or $^{125}$I-URP bound to recombinant human UT receptors in CHO cells in the absence or presence of [Bip$^4$]URP

| $^{125}$I-hUII | | | | |
|---|---|---|---|---|
| | hUII | n | hUII + urocontrin | n |
| Half-life (t$_{1/2}$, min) | 13.84 (11.11-18.36) | 8 | 4.52 (3.60-6.07)** | 7 |
| Dissociation constant (k$_{off}$, min$^{-1}$) | 0.050 ± 0.006 | | 0.153 ± 0.019** | |

| $^{125}$I-URP | | | | |
|---|---|---|---|---|
| | URP | n | URP + urocontrin | n |
| Half-life (t$_{1/2}$, min) | 13.13 (10.52-17.44) | 4 | 12.06 (9.12-17.47) | 6 |
| Dissociation constant (k$_{off}$, min$^{-1}$) | 0.052 ± 0.006 | | 0.054 ± 0.006 | |

Statistical comparisons were performed using unpaired t-test analysis (**P < 0.01 versus control values). Values in parentheses are 95% confidence limits.

Figure 5:
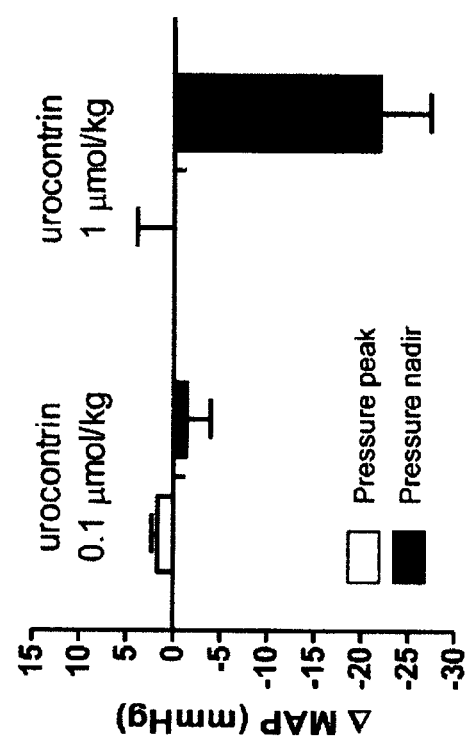
FIG. 5 is an illustration of the evaluation of the intrinsic property of [Bip$^4$]URP (i.e. urocontrin) at low (100 nmol/kg) and high dosage (1000 nmol/kg). No effect was observed at low concentrations. However, at a high dose (1000 nmol/kg), it produced a hypotensive effect comparable with that of hUII.
Figure 6:
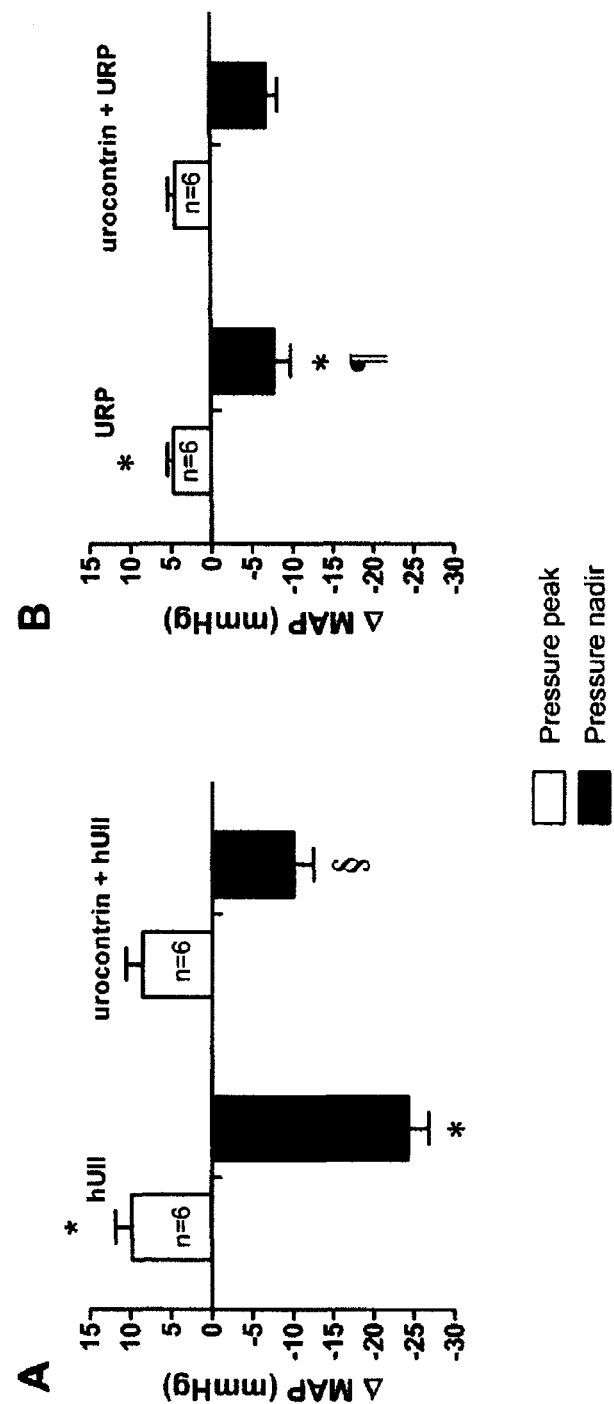
FIGS. 6A-B are illustrations of the effect of [Bip$^4$]URP (i.e. urocontrin) on hUII (FIG. 6A) and URP (FIG. 6B) hemodynamic action in anaesthetized rats. Bolus injection of [Bip$^4$]URP (1000 nmol/kg) significantly reduced the hUII hypotensive action while keeping intact its pressor effect. Interestingly, [Bip$^4$]URP (1000 nmol/kg) had no effect on the biphasic response induced by URP (10 nmol/kg), suggesting its selective action on hUII physiological action.

Effect of [Bip$^4$]URP on hUII and URP Hemodynamic Action in Anaesthetized Rats:

Systemic injection of urocontrin at a dose of 0.1 μmol/kg caused no detectable effect on blood pressure. However, at a dose of 1 μmol/kg, it produced a hypotension comparable with that of hUII at 0.01 μmol/kg (FIG. 5). Since the maximum effect of urocontrin or hUII on the mean arterial pressure was not investigated, it is therefore impossible to clearly define urocontrin as a weak agonist or a partial agonist. Bolus i.v. injection of hUII (0.01 μmol/kg) or URP (0.01 μmol/kg) produced a biphasic hemodynamic response characterized by a rapid and transient pressor phase with a peak (*P<0.05) occurring after ~1 min, followed by a long lasting hypotension phase reaching a nadir (*P<0.05) at ~6 min (FIGS. 6A and 6B). Even though similar effects were observed with a bolus injection of URP, the hypotension effect was significantly less pronounced as compared to the same dose of hUII (P<0.05) (FIG. 5B). Bolus injection of urocontrin (1 μmol/kg) significantly reduced ($^§$P<0.05) hUII hypotensive action while preserving its pressor effect (FIG. 6A). At a lower dose, i.e. 0.1 μmol/kg, urocontrin had no effect on the hUII hemodynamic profile (data not shown). Interestingly, urocontrin (1 μmol/kg) had no effect on the biphasic response induced by URP (10 nmol/kg) (FIG. 6B)

Figure 7:
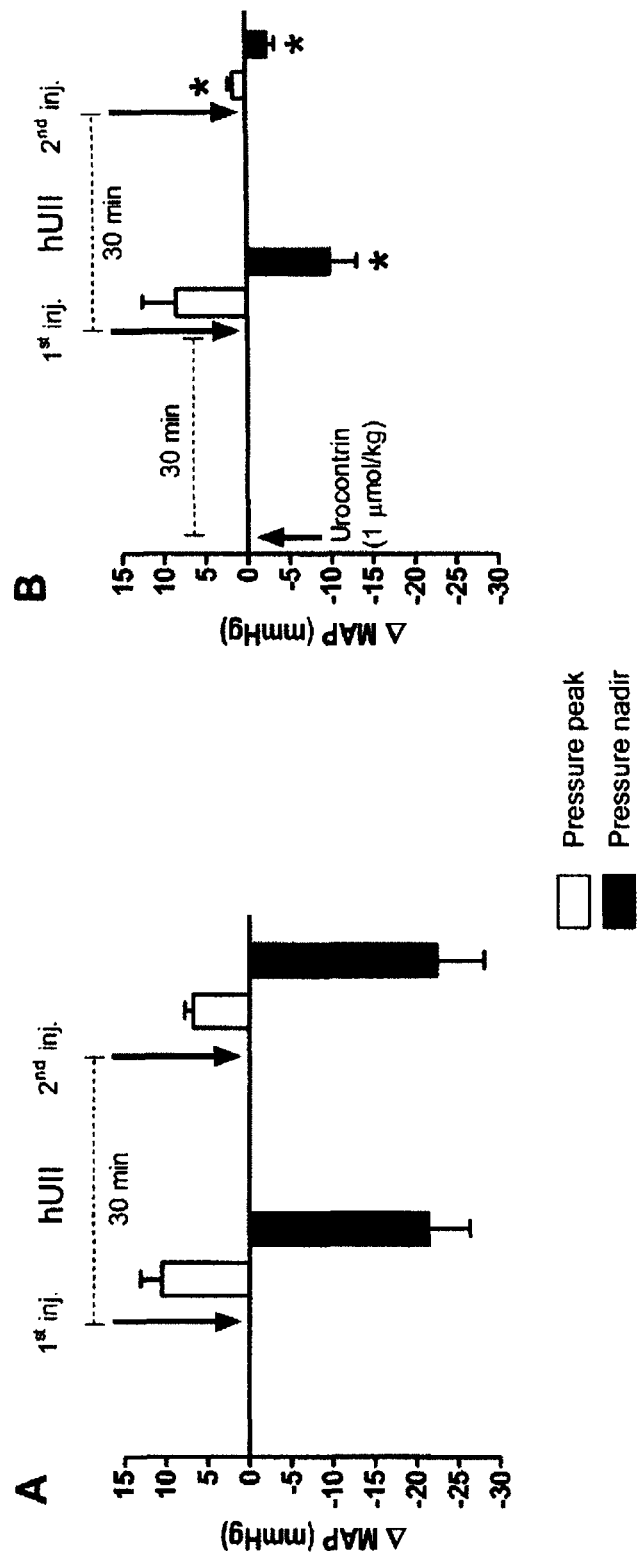
FIGS. 7A-B are illustrations of the effect of [Bip$^4$]URP (i.e. urocontrin) on repeated intravenous hUII injection.

Effect of [Bip$^4$]URP on Repeated Intravenous hUII Injection:

Recent reports demonstrated a desensitization of the urotensinergic system following repeated injection of hUII in eight week-old SHR rats.[31] However, no experiments were performed using normotensive rats. Repeated injection of hUII produced equivalent biphasic responses suggesting a no tolerance effect of hUII (FIG. 7A). Worthy of notice is the complete absence of a response to a second injection of hUII when rats were treated with [Bip$^4$]URP (1000 nmol/kg) (FIG. 7B).

Figure 8:
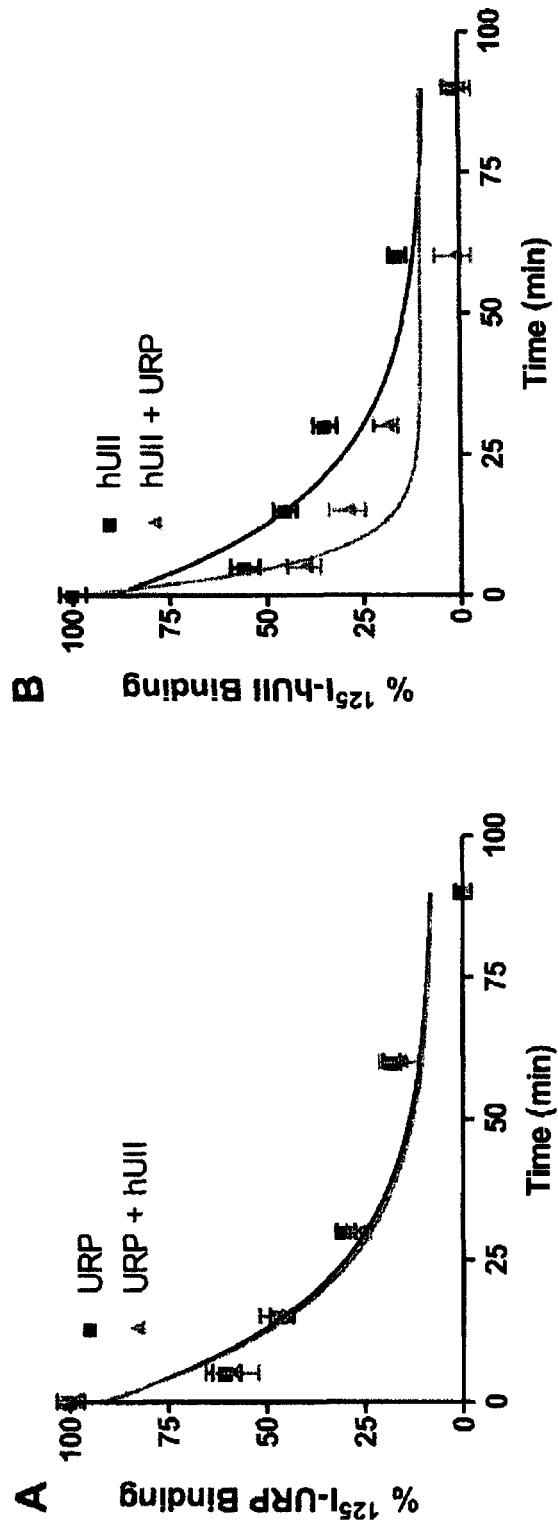
FIG. 8A is an illustration of the influence of hUII on the dissociation rate of $^{125}$I-URP.
FIG. 8B is an illustration of the influence of URP on the dissociation rate of $^{125}$I-hUII. Dissociation time-courses of bound $^{125}$I-hUII or $^{125}$I-URP were assessed on living CHO cells over-expressing the human urotensin II receptor. Significant differences (**P<0.01) were determined by unpaired Student t-test.

Influence of hUII and URP on the Dissociation Rate of Bound $^{125}$I-hUII or $^{125}$I-URP:

The unusual pattern observed with urocontrin, i.e. [Bip$^4$] URP, a URP derivative, prompted the evaluation of the propensity of URP to exert a similar effect on the hUII dissociation rate. As shown in Table 10, URP and hUII bind hUT receptors with high affinity. Dissociation of the bound radioligand, either $^{125}$I-hUII or $^{125}$I-URP, was initiated by high concentration (10$^{-6}$M) of the corresponding unlabeled peptide in the absence or presence of an excess of URP or hUII (10$^{-6}$M). The presence of URP induced a significant (P<0.01) acceleration of the $^{125}$I-hUII dissociation rate (k$_{off}$=0.050±0.006 versus 0.174±0.026; FIG. 8B). Surprisingly, no change in the dissociation rate of $^{125}$I-URP (k$_{off}$=0.052±0.006 versus 0.055±0.009) was observed following the addition of a supramaximal concentration of hUII (FIG. 8A).

TABLE 10

Binding Affinities of hUII and URP to recombinant human UT.

| | Binding ($^{125}$I-hUII) | | Binding ($^{125}$I-URP) | |
|---|---|---|---|---|
| | IC$_{50}$ (nM)$^{[a]}$ | pIC$_{50}$ | IC$_{50}$ (nM)$^{[a]}$ | pIC$_{50}$ |
| hUII | 13.2 | 7.88 ± 0.07 | 32.5 | 7.49 ± 0.11 |
| URP | 12.4 | 7.90 ± 0.11 | 31.8 | 7.50 ± 0.11 |

[a]IC$_{50}$ values represent concentration giving 50% of binding inhibition.

Figure 9:
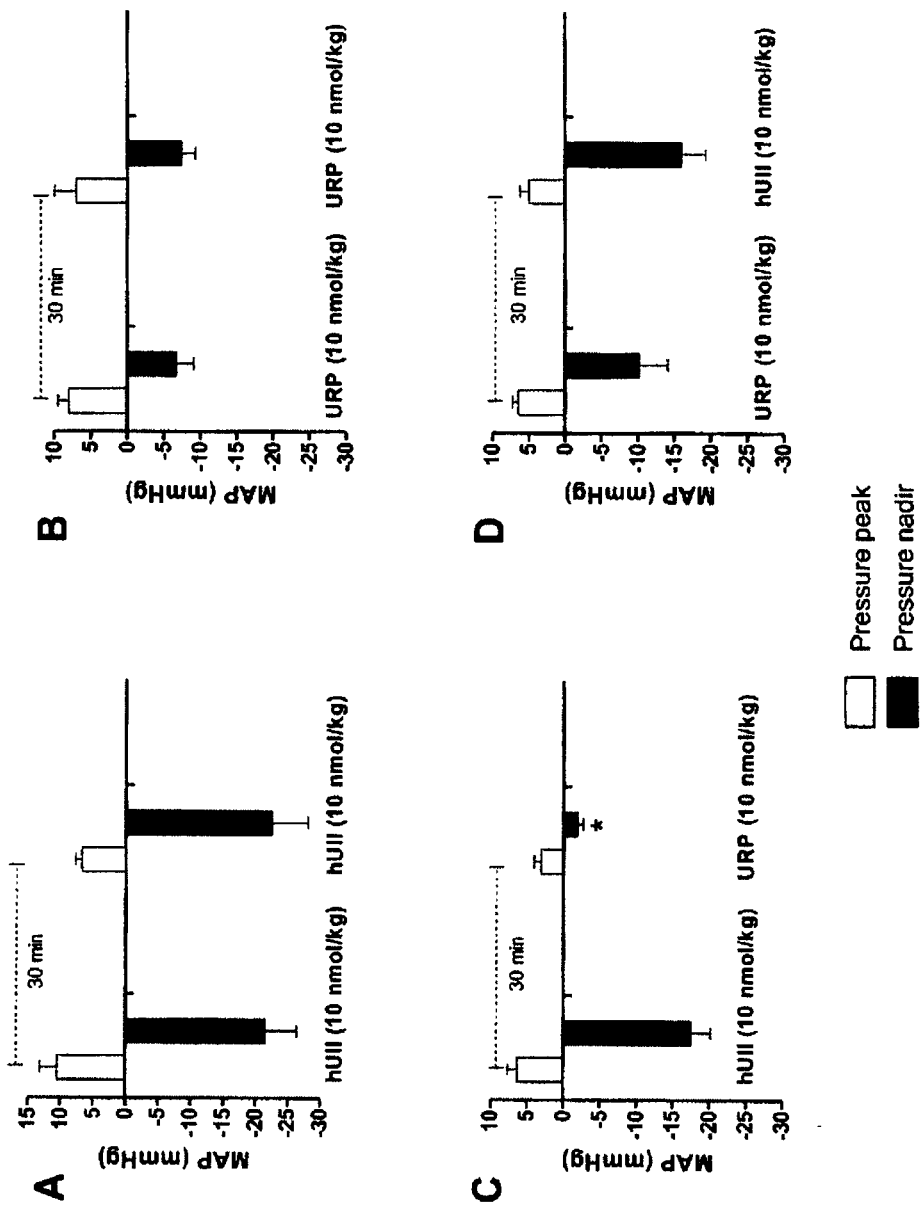
FIG. 9A is an illustration of the effect of repeated hUII injections on hemodynamism in anaesthetized rats.
FIG. 9B and is an illustration of the effect of repeated URP injections on hemodynamism in anaesthetized rats.
FIG. 9C and is an illustration of the effect of hUII on the URP-associated hemodynamic function.
FIG. 9D and is an illustration of the effect of URP on the hUII-associated hemodynamic function. Significant differences (*P<0.05) were determined by unpaired Student t-test. Data represent the mean±S.E.M. and n=4 to 6 animals.

Effect of hUII or URP on hUII and URP Hemodynamic Action in Anaesthetized Rats:

The hypotensive action of UII and URP in anaesthetized rats was previously investigated.[25,26] It was then observed that hUII and URP at a dose of 10 nmol/kg were able to significantly alter the blood pressure. This concentration was therefore used in the present study. As shown in FIG. 9A and FIG. 9B, repeated injections of hUII or URP produced equivalent biphasic responses for the respective peptide. Noteworthy, the URP-associated hemodynamic response was significantly lower than that of hUII. Interestingly, following a single injection of hUII, the hypotensive effect of URP, injected 30 min later, was significantly reduced (FIG. 9C). However, such observation was not made when hUII was administered 30 min after a bolus injection of URP (FIG. 9D).

Figure 10:
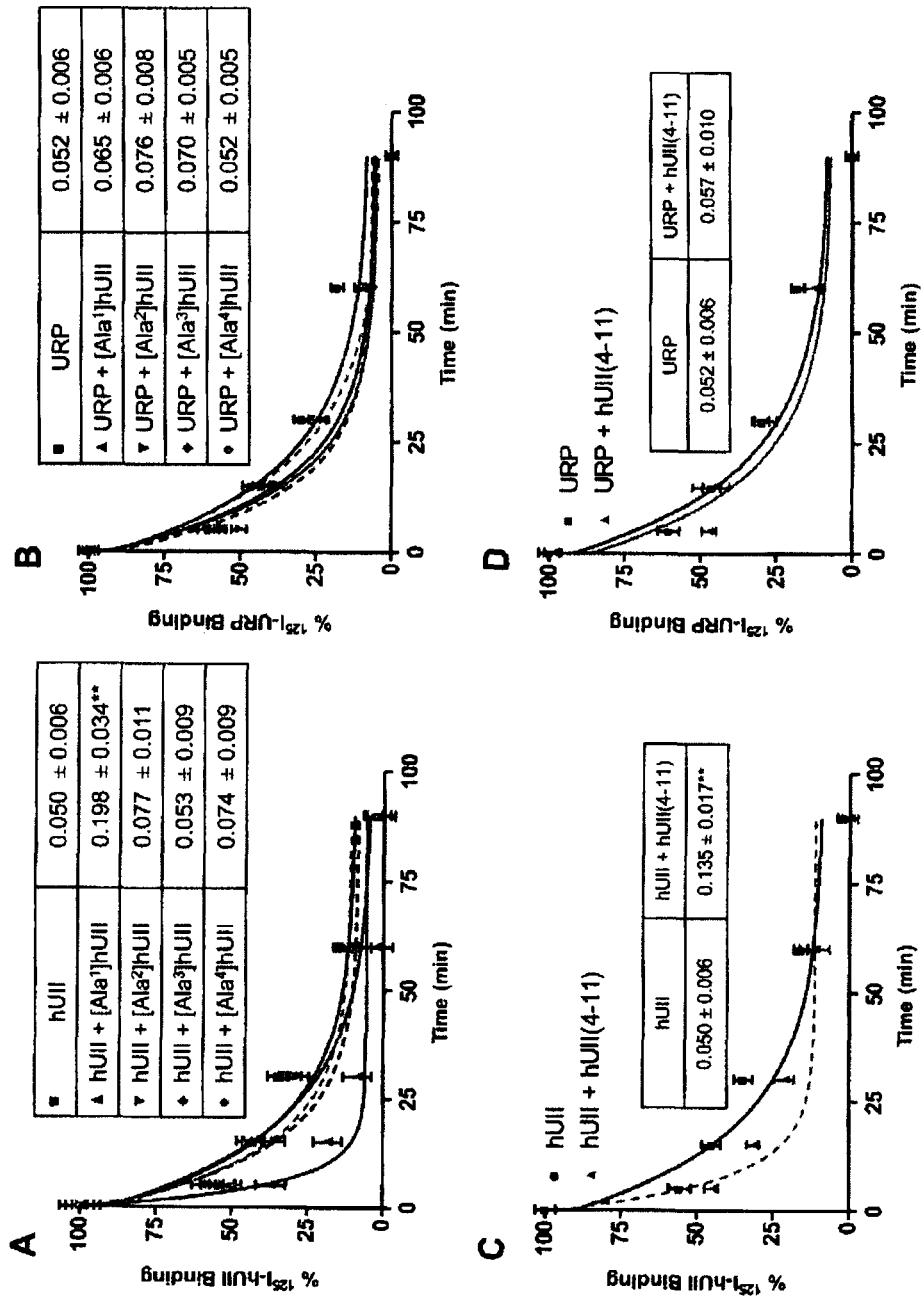
FIG. 10 is an illustration of the impact of Ala-substituted hUII analogs on the dissociation rate of $^{125}$I-hUII (A) and $^{125}$I-URP (B); and the influence of hUII(4-11) on the dissociation rate of $^{125}$I-hUII (C) or $^{125}$I-URP (D). Significant differences (**P<0.01) were determined by unpaired Student t-test.

Insight into Putative Interaction Between hUII and its Cognate Receptor:

As previously reported, replacement of the N-terminal exocyclic residues of hUII by an alanine moiety, i.e. [Ala$^1$]hUII, [Ala$^2$]hUII, [Ala$^3$]hUII, [Ala$^4$]hUII, generated analogs that appeared as very potent ligands of the hUT receptors.[8] Dissociation of the bound radioligand, either $^{125}$I-hUII or $^{125}$I-URP, was initiated by high concentration ($10^{-6}$M) of the corresponding unlabeled peptide in the absence or presence of an Ala-substituted hUII analogs ($10^{-6}$M). As shown, [Ala$^2$]hUII, [Ala$^3$]hUII, [Ala$^4$]hUII had no effect on the dissociation rate of either $^{125}$I-hUII or $^{125}$I-URP (FIG. 10A and FIG. 10B). However, [Ala$^1$]hUII was able to produce a significant variation (P<0.01) of the $^{125}$I-hUII dissociation rate ($k_{off}$=0.050±0.006 versus $k_{off}$=0.198±0.034) suggesting the presence of a specific and mandatory interaction between the residue acidic side chain and the human urotensin II receptor. Moreover, hUII(4-11), considered as the minimal equiactive sequence of hUII, was also able to accelerate the dissociation of $^{125}$I-hUII from the receptor but had no influence on $^{125}$I-URP dissociation kinetic (FIG. 10C and FIG. 10D).

Figure 11:
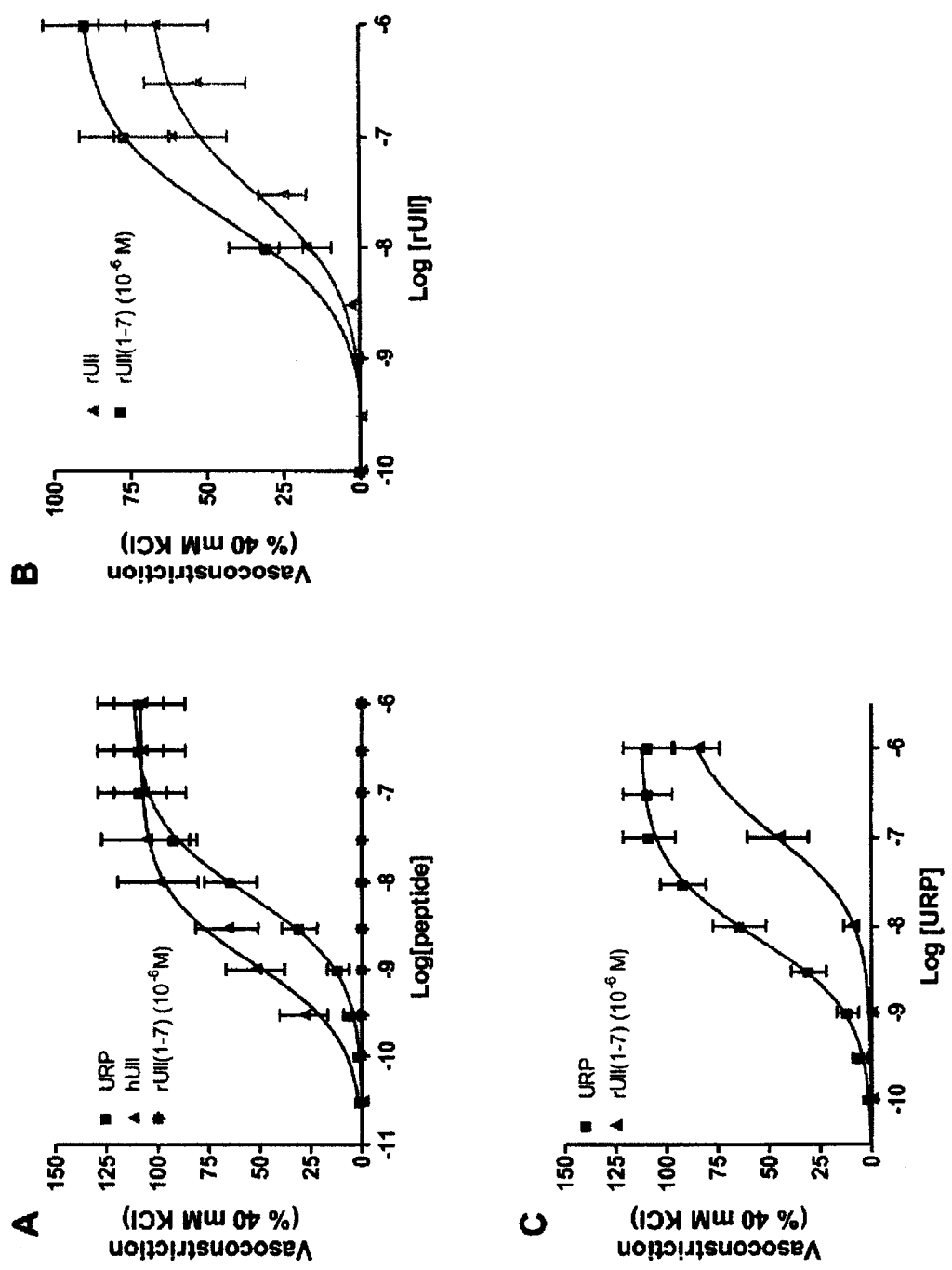
FIG. 11A and is an illustration of the concentration-response curve obtained with rat thoracic aorta rings after adding cumulative concentrations of hUII, URP and rUII(1-7).
FIG. 11B is an illustration of the effects of rUII(1-7) on rUII-induced contraction of rat aortic ring.
FIG. 11C is an illustration of the effects of rUII(1-7) on URP-induced contraction of rat aortic ring. Data represent the mean±S.E.M. and n=5 to 8 animals.

Effect of the N-Terminal Domain of Rat UII on Rat UII- or URP-Induced Rat Aortic Ring Contraction:

Based on the abovementioned putative interaction between UT and the N-terminal segment of UII, the impact of this N-terminal peptide segment on UII- and URP-induced vasoconstriction was investigated. Since the functional bioassay involved the use of rat aortic ring contraction, the homologous N-terminal UII region, i.e. rat UII(1-7), encompassing all the residues adjacent to the cyclic core (Pyr-His-Gly-Thr-Ala-Pro-Glu-amide was used (Table 11). As an agonist, this compound was unable to induce the contraction of rat aortic rings at a concentration up to $10^{-6}$M (FIG. 11A). Pretreatment with rUII(1-7) ($10^{-6}$M, 15 min) did not significantly alter rUII-induced contraction (FIG. 11B). However, a significant rightward shift of the URP-associated (P<0.05) contraction curve under the same condition was observed, suggesting that the N-terminal segment of rUII might act as a competitive and URP-selective antagonist (FIG. 11C).

TABLE 11

Physicochemical properties of rUII(1-7).

| Sequence | | Purity[a] | MS[b] Calc. | MS[b] Found |
|---|---|---|---|---|
| rUII(1-7) | Pyr-His-Gly-Thr-Ala-Pro-Glu-NH$_2$ (SEQ ID NO: 90) | 95% | 720.3 | 721.5 |

[a]Percentage of purity determined by HPLC using the system: A = H$_2$O (0.1% TFA) and B = 60% CH$_3$CN/40% A with a gradient slope of 1% B/min, at a flow rate of 1 mL/min on a Vydac C$_{18}$ column. Detection at 214 nm.
[b]MALDI mass spectral analysis (m/z). The observed [M + H]$^+$ of the monoisotope compared with the calculated m/z monoisotopic mass.

(para-iodo-Phe$^4$]URP (Scheme 1);
(H-Ala-Cys-Phe-Phe(4-I)-Lys-Tyr-Cys-Val-OH) (SEQ ID NO:_91); Purity ≥98%; Ms calc: 1103.31; Ms observed: 1104.1. Percentage purity determined by RP-HPLC using buffer system: A=H$_2$O/0.06% TFA (pH 2.5) and B=60% CH$_3$CN/40% A with a gradient slope of 1% B/min, at flow rate of 1 ml/min on a Vydac C$_{18}$ column (0.21×15 cm, 5 µm particle size, 300 Å pore size). Detection at 214 nm. The observed [M+H]$^+$ of the monoisotope was compared with the calculated m/z monoisotopic mass. Noteworthy, this compound acted as a full agonist of the urotensin II receptor.

Synthesis of [para-iodo-Phe$^4$]URP

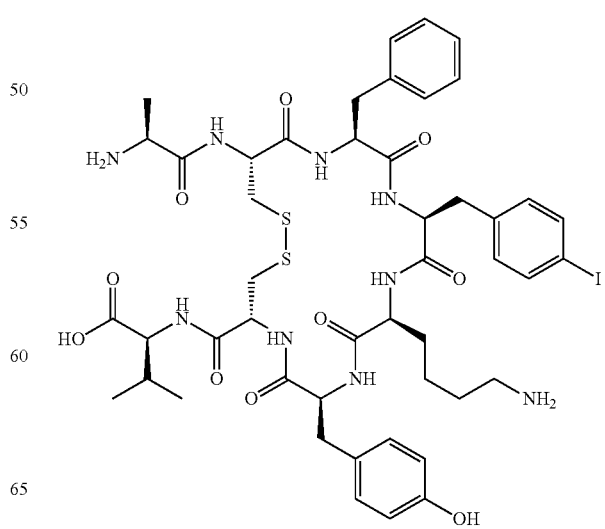

Peptides were manually synthesized on a Wang resin using standard solid phase peptide synthesis using Fmoc chemistry. Main chain assembly was mediated by TBTU/DIPEA and coupling completion was assessed by Kaiser's test (ninhydrin). A three-fold excess of protected amino acid was used based on the original substitution of the Wang resin and Fmoc removal was achieved via piperidine-mediated deprotection. The last amino acid was systematically introduced as a Boc-derivative (Boc-Ala-OH) to prevent the Fmoc removal during the cross-coupling reactions.

General Procedure for the Suzuki-Miyaura Cross-Coupling Reaction (C—C Coupling)[27]

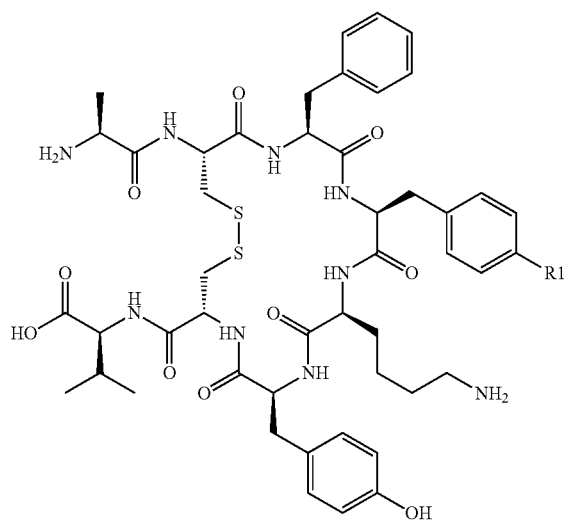

The optimal conditions for carrying out the cross-coupling reactions on the resin supported substrate are as follows: [para-iodo-Phe4]URP-peptidyl-resin (1 eq.), boronic acid (3 eq.), $Na_2CO_3$ (3 eq.) were added to degassed DMF/DCM (1:1, v/v). The mixture was bubbled with argon over a period of 10-15 min after which $Pd(PPh_3)_4$ (0.1 eq.) was added to the reaction mixture. The reaction was stirred over a period ranging from 12 to 24 h at 80° C. The resin was subsequently filtered and after successive washings with DMF (×3), $H_2O$ (×3), MeOH (×2), DMF (×3), and DCM (×3), the peptide-resin was cleaved, cyclized, and purified following the procedure described hereinbelow.

[Bip4]URP; (H-Ala-Cys-Phe-Bip-Lys-Tyr-Cys-Val-OH) (SEQ ID NO:_89); Purity ≥98%; Ms calc: 1053.4; Ms observed: 1053.4. Percentage purity determined by RP-HPLC using buffer system: A=$H_2O$/0.06% TFA (pH 2.5) and B=60% $CH_3CN$/40% A with a gradient slope of 1% B/min, at flow rate of 1 ml/min on a Vydac $C_{18}$ column (0.21×15 cm, 5 μm particle size, 300 Å pore size). Detection at 214 nm. The observed [M+H]+ of the monoisotope was compared with the calculated m/z monoisotopic mass.

General Procedure for the Sonogashira Reaction (C≡C Coupling)[28]

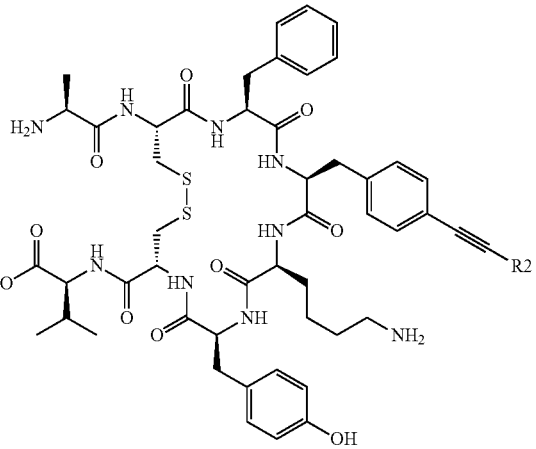

The optimal conditions for carrying out the cross-coupling reactions on the resin supported substrate are as follows: [para-iodo-Phe4]URP-peptidyl-resin (1 eq.), alkyne derivative (3 eq.), CuI (0.1 eq.) and TEA (3 eq.) were added to degassed DMF/DCM (1:1, v/v). The mixture was bubbled with argon over a period of 10-15 min after which $PdCl_2(PPh_3)_2$ (0.1 eq.) and $PCy_3$ (0.3 eq.) were added to the reaction mixture. The reaction was stirred over a period ranging from 12 to 24 h at 40° C. The resin was subsequently filtered and after successive washings with DMF (×3), $H_2O$ (×3), MeOH (×2), DMF (×3), and DCM (×3), the peptide-resin was cleaved, cyclized, and purified following the procedure described hereinbelow.

General Procedure for the Heck Reaction (C═C Coupling)[29]

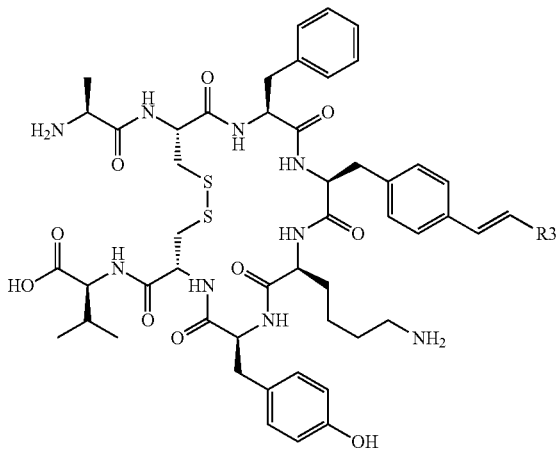

The optimal conditions for carrying out the cross-coupling reactions on the resin supported substrate are as follows: [para-iodo-Phe4]URP-peptidyl-resin (1 eq.), triphenylphosphine (1 eq.), alkene derivative (2 eq.) were added to degassed DMF/water/TEA (85:10:5, v/v/v). The mixture was bubbled with argon over a period of 10-15 min after which $Pd(OAc)_2$ (0.3 eq.) was added to the reaction mixture. The reaction was stirred over a period ranging from 12 to 24 h at 60° C. The resin was subsequently filtered and after successive washings with DMF (×3), H₂O (×3), MeOH (×2), DMF (×3), and DCM (×3), the peptide-resin was cleaved, cyclized, and purified following the procedure described hereinbelow.

Peptide Cleavage, Cyclization and Purification:

All peptides were cleaved from the resin support with simultaneous side-chain deprotection by treatment with TFA containing 1,2-ethanedithiol (2.5%), water (2.5%) and triisopropylsilane (1%) over a period of 1.5 h at room temperature. The diethylether-precipitated crude peptides were solubilized in 70% acetic acid (1 mg/ml) and then cyclized by the addition of iodine (10% solution in methanol) until appearance of a stable orange color. Following an additional 30 min, ascorbic acid was added to quench the excess of iodine. The crude, lyophilized peptides were purified using a preparative reverse-phase HPLC protocol using a linear gradient of 1% B per 2 min increase from the baseline percentage of B (Eluent A=H₂O, 0.1% TFA, Eluent B=60% MeCN/40% A, 0.1% TFA). Homogeneity of the purified fractions was assessed by RP-HPLC and mass spectrometry in linear mode using α-cyanohydroxycinnamic acid as matrix. The pure fractions (>95%) containing the product were pooled and lyophilized.

General Procedure for the Preparation of Radiolabeled URP Derivatives

Peptides were manually synthesized on a Boc-Val-CM resin using standard solid phase peptide synthesis using Boc chemistry. Main chain assembly was mediated by TBTU/DIPEA and coupling completion was assessed by Kaiser's test (ninhydrin). A three-fold excess of protected amino acid was used based on the original substitution of the resin and Boc removal was achieved via TFA-mediated deprotection. To facilitate the anchorage of the chelator moiety, the Lys derivatives was introduced as a Boc-Lys(Fmoc)-OH. Peptide resins were then treated with anhydrous HF in the presence of anisole (5-10%, v/v) at 0° C. for 1.5 h. After elimination of HF under vacuum, the crude peptides were washed with peroxide-free diethyl ether and extracted with 0.1% TFA in 60% acetonitrile/water. After lyophilization, the orthogonally protected peptides were cyclised as previously described and purified using preparative RP-HPLC and two successive solvent systems (Eluent A: TEAP at pH 2.25 and 0.1% TFA, Eluent B: 60% acetonitrile/A). The purified peptides were characterized by analytical RP-HPLC and MALDI-TOF-MS on a Voyager DE using α-cyano-4-hydroxycinnamic acid as matrix. Conjugation of the DOTA-, DTPA-, or NOTA-based chelators was achieved as follows: A solution of chelator-NHS ester (2 eq) in DMF and N,N'-diisopropylethylamine (DIPEA) (3 eq) were added to the peptide solution in dry DMF. The mixture was stirred at room temperature and the progress of the reaction was followed by analytical RP-HPLC. After completion of the reaction, generally observed after 3 h, a preparative RP-HPLC purification was performed yielding the peptide-conjugated analog. Homogeneity of each fraction was assessed by analytical RP-HPLC. Removal of the Fmoc group was achieved through basolytic treatment (20% piperidine in DMF) for 20 min. Following dilution in water, the peptides were once again purified and analyzed as described hereinabove.

DOTA-[Bip⁴]URP: (DOTA-Ala-Cys-Phe-Bip-Lys-Tyr-Cys-Val-OH) (SEQ ID NO:_89); Purity ≥98%; Ms calc.: 1439.6; Ms observed: 1441.1. Percentage purity determined by RP-HPLC using buffer system: A=H₂O/0.06% TFA (pH 2.5) and B=60% CH₃CN/40% A with a gradient slope of 1% B/min, at flow rate of 1 ml/min on a Vydac $C_{18}$ column (0.21×15 cm, 5 μm particle size, 300 Å pore size). Detection at 214 nm. The observed m/z of the monoisotope was compared with the calculated [M+H]⁺ monoisotopic mass.

NOTA-[Bip⁴]URP: (NOTA-Ala-Cys-Phe-Bip-Lys-Tyr-Cys-Val-OH) (SEQ ID NO:_89); Purity ≥98%; Ms calc.: 1338.6; Ms observed: 1339.5. Percentage purity determined by RP-HPLC using buffer system: A=H₂O/0.06% TFA (pH 2.5) and B=60% CH₃CN/40% A with a gradient slope of 1% B/min, at flow rate of 1 ml/min on a Vydac $C_{18}$ column (0.21×15 cm, 5 μm particle size, 300 Å pore size). Detection at 214 nm. The observed m/z of the monoisotope was compared with the calculated [M+H]⁺ monoisotopic mass.

It is to be understood that the specification is not limited in its application to the details of construction and parts as described hereinabove. The specification is capable of other embodiments and of being practiced in various ways. It is also understood that the phraseology or terminology used herein is for the purpose of description and not limitation. Hence, although the present invention has been described hereinabove by way of illustrative embodiments thereof, it can be modified, without departing from the spirit, scope and nature of the subject disclosure as defined in the appended claims.

REFERENCES

1. Ross B, McKendy K, Giaid A. (2010). Role of urotensin II in health and disease. *Am J Physiol Regul Integr Comp Physiol* 298(5): R1156-1172.
2. Vaudry H.; Do Rego, J. C.; Le Mevel J. C.; Chatenet D.; Tostivint H.; Fournier A.; Tonon M. C.; Pelletier G.; Conlon J. M.; Leprince J. Urotensin II, from fish to human. *Ann N Y Acad Sci* 2010, 1200, 53-66.
3. Douglas, S. A., Ohlstein E. H. (2000). Human urotensin-II, the most potent mammalian vasoconstrictor identified to date, as a therapeutic target for the management of cardiovascular disease. *Trends Cardiovasc Med* 10(6): 229-237.
4. Sugo T., Mori M. (2008). Another ligand fishing for G protein-coupled receptor 14. Discovery of urotensin II-related peptide in the rat brain. *Peptides* 29(5): 809-812.
5. Camarda, V.; Guerrini, R.; Kostenis, E.; Rizzi, A.; Calo, G.; Hattenberger, A.; Zucchini, M.; Salvadori, S.; Regoli, D. A new ligand for the urotensin II receptor. *Br J Pharmacol* 2002, 137, 311-4.
6. Chatenet D., Dubessy C., Leprince J., Boularan C., Carlier L., Segalas-Milazzo, I., Guilhaudis, L., Oulyadi, H., Davoust D., Scalbert E., Pfeiffer B., Renard, P., Tonon M. C., Lihrmann I., Pacaud P., Vaudry H. Structure-activity relationships and structural conformation of a novel urotensin II-related peptide. *Peptides* 2004, 25, 1819-1830.
7. Labarrere P., Chatenet D., Leprince J., Marionneau C., Loirand G., Tonon M. C., Dubessy C., Scalbert E., Pfeiffer B., Renard P., Calas B., Pacaud P., Vaudry H. Structure-activity relationships of human urotensin II and related analogues on rat aortic ring contraction. *J Enzyme Inhib Med Chem* 2003, 18, 77-88.
8. Brkovic A., Hattenberger A., Kostenis E., Klabunde T., Flohr S., Kurz M., Bourgault S., Fournier A. Functional and binding characterizations of urotensin II-related peptides in human and rat urotensin II-receptor assay. *J Pharmacol Exp Ther* 2003, 306, 1200-9.
9. Leprince J.; Chatenet D.; Dubessy C.; Fournier A.; Pfeiffer B.; Scalbert E.; Renard P.; Pacaud P.; Oulyadi H.; Segalas-Milazzo I.; Guilhaudis L.; Davoust D.; Tonon M. C.; Vaudry H. Structure-activity relationships of urotensin II and URP. *Peptides* 2008, 29, 658-73.
10. Krum H., Kemp W. (2007). Therapeutic potential of blockade of the urotensin II system in systemic hypertension. *Curr Hypertens Rep* 9(1): 53-58.
11. Watson A. M., Lambert G. W., Smith K. J., May C. N. (2003). Urotensin II acts centrally to increase epinephrine and ACTH release and cause potent inotropic and chronotropic actions. *Hypertension* 42(3): 373-379.
12. Song W., Abdel-Razik A. E., Lu W., Ao Z., Johns D. G., Douglas S. A. (2006). Urotensin II and renal function in the rat. *Kidney Int* 69(8): 1360-1368.
13. Dai H. Y., Kang W. Q., Wang X., Yu X. J., Li Z. H., Tang M. X. (2007). The involvement of transforming growth factor-beta1 secretion in urotensin II-induced collagen synthesis in neonatal cardiac fibroblasts. *Regul Pept* 140 (1-2): 88-93.
14. Zhang Y. G., Li J., Li Y. G., Wei R. H. (2008). Urotensin II induces phenotypic differentiation, migration, and collagen synthesis of adventitial fibroblasts from rat aorta. *J Hypertens* 26(6): 1119-1126.
15. Shiraishi Y., Watanabe T., Suguro T., Nagashima M., Kato R., Hongo S. (2008). Chronic urotensin II infusion enhances macrophage foam cell formation and atherosclerosis in apolipoprotein E-knockout mice. *J Hypertens* 26(10): 1955-1965.
16. Papadopoulos P., Bousette N., Giaid A. (2008). Urotensin-II and cardiovascular remodeling. *Peptides* 29(5): 764-769.
17. Guidolin D., Albertin G., Ribatti D. (2010). Urotensin-II as an angiogenic factor. *Peptides* 31(6): 1219-1224.
18. Silvestre R. A., Egido E. M., Hernandez R., Leprince J., Chatenet D., Tollemer H. (2004). Urotensin-II is present in pancreatic extracts and inhibits insulin release in the perfused rat pancreas. *Eur J Endocrinol* 151(6): 803-809.
19. Jarry M., Diallo M., Lecointre C., Desrues L., Tokay T., Chatenet D. (2010). The vasoactive peptides urotensin II and urotensin II-related peptide regulate astrocyte activity through common and distinct mechanisms: involvement in cell proliferation. *Biochem J* 428(1): 113-124.
20. Prosser H. C., Forster M. E., Richards A. M., Pemberton C. J. (2008). Urotensin II and urotensin II-related peptide (URP) in cardiac ischemia-reperfusion injury. *Peptides* 29(5): 770-777.
21. Doan N. G., Nguyen T. T. M., Lètourneau M., Turcotte K., Fournier A., Chatenet D. (2011). Biochemical and Pharmacological Characterization of Nuclear Urotensin II Binding Sites in Rat Heart. *Br J Pharmacol*: 166(1):243.
22. Hirose T., Takahashi K., Mori N., Nakayama T., Kikuya M., Ohkubo T. (2009). Increased expression of urotensin II, urotensin II-related peptide and urotensin II receptor mRNAs in the cardiovascular organs of hypertensive rats: comparison with endothelin-1. *Peptides* 30(6): 1124-1129.
23. Maryanoff B. E., Kinney W. A. (2010). Urotensin-II receptor modulators as potential drugs. *J Med Chem* 53(7): 2695-2708.
24. Behm D. J., Herold C. L., Ohlstein E. H., Knight, S. D., Dhanak D., Douglas S. A. Pharmacological characterization of SB-710411 (Cpa-c[D-Cys-Pal-D-Trp-Lys-Val-Cys]-Cpa-amide), a novel peptidic urotensin-II receptor antagonist. *Br J Pharmacol* 2002, 137, 449-58.
25. Hassan G. S., Chouiali F., Saito T., Hu F., Douglas S. A., Ao Z., (2003). Effect of human urotensin-II infusion on hemodynamics and cardiac function. *Can J Physiol Pharmacol* 81(2): 125-128.
26. Sugo T., Murakami Y., Shimomura Y., Harada M., Abe M., Ishibashi Y. (2003). Identification of urotensin II-related peptide as the urotensin II-immunoreactive molecule in the rat brain. *Biochem Biophys Res Commun* 310(3): 860-868.
27. Doan N. D., Bourgault S., Letourneau M., Fournier A. Effectiveness of the Suzuki-Miyaura cross-coupling reaction for solid-phase peptide modification. *J Comb Chem* 2008, 10, 44-51.
28. Hoffmanns U., Metzler-Nolte N. Use of the Sonogashira coupling reaction for the "two-step" labelling of phenylalanine peptide side chains with organometallic compounds. *Bioconjug Chem* 2006, 17, 204-13.
29. Kodama K., Fukuzawa S., Nakayama H., Sakamoto K., Kigawa T., Yabuki T., Matsuda N., Shirouzu M.; Takio K., Yokoyama S., Tachibana K. Site-specific functionalization of proteins by organopalladium reactions. *Chembiochem* 2007, 8, 232-8.
30. Batuwangala M., Camarda V., McDonald J., Marzola E., Lambert D. G., Ng L. L., Calo G., Regoli D., Trapella C., Guerrini R., Salvadori S. Structure-activity relationship study on Tyr9 of urotensin-II(4-11): identification of a partial agonist of the UT receptor. *Peptides* 2009, 30, 1130-6.
31. Gendron G., Gobeil F., Jr.; Belanger S., Gagnon S., Regoli D., D'Orleans-Juste P. Urotensin II-induced hypotensive responses in Wistar-Kyoto (Wky) and spontaneously hypertensive (Shr) rats. *Peptides* 2005, 26, 1468-74.
32. Dubessy C.; Cartier D.; Lectez B.; Bucharles C.; Chartrel N.; Montero-Hadjadje M.; Bizet P.; Chatenet D.; Tostivint H.; Scalbert E.; Leprince J.; Vaudry H.; Jegou S.; Lihrmann I. Characterization of urotensin II, distribution of urotensin II, urotensin II-related peptide and UT receptor mRNAs in mouse: evidence of urotensin II at the neuromuscular junction. *J Neurochem* 2008, 107, 361-74.

What is claimed is:

1. A urotensinergic agent or a pharmaceutically acceptable salt thereof having the formula:

(SEQ ID NO: 37)

Ala-Cys-Phe-X-Lys-Tyr-Cys-Val, wherein X is a L- or D-amino acid selected from the group consisting of glycine, serine, threonine, cysteine, valine, leucine, isoleucine, methionine, proline, phenylalanine, tyrosine, aspartic acid, glutamic acid, asparagine, glutamine, histidine, lysine, arginine and side-chain conformationally constrained phenylalanines, wherein the conformationally constrained phenylalanines are selected from the group consisting of β-β-diphenylalanine and 4-amino-indolo[2,3-c]azepin-3-one, or a phenylalanine analogue having the formula:

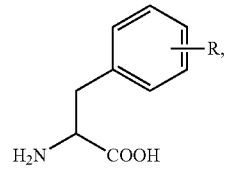

wherein R is a substituent introduced by metal catalysed reaction using a boronic acid, a boronic acid derivative, a substituted vinyl, or a substituted alkynyl.

2. The urotensinergic agent or a pharmaceutically acceptable salt thereof as defined in claim 1, wherein the boronic acid derivative is selected from the group consisting of phenylboronic acid, 4-hydroxyphenylboronic acid, 4-methoxycarbonylphenylboronic acid, 4-pyridineboronic acid, 4-cyanophenylboronic acid, 4-(hydroxymethyl)phenylboronic acid, 3-furanboronic acid, 2-furanboronic acid, 3-thiophenboronic acid, 3-nitro-phenylboronic acid, trans-2-chloromethylvinylboronic acid, trans-1-propen-1-ylboronic acid, 2-tert-butyloxycarbonyl (Boc)-indoleboronic acid, acetamidophenylboronic acid, 4-(N-Boc-amino)phenylboronic acid, 4-phenoxyphenylboronic acid, 4-acetylphenylboronic acid and 2,4,6-trifluorophenylboronic acid.

3. The urotensinergic agent or a pharmaceutically acceptable salt thereof as defined in claim 1, wherein the substituted vinyl is selected from the group consisting of vinylbenzene, 1-methyl-4-vinylbenzene, 1-methyl-3-vinylbenzene, 1-methyl-2-vinylbenzene, 1,3,5-trimethyl-2-vinylbenzene, 1-vinylnaphthalene, 2-vinylnaphthalene, 1-isopropyl-4-vinylbenzene, 1-(chloromethyl)-4-vinylbenzene, 1-chloro-4-vinylbenzene, 3-vinylbenzene, 4-vinylbenzoic acid, 1-(trifluoromethyl)-2-vinylbenzene, 1-(trifluoromethyl)-4-vinylbenzene, 1-(trifluoromethyl)-3-vinylbenzene, isopropenylbenzene, 4-nitrostyrene, 4-vinylalanine, 4-vinylanisole, 1-tert-butoxy-4-vinylbenzene, 4-vinylphenyl acetate and 1-ethoxy-4-vinylbenzene.

4. The urotensinergic agent or a pharmaceutically acceptable salt thereof as defined in claim 1, wherein the substituted alkynyl is selected from the group consisting of ethynylbenzene, 1-ethynyl-4-fluorobenzene, 1-ethynyl-4-tert-butylbenzene, 1-ethynyl-4-methoxy-2-methylbenzene, ethynylcyclohexane, 1-decyne, 9-ethynylphenanthrene, 1-ethynylnaphthalene, 4-ethynylbenzonitrile, 1-ethynyl-4-(trifluoromethyl)benzene, 4-ethynylaniline and 4-ethynyl-1,1'-biphenyl.

5. The urotensinergic agent or a pharmaceutically acceptable salt thereof as defined in claim 1 having the formula:

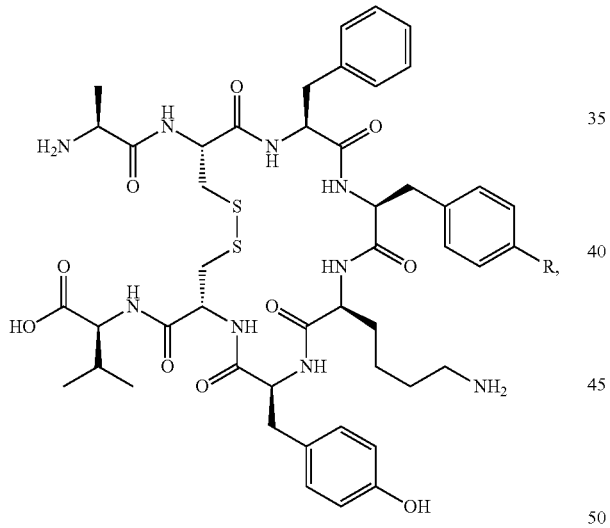

wherein R is a substituent introduced by metal catalysed reaction using a boronic acid or a boronic acid derivative selected from the group consisting of phenylboronic acid, 4-hydroxyphenylboronic acid, 4-methoxycarbonylphenylboronic acid, 4-pyridineboronic acid, 4-cyanophenylboronic acid, 4-(hydroxymethyl)phenylboronic acid, 3-furanboronic acid, 2-furanboronic acid, 3-thiophenboronic acid, 3-nitro-phenylboronic acid, trans-2-chloromethylvinylboronic acid, trans-1-propen-1-ylboronic acid, 2-tert-butyloxycarbonyl (Boc)-indoleboronic acid, acetamidophenylboronic acid, 4-(N-Boc-amino)phenylboronic acid, 4-phenoxyphenylboronic acid, 4-acetylphenylboronic acid and 2,4,6-trifluorophenylboronic acid.

6. The urotensinergic agent or a pharmaceutically acceptable salt thereof as defined in claim 1 having the formula:

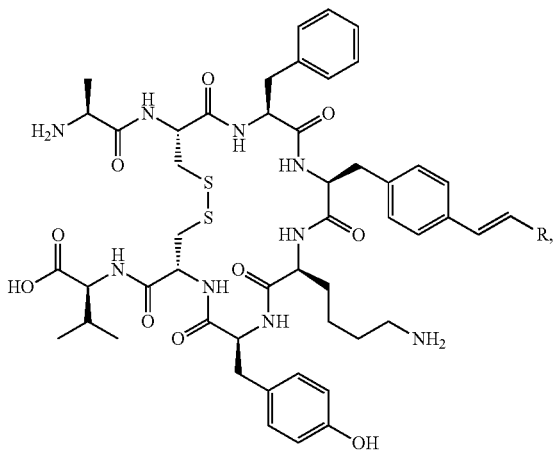

wherein the substituted vinyl (R—C=C—) is introduced by metal catalysed reaction using a substituted vinyl selected from the group consisting of vinylbenzene, 1-methyl-4-vinylbenzene, 1-methyl-3-vinylbenzene, 1-methyl-2-vinylbenzene, 1,3,5-trimethyl-2-vinylbenzene, 1-vinylnaphthalene, 2-vinylnaphthalene, 1-isopropyl-4-vinylbenzene, 1-(chloromethyl)-4-vinylbenzene, 1-chloro-4-vinylbenzene, 3-vinylbenzene, 4-vinylbenzoic acid, 1-(trifluoromethyl)-2-vinylbenzene, 1-(trifluoromethyl)-4-vinylbenzene, 1-(trifluoromethyl)-3-vinylbenzene, isopropenylbenzene, 4-nitrostyrene, 4-vinylalanine, 4-vinylanisole, 1-tert-butoxy-4-vinylbenzene, 4-vinylphenyl acetate and 1-ethoxy-4-vinylbenzene.

7. The urotensinergic agent or a pharmaceutically acceptable salt thereof as defined in claim 1 having the formula:

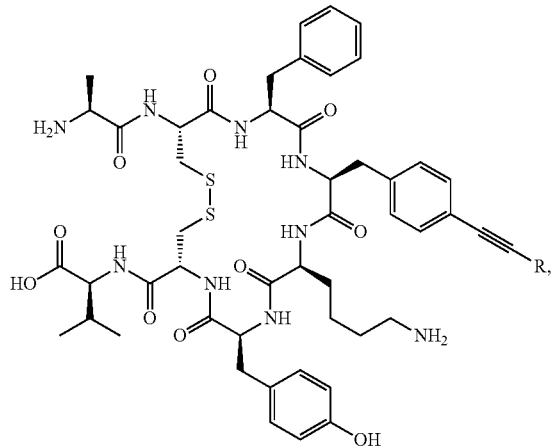

wherein the substituted alkynyl (R—C≡C—) is introduced by metal catalysed reaction using a substituted alkynyl selected from the group consisting of ethynylbenzene, 1-ethynyl-4-fluorobenzene, 1-ethynyl-4-tert-butylbenzene, 1-ethynyl-4-methoxy-2-methylbenzene, ethynylcyclohexane, 1-decyne, 9-ethynylphenanthrene, 1-ethynylnaphthalene, 4-ethynylbenzonitrile, 1-ethynyl-4-(trifluoromethyl)benzene, 4-ethynylaniline, and 4-ethynyl-1,1'-biphenyl.

8. The urotensinergic agent or a pharmaceutically acceptable salt thereof as defined in claim 5 having the formula:

9. A radiolabelled urotensinergic agent having the formula:

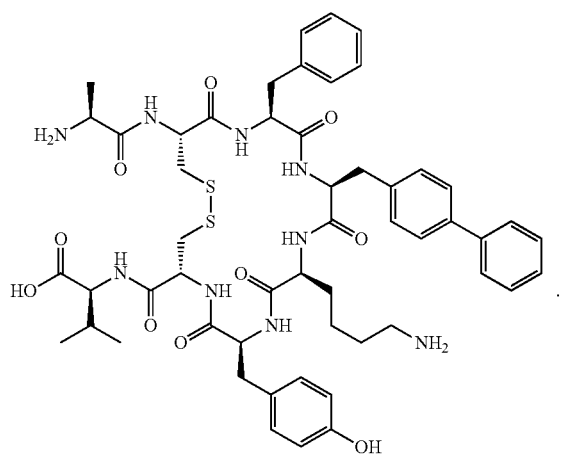

wherein R is a substituent introduced by metal catalysed reaction using a boronic acid or a boronic acid derivative selected from the group consisting of phenylboronic acid, 4-hydroxyphenylboronic acid, 4-methoxycarbonylphenylboronic acid, 4-pyridineboronic acid, 4-cyanophenylboronic acid, 4-(hydroxymethyl)phenylboronic acid, 3-furanboronic acid, 2-furanboronic acid, 3-thiophenboronic acid, 3-nitro-phenylboronic acid, trans-2-chloromethylvinylboronic acid, trans-1-propen-1-ylboronic acid, 2-tert-butyloxycarbonyl (Boc)-indoleboronic acid, acetamidophenylboronic acid, 4-(N-Boc-amino)phenylboronic acid, 4-phenoxyphenylboronic acid, 4-acetylphenylboronic acid and 2,4,6-trifluorophenylboronic acid; and wherein Z is a ligand comprising a radioisotope.

10. The radiolabelled urotensinergic agent as defined in claim 9, wherein the radioisotope is selected from the group consisting of $I^{123}$, $I^{125}$, $I^{131}$, $^{99m}Tc$, $^{161}Tb$, $^{177}Lu$, $^{18}F$, $^{68}Ga$, $^{62}Cu$, $^{111}In$, $^{186}Re$, $^{188}Re$, $^{90}Y$, $^{212}Bi$, $^{211}At$, $^{89}Sr$, $^{166}Ho$, $^{153}Sm$, $^{67}Cu$, $^{64}Cu$ and $Br^{76}$.

11. A radiolabelled urotensinergic agent having the formula:

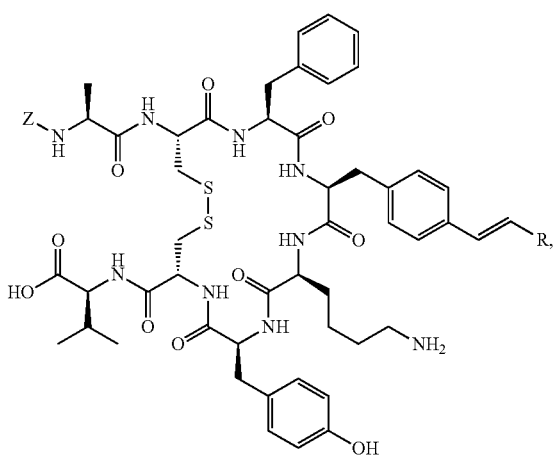

wherein the substituted vinyl (R—C═C—) is introduced by metal catalysed reaction using a substituted vinyl selected from the group consisting of vinylbenzene, 1-methyl-4-vinylbenzene, 1-methyl-3-vinylbenzene, 1-methyl-2-vinylbenzene, 1,3,5-trimethyl-2-vinylbenzene, 1-vinylnaphthalene, 2-vinylnaphthalene, 1-isopropyl-4-vinylbenzene, 1-(chloromethyl)-4-vinylbenzene, 1-chloro-4-vinylbenzene, 3-vinylbenzene, 4-vinylbenzoic acid, 1-(trifluoromethyl)-2-vinylbenzene, 1-(trifluoromethyl)-4-vinylbenzene, 1-(trifluoromethyl)-3-vinylbenzene, isopropenylbenzene, 4-nitrostyrene, 4-vinylalanine, 4-vinylanisole, 1-tert-butoxy-4-vinylbenzene, 4-vinylphenyl acetate and 1-ethoxy-4-vinylbenzene; and wherein Z is a ligand comprising a radioisotope.

12. The radiolabelled urotensinergic agent as defined in claim 11, wherein the radioisotope is selected from the group consisting of $I^{123}$, $I^{125}$, $I^{131}$, $^{99m}Tc$, $^{161}Tb$, $^{177}Lu$, $^{18}F$, $^{68}Ga$, $^{62}Cu$, $^{111}In$, $^{186}Re$, $^{188}Re$, $^{90}Y$, $^{212}Bi$, $^{211}At$, $^{89}Sr$, $^{166}Ho$, $^{153}Sm$, $^{67}Cu$, $^{64}Cu$ and $Br^{76}$.

13. A radiolabelled urotensinergic agent having the formula:

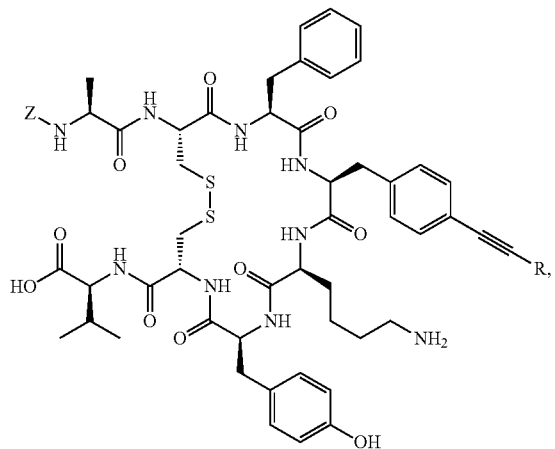

wherein the substituted alkynyl (R—C≡C—) is introduced by metal catalysed reaction using a substituted alkynyl selected from the group consisting of ethynylbenzene, 1-ethynyl-4-fluorobenzene, 1-ethynyl-4-tert-butylbenzene, 1-ethynyl-4-methoxy-2-methylbenzene, ethynylcyclohexane, 1-decyne, 9-ethynylphenanthrene, 1-ethynylnaphthalene, 4-ethynylbenzonitrile, 1-ethynyl-4-(trifluoromethyl)benzene, 4-ethynylaniline and 4-ethynyl-1,1'-biphenyl; and wherein Z is a ligand comprising a radioisotope.

14. The radiolabelled urotensinergic agent as defined in claim 13, wherein the radioisotope is selected from the group consisting of $I^{123}$, $I^{125}$, $I^{131}$, $^{99m}Tc$, $^{161}Tb$, $^{177}Lu$, $^{18}F$, $^{68}Ga$, $^{62}Cu$, $^{111}In$, $^{186}Re$, $^{188}Re$, $^{90}Y$, $^{212}Bi$, $^{211}At$, $^{89}Sr$, $^{166}Ho$, $^{153}Sm$, $^{67}Cu$, $^{64}Cu$ and $Br^{76}$.

15. A method for discriminating between specific biological action mediated by urotensin II (UII) and urotensin II related peptide (URP) comprising the steps of:
  a) exposing aortic rings to a urotensinergic agent as defined in claim 1;
  b) preparing concentration-response curves to UII and URP; and
  c) evaluating the effect of the urotensinergic agent on aortic ring contraction induced by UII and URP.

* * * * *

SEQUENCE LISTING

<160> NUMBER OF SEQ ID NOS: 92

<210> SEQ ID NO 1
<211> LENGTH: 12
<212> TYPE: PRT
<213> ORGANISM: Lamprey

<400> SEQUENCE: 1

Asn Asn Phe Ser Asp Cys Phe Trp Lys Tyr Cys Val
1               5                   10

<210> SEQ ID NO 2
<211> LENGTH: 12
<212> TYPE: PRT
<213> ORGANISM: Fugu

<400> SEQUENCE: 2

```
Thr Gly Asn Asn Glu Cys Phe Trp Lys Tyr Cys Val
1               5                   10

<210> SEQ ID NO 3
<211> LENGTH: 12
<212> TYPE: PRT
<213> ORGANISM: Skate

<400> SEQUENCE: 3

Asn Asn Phe Ser Asp Cys Phe Trp Lys Tyr Cys Val
1               5                   10

<210> SEQ ID NO 4
<211> LENGTH: 12
<212> TYPE: PRT
<213> ORGANISM: Dogfish

<400> SEQUENCE: 4

Asn Asn Phe Ser Asp Cys Phe Trp Lys Tyr Cys Val
1               5                   10

<210> SEQ ID NO 5
<211> LENGTH: 12
<212> TYPE: PRT
<213> ORGANISM: Sturgeon

<400> SEQUENCE: 5

Gly Ser Thr Ser Glu Cys Phe Trp Lys Tyr Cys Val
1               5                   10

<210> SEQ ID NO 6
<211> LENGTH: 12
<212> TYPE: PRT
<213> ORGANISM: Paddlefish

<400> SEQUENCE: 6

Gly Ser Thr Ser Glu Cys Phe Trp Lys Tyr Cys Val
1               5                   10

<210> SEQ ID NO 7
<211> LENGTH: 12
<212> TYPE: PRT
<213> ORGANISM: Goby

<400> SEQUENCE: 7

Ala Gly Thr Ala Asp Cys Phe Trp Lys Tyr Cys Val
1               5                   10

<210> SEQ ID NO 8
<211> LENGTH: 12
<212> TYPE: PRT
<213> ORGANISM: Zebrafish Alpha

<400> SEQUENCE: 8

Gly Gly Gly Ala Asp Cys Phe Trp Lys Tyr Cys Val
1               5                   10

<210> SEQ ID NO 9
<211> LENGTH: 12
<212> TYPE: PRT
<213> ORGANISM: Zebrafish Beta

<400> SEQUENCE: 9

Gly Ser Asn Thr Glu Cys Phe Trp Lys Tyr Cys Val
1               5                   10
```

<210> SEQ ID NO 10
<211> LENGTH: 12
<212> TYPE: PRT
<213> ORGANISM: Sucker A

<400> SEQUENCE: 10

Gly Ser Gly Ala Asp Cys Phe Trp Lys Tyr Cys Val
1               5                   10

<210> SEQ ID NO 11
<211> LENGTH: 12
<212> TYPE: PRT
<213> ORGANISM: Sucker B

<400> SEQUENCE: 11

Gly Ser Asn Thr Glu Cys Phe Trp Lys Tyr Cys Val
1               5                   10

<210> SEQ ID NO 12
<211> LENGTH: 12
<212> TYPE: PRT
<213> ORGANISM: Carp Alpha

<400> SEQUENCE: 12

Gly Gly Gly Ala Asp Cys Phe Trp Lys Tyr Cys Val
1               5                   10

<210> SEQ ID NO 13
<211> LENGTH: 12
<212> TYPE: PRT
<213> ORGANISM: Carp Beta1

<400> SEQUENCE: 13

Gly Gly Asn Thr Glu Cys Phe Trp Lys Tyr Cys Val
1               5                   10

<210> SEQ ID NO 14
<211> LENGTH: 12
<212> TYPE: PRT
<213> ORGANISM: Carp Beta2

<400> SEQUENCE: 14

Gly Ser Asn Thr Glu Cys Phe Trp Lys Tyr Cys Val
1               5                   10

<210> SEQ ID NO 15
<211> LENGTH: 12
<212> TYPE: PRT
<213> ORGANISM: Carp Gamma

<400> SEQUENCE: 15

Gly Gly Gly Ala Asp Cys Phe Trp Lys Tyr Cys Val
1               5                   10

<210> SEQ ID NO 16
<211> LENGTH: 12
<212> TYPE: PRT
<213> ORGANISM: Flounder

<400> SEQUENCE: 16

Ala Gly Thr Thr Glu Cys Phe Trp Lys Tyr Cys Val
1               5                   10

```
<210> SEQ ID NO 17
<211> LENGTH: 12
<212> TYPE: PRT
<213> ORGANISM: Trout

<400> SEQUENCE: 17

Gly Gly Asn Ser Glu Cys Phe Trp Lys Tyr Cys Val
1               5                   10

<210> SEQ ID NO 18
<211> LENGTH: 12
<212> TYPE: PRT
<213> ORGANISM: Grouper

<400> SEQUENCE: 18

Ala Gly Asn Ser Glu Cys Phe Trp Lys Tyr Cys Val
1               5                   10

<210> SEQ ID NO 19
<211> LENGTH: 13
<212> TYPE: PRT
<213> ORGANISM: Frog

<400> SEQUENCE: 19

Ala Gly Asn Leu Ser Glu Cys Phe Trp Lys Tyr Cys Val
1               5                   10

<210> SEQ ID NO 20
<211> LENGTH: 12
<212> TYPE: PRT
<213> ORGANISM: Chicken

<400> SEQUENCE: 20

Gly Asn Leu Ser Glu Cys Phe Trp Lys Tyr Cys Val
1               5                   10

<210> SEQ ID NO 21
<211> LENGTH: 12
<212> TYPE: PRT
<213> ORGANISM: Zebra finch

<400> SEQUENCE: 21

Gly Asn Leu Ser Glu Cys Phe Trp Lys Tyr Cys Val
1               5                   10

<210> SEQ ID NO 22
<211> LENGTH: 17
<212> TYPE: PRT
<213> ORGANISM: Mouse

<400> SEQUENCE: 22

Gln His Lys Gln His Gly Ala Ala Pro Glu Cys Phe Trp Lys Tyr Cys
1               5                   10                  15

Ile

<210> SEQ ID NO 23
<211> LENGTH: 14
<212> TYPE: PRT
<213> ORGANISM: Rat

<400> SEQUENCE: 23

Gln His Gly Thr Ala Pro Glu Cys Phe Trp Lys Tyr Cys Ile
1               5                   10
```

```
<210> SEQ ID NO 24
<211> LENGTH: 12
<212> TYPE: PRT
<213> ORGANISM: Porcine A

<400> SEQUENCE: 24

Gly Pro Thr Ser Glu Cys Phe Trp Lys Tyr Cys Val
1               5                   10

<210> SEQ ID NO 25
<211> LENGTH: 12
<212> TYPE: PRT
<213> ORGANISM: Porcine B

<400> SEQUENCE: 25

Gly Pro Pro Ser Glu Cys Phe Trp Lys Tyr Cys Val
1               5                   10

<210> SEQ ID NO 26
<211> LENGTH: 12
<212> TYPE: PRT
<213> ORGANISM: Cattle

<400> SEQUENCE: 26

Gly Pro Ser Ser Glu Cys Phe Trp Lys Tyr Cys Val
1               5                   10

<210> SEQ ID NO 27
<211> LENGTH: 11
<212> TYPE: PRT
<213> ORGANISM: Monkey

<400> SEQUENCE: 27

Glu Thr Pro Asp Cys Phe Trp Lys Tyr Cys Val
1               5                   10

<210> SEQ ID NO 28
<211> LENGTH: 11
<212> TYPE: PRT
<213> ORGANISM: Chimpanzee

<400> SEQUENCE: 28

Glu Thr Pro Asp Cys Phe Trp Lys Tyr Cys Val
1               5                   10

<210> SEQ ID NO 29
<211> LENGTH: 11
<212> TYPE: PRT
<213> ORGANISM: Human

<400> SEQUENCE: 29

Glu Thr Pro Asp Cys Phe Trp Lys Tyr Cys Val
1               5                   10

<210> SEQ ID NO 30
<211> LENGTH: 10
<212> TYPE: PRT
<213> ORGANISM: Zebrafish

<400> SEQUENCE: 30

Val Cys Phe Trp Lys Tyr Cys Ser Gln Asn
1               5                   10

<210> SEQ ID NO 31
<211> LENGTH: 8
```

```
<212> TYPE: PRT
<213> ORGANISM: Chicken

<400> SEQUENCE: 31

Ala Cys Phe Trp Lys Tyr Cys Ile
1               5

<210> SEQ ID NO 32
<211> LENGTH: 8
<212> TYPE: PRT
<213> ORGANISM: Mouse

<400> SEQUENCE: 32

Ala Cys Phe Trp Lys Tyr Cys Val
1               5

<210> SEQ ID NO 33
<211> LENGTH: 8
<212> TYPE: PRT
<213> ORGANISM: Rat

<400> SEQUENCE: 33

Ala Cys Phe Trp Lys Tyr Cys Val
1               5

<210> SEQ ID NO 34
<211> LENGTH: 8
<212> TYPE: PRT
<213> ORGANISM: Horse

<400> SEQUENCE: 34

Ala Cys Phe Trp Lys Tyr Cys Val
1               5

<210> SEQ ID NO 35
<211> LENGTH: 8
<212> TYPE: PRT
<213> ORGANISM: Chimpanzee

<400> SEQUENCE: 35

Ala Cys Phe Trp Lys Tyr Cys Val
1               5

<210> SEQ ID NO 36
<211> LENGTH: 8
<212> TYPE: PRT
<213> ORGANISM: Homo Sapien

<400> SEQUENCE: 36

Ala Cys Phe Trp Lys Tyr Cys Val
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is an L-or D-amino acid selected from the
      group consisting of G, A, S, T, C, V, L, I, M, P, F, Y, W, D, E,
      N, Q, H, K, R and side-chain conformationally restricted
      phenylalanines

<400> SEQUENCE: 37
```

Ala Cys Phe Xaa Lys Tyr Cys Val
1               5

<210> SEQ ID NO 38
<211> LENGTH: 5
<212> TYPE: PRT
<213> ORGANISM: Lamprey

<400> SEQUENCE: 38

Asn Asn Phe Ser Asp
1               5

<210> SEQ ID NO 39
<211> LENGTH: 5
<212> TYPE: PRT
<213> ORGANISM: Fugu

<400> SEQUENCE: 39

Thr Gly Asn Asn Glu
1               5

<210> SEQ ID NO 40
<211> LENGTH: 5
<212> TYPE: PRT
<213> ORGANISM: Skate

<400> SEQUENCE: 40

Asn Asn Phe Ser Asp
1               5

<210> SEQ ID NO 41
<211> LENGTH: 5
<212> TYPE: PRT
<213> ORGANISM: Dogfish

<400> SEQUENCE: 41

Asn Asn Phe Ser Asp
1               5

<210> SEQ ID NO 42
<211> LENGTH: 5
<212> TYPE: PRT
<213> ORGANISM: Sturgeon

<400> SEQUENCE: 42

Gly Ser Thr Ser Glu
1               5

<210> SEQ ID NO 43
<211> LENGTH: 5
<212> TYPE: PRT
<213> ORGANISM: Paddlefish

<400> SEQUENCE: 43

Gly Ser Thr Ser Glu
1               5

<210> SEQ ID NO 44
<211> LENGTH: 5
<212> TYPE: PRT
<213> ORGANISM: Goby

<400> SEQUENCE: 44

Ala Gly Thr Ala Asp

```
1               5
```

```
<210> SEQ ID NO 45
<211> LENGTH: 5
<212> TYPE: PRT
<213> ORGANISM: Zebrafish alpha

<400> SEQUENCE: 45

Gly Gly Gly Ala Asp
1               5

<210> SEQ ID NO 46
<211> LENGTH: 5
<212> TYPE: PRT
<213> ORGANISM: Zebrafish beta

<400> SEQUENCE: 46

Gly Ser Asn Thr Glu
1               5

<210> SEQ ID NO 47
<211> LENGTH: 5
<212> TYPE: PRT
<213> ORGANISM: Sucker A

<400> SEQUENCE: 47

Gly Ser Gly Ala Asp
1               5

<210> SEQ ID NO 48
<211> LENGTH: 5
<212> TYPE: PRT
<213> ORGANISM: Sucker B

<400> SEQUENCE: 48

Gly Ser Asn Thr Glu
1               5

<210> SEQ ID NO 49
<211> LENGTH: 5
<212> TYPE: PRT
<213> ORGANISM: Carp alpha

<400> SEQUENCE: 49

Gly Gly Gly Ala Asp
1               5

<210> SEQ ID NO 50
<211> LENGTH: 5
<212> TYPE: PRT
<213> ORGANISM: Carp beta1

<400> SEQUENCE: 50

Gly Gly Asn Thr Glu
1               5

<210> SEQ ID NO 51
<211> LENGTH: 5
<212> TYPE: PRT
<213> ORGANISM: Carp beta2

<400> SEQUENCE: 51

Gly Ser Asn Thr Glu
1               5
```

<210> SEQ ID NO 52
<211> LENGTH: 5
<212> TYPE: PRT
<213> ORGANISM: Carp gamma

<400> SEQUENCE: 52

Gly Gly Gly Ala Asp
1               5

<210> SEQ ID NO 53
<211> LENGTH: 5
<212> TYPE: PRT
<213> ORGANISM: Flounder

<400> SEQUENCE: 53

Ala Gly Thr Thr Glu
1               5

<210> SEQ ID NO 54
<211> LENGTH: 5
<212> TYPE: PRT
<213> ORGANISM: Trout

<400> SEQUENCE: 54

Gly Gly Asn Ser Glu
1               5

<210> SEQ ID NO 55
<211> LENGTH: 5
<212> TYPE: PRT
<213> ORGANISM: Grouper

<400> SEQUENCE: 55

Ala Gly Asn Ser Glu
1               5

<210> SEQ ID NO 56
<211> LENGTH: 6
<212> TYPE: PRT
<213> ORGANISM: Frog

<400> SEQUENCE: 56

Ala Gly Asn Leu Ser Glu
1               5

<210> SEQ ID NO 57
<211> LENGTH: 5
<212> TYPE: PRT
<213> ORGANISM: Chicken

<400> SEQUENCE: 57

Gly Asn Leu Ser Glu
1               5

<210> SEQ ID NO 58
<211> LENGTH: 5
<212> TYPE: PRT
<213> ORGANISM: Zebra finch

<400> SEQUENCE: 58

Gly Asn Leu Ser Glu
1               5

<210> SEQ ID NO 59

```
<211> LENGTH: 10
<212> TYPE: PRT
<213> ORGANISM: Mouse
<220> FEATURE:
<221> NAME/KEY: misc_feature
<222> LOCATION: (1)..(1)
<223> OTHER INFORMATION: Xaa is Pyr

<400> SEQUENCE: 59

Xaa His Lys Gln His Gly Ala Ala Pro Glu
1               5                   10

<210> SEQ ID NO 60
<211> LENGTH: 7
<212> TYPE: PRT
<213> ORGANISM: Rat
<220> FEATURE:
<221> NAME/KEY: misc_feature
<222> LOCATION: (1)..(1)
<223> OTHER INFORMATION: Xaa is Pyr

<400> SEQUENCE: 60

Xaa His Gly Thr Ala Pro Glu
1               5

<210> SEQ ID NO 61
<211> LENGTH: 5
<212> TYPE: PRT
<213> ORGANISM: Porcine A

<400> SEQUENCE: 61

Gly Pro Thr Ser Glu
1               5

<210> SEQ ID NO 62
<211> LENGTH: 5
<212> TYPE: PRT
<213> ORGANISM: Porcine B

<400> SEQUENCE: 62

Gly Pro Pro Ser Glu
1               5

<210> SEQ ID NO 63
<211> LENGTH: 5
<212> TYPE: PRT
<213> ORGANISM: Cattle

<400> SEQUENCE: 63

Gly Pro Ser Ser Glu
1               5

<210> SEQ ID NO 64
<211> LENGTH: 4
<212> TYPE: PRT
<213> ORGANISM: Monkey

<400> SEQUENCE: 64

Glu Thr Pro Asp
1

<210> SEQ ID NO 65
<211> LENGTH: 4
<212> TYPE: PRT
<213> ORGANISM: Chimpanzee

<400> SEQUENCE: 65
```

```
Glu Thr Pro Asp
1

<210> SEQ ID NO 66
<211> LENGTH: 4
<212> TYPE: PRT
<213> ORGANISM: Homo Sapien

<400> SEQUENCE: 66

Glu Thr Pro Asp
1

<210> SEQ ID NO 67
<211> LENGTH: 11
<212> TYPE: PRT
<213> ORGANISM: Homo Sapien

<400> SEQUENCE: 67

Glu Thr Pro Asp Cys Phe Trp Lys Tyr Cys Val
1               5                   10

<210> SEQ ID NO 68
<211> LENGTH: 8
<212> TYPE: PRT
<213> ORGANISM: Homo Sapien

<400> SEQUENCE: 68

Ala Cys Phe Trp Lys Tyr Cys Val
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is 1-Nal

<400> SEQUENCE: 69

Ala Cys Phe Xaa Lys Tyr Cys Val
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is D-1-Nal

<400> SEQUENCE: 70

Ala Cys Phe Xaa Lys Tyr Cys Val
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: misc_feature
<222> LOCATION: (4)..(4)
<223> OTHER INFORMATION: Xaa is Phe(I)

<400> SEQUENCE: 71

Ala Cys Phe Xaa Lys Tyr Cys Val
1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is Cha

<400> SEQUENCE: 72

Ala Cys Phe Xaa Lys Tyr Cys Val
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is Tbg

<400> SEQUENCE: 73

Ala Cys Phe Xaa Lys Tyr Cys Val
1               5

<210> SEQ ID NO 74
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is D-Tbg

<400> SEQUENCE: 74

Ala Cys Phe Xaa Lys Tyr Cys Val
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is Dip

<400> SEQUENCE: 75

Ala Cys Phe Xaa Lys Tyr Cys Val
1               5

<210> SEQ ID NO 76
```

```
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is Tpi

<400> SEQUENCE: 76

Ala Cys Phe Xaa Lys Tyr Cys Val
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is D-Tpi

<400> SEQUENCE: 77

Ala Cys Phe Xaa Lys Tyr Cys Val
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is Aia

<400> SEQUENCE: 78

Ala Cys Phe Xaa Lys Tyr Cys Val
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is D-Aia

<400> SEQUENCE: 79

Ala Cys Phe Xaa Lys Tyr Cys Val
1               5

<210> SEQ ID NO 80
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is Phg

<400> SEQUENCE: 80
```

```
Ala Cys Phe Xaa Lys Tyr Cys Val
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa D-Phg

<400> SEQUENCE: 81

Ala Cys Phe Xaa Lys Tyr Cys Val
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is Tiq

<400> SEQUENCE: 82

Ala Cys Phe Xaa Lys Tyr Cys Val
1               5

<210> SEQ ID NO 83
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is D-Tiq

<400> SEQUENCE: 83

Ala Cys Phe Xaa Lys Tyr Cys Val
1               5

<210> SEQ ID NO 84
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is Tic

<400> SEQUENCE: 84

Ala Cys Phe Xaa Lys Tyr Cys Val
1               5

<210> SEQ ID NO 85
<211> LENGTH: 8
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: misc_feature
<222> LOCATION: (4)..(4)
<223> OTHER INFORMATION: Xaa is D-Tic

<400> SEQUENCE: 85

Ala Cys Phe Xaa Lys Tyr Cys Val
1               5

<210> SEQ ID NO 86
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa is Pen
<220> FEATURE:
<221> NAME/KEY: misc_feature
<222> LOCATION: (4)..(4)
<223> OTHER INFORMATION: Xaa is Tiq

<400> SEQUENCE: 86

Ala Xaa Phe Xaa Lys Tyr Cys Asx
1               5

<210> SEQ ID NO 87
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is Tiq
<220> FEATURE:
<221> NAME/KEY: misc_feature
<222> LOCATION: (5)..(5)
<223> OTHER INFORMATION: Xaa is Orn

<400> SEQUENCE: 87

Ala Cys Phe Xaa Xaa Tyr Cys Val
1               5

<210> SEQ ID NO 88
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is Tpi
<220> FEATURE:
<221> NAME/KEY: misc_feature
<222> LOCATION: (5)..(5)
<223> OTHER INFORMATION: Xaa is Orn

<400> SEQUENCE: 88

Ala Cys Phe Xaa Xaa Tyr Cys Val
1               5

<210> SEQ ID NO 89
<211> LENGTH: 8
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: misc_feature
<222> LOCATION: (4)..(4)
<223> OTHER INFORMATION: Xaa is Bip

<400> SEQUENCE: 89

Ala Cys Phe Xaa Lys Tyr Cys Val
1               5

<210> SEQ ID NO 90
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is Pyr

<400> SEQUENCE: 90

Xaa His Gly Thr Ala Pro Glu
1               5

<210> SEQ ID NO 91
<211> LENGTH: 8
<212> TYPE: PRT
<213> ORGANISM: Homo Sapien

<400> SEQUENCE: 91

Ala Cys Phe Phe Lys Tyr Cys Val
1               5

<210> SEQ ID NO 92
<211> LENGTH: 6
<212> TYPE: PRT
<213> ORGANISM: Artificial sequence
<220> FEATURE:
<223> OTHER INFORMATION: Synthetic peptide

<400> SEQUENCE: 92

Cys Phe Trp Lys Tyr Cys
1               5
```